US006177154B1

(12) United States Patent
Matsui et al.

(10) Patent No.: US 6,177,154 B1
(45) Date of Patent: Jan. 23, 2001

(54) ALKOXYBENZENE DERIVATIVE, LIQUID-CRYSTAL COMPOSITION, AND LIQUID-CRYSTAL DISPLAY ELEMENT

(75) Inventors: Shuichi Matsui; Tugumiti Andou; Kazutoshi Miyazawa; Hiroyuki Takeuchi; Yasusuke Hisatsune; Fusayuki Takeshita; Etsuo Nakagawa, all of Chiba (JP)

(73) Assignee: Chisso Corporation, Osaka (JP)

( * ) Notice: Under 35 U.S.C. 154(b), the term of this patent shall be extended for 0 days.

(21) Appl. No.: 09/254,682

(22) PCT Filed: Sep. 16, 1997

(86) PCT No.: PCT/JP97/03258

§ 371 Date: Mar. 16, 1999

§ 102(e) Date: Mar. 16, 1999

(87) PCT Pub. No.: WO98/12166

PCT Pub. Date: Mar. 26, 1998

(30) Foreign Application Priority Data

Sep. 17, 1996 (JP) .................................................... 8-266804

(51) Int. Cl.[7] .......................... C09K 19/34; C09K 19/20; C07C 43/205; C07C 69/76; C07D 239/02; C07D 319/04

(52) U.S. Cl. ................ 428/1.1; 252/299.61; 252/299.63; 252/299.64; 252/299.65; 252/299.66; 544/298; 544/335; 549/374; 560/61; 560/62; 568/631; 568/634

(58) Field of Search ......................... 252/299.61, 299.63, 252/299.64, 299.66, 299.65; 544/298, 335; 549/374; 560/61, 62; 568/631, 634; 428/1.1

(56) References Cited

U.S. PATENT DOCUMENTS 5,032,313 7/1991 Goto et al. ...................... 252/299.63

FOREIGN PATENT DOCUMENTS 4027840 3/1991 (DE) .
8-143498 6/1996 (JP) .
89/02884 4/1989 (WO) .

OTHER PUBLICATIONS

Bezborodov et al., "Synthesis and properties of some laterally substituted liquid crystals", Liq. Crystl., vol. 21, No. 6, 1996, pp. 801–806.

CA 96: 69387, 1981.*

* cited by examiner

*Primary Examiner*—Shean C. Wu
(74) *Attorney, Agent, or Firm*—Wenderoth, Lind & Ponack, L.L.P.

(57) ABSTRACT

Disclosed are (a) liquid crystalline compounds which are essential as component of the liquid crystal compositions, are excellent in miscibility with other liquid crystal compositions, particularly in the miscibility at low temperatures, and expressed by the general formula (1)

(1)

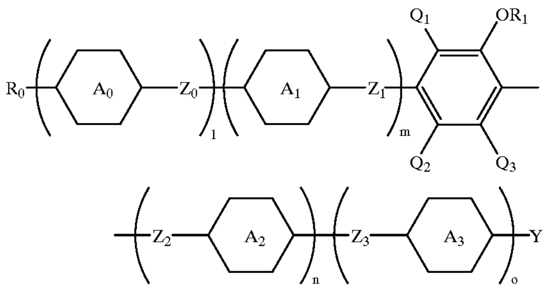

wherein $R_0$ and $R_1$ independently represent an alkyl group having 1 to 10 carbon atoms; ring $A_0$, ring $A_1$, ring $A_2$, and ring $A_3$ represent 1,4-cyclohexylene group, 1,3-dioxane-2,5-diyl group, 1,4-phenylene group in which one or more hydrogen atoms on the ring may be represented by a halogen atom or $R_2O$ group, pyridine-2,5-diyl group, or pyrimidine-2,5-diyl group; $Z_0$, $Z_1$, $Z_2$, and $Z_3$ represent $—CH_2CH_2—$, $—CH{=}CH—$, $—C{\equiv}C—$, $—CH_2O—$, $—OCH_2—$, $—CF_2O—$, $—OCF_2—$, $—COO—$, $—OCO—$, $—(CH_2)_4—$, or single bond; $Q_1$ and $Q_2$ represent hydrogen atom or a halogen atom; $Q_3$ represents hydrogen atom, a halogen atom, or $R_2O$ group; $R_2$ represents an alkyl group having 1 to 10 carbon atoms; Y represents a halogen atom, cyano group, or an alkyl group having 1 to 10 carbon atoms; l, m, n and o are 0, 1, or 2 with the proviso that $1 \leqq l+m+n+o \leqq 3$; and the atom which constitutes this compound may be replaced by its isotope; and (b) liquid crystal display devices fabricated by using the liquid crystal composition.

22 Claims, No Drawings

ALKOXYBENZENE DERIVATIVE, LIQUID-CRYSTAL COMPOSITION, AND LIQUID-CRYSTAL DISPLAY ELEMENT

This application is a 371 of PCT/JP97/03258, filed Sep. 16, 1997.

TECHNICAL FIELD

The present invention relates to novel liquid crystalline compounds which can develop intended physical properties by mixing them with a liquid crystal composition used for liquid crystal display devices and relates to the liquid crystal compositions thus produced. Further, the present invention relates to liquid crystal display devices fabricated by using the liquid crystal composition.

BACKGROUND ART

Liquid crystal display devices have widely been utilized for tabletop calculators, word processors, television sets, and the likes, including watches. As their applications became upscale, however, liquid crystal compositions having more appropriate physical property values became necessary. As the result, liquid crystal compositions having such a low threshold voltage that devices were capable of being driven at a low voltage, and liquid crystal compositions having such a high voltage holding ratio that the reliability of devices was increased were developed.

Threshold voltage (Vth) is expressed by the following equation (H. J. Deuling et al., Mol. Cryst. Liq. Cryst., 27 (1975) 81):

$$Vth=\pi(K/\in 0\Delta\in)^{1/2}$$

wherein K denotes an elastic constant, ∈0: a dielectric constant in vacuum, and Δ∈: a dielectric anisotropy value. From this equation, it can be understood that in order to lower threshold voltage, it is sufficient to increase the dielectric anisotropy or decrease the elastic constant. Generally, dielectric anisotropy is more often controlled than elastic constant, since many liquid crystal compounds having a high dielectric anisotropy are known.

Besides, threshold voltage depends also on the pretilt angle of liquid crystal compositions induced in a device. When both dielectric anisotropy and elastic constant are constant, the larger the pretilt angle is, the lower the threshold voltage tends to be. Compounds of the formula (10) described in Laid-open Japanese Patent Publication No. Hei 2-501311 induce a comparatively large pretilt angle.

(10)

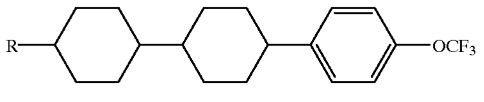

Laid-open Japanese Patent Publication No Hei 2-501311)

in the structural formula described above, R represents an alkyl group.

Liquid crystal compositions comprising a compound of the formula (10) are promising since they are low in dependency of voltage holding ratio on temperature, induce a comparatively large pretilt angle, and have a high reliability. However, they are not suitable for the applications wherein devices are driven at such a low voltage of 2.5 V, because their dielectric anisotropy values are such a medium extent as about 7 since contribution of trifluoromethoxy group to dielectric anisotropy is small.

On the other hand, it is known that liquid crystal compositions comprising a fluorine type liquid crystalline compound are high in voltage holding ratio and low in their dependency on temperature.

(11)

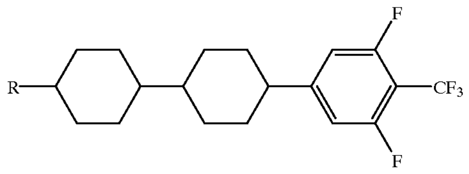

(DE-4027840A1)

(12-1)

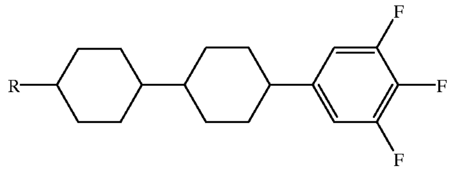

(Laid-open Japanese Patent Publication No. Hei 2-233626)

(12-2)

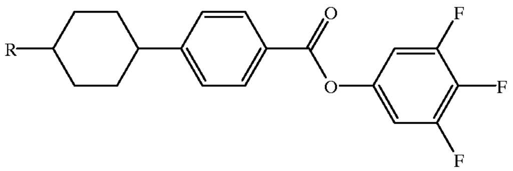

(Laid-open Japanese Patent Publication No. Hei 2-233626)

in the structural formulas described above, R represents an alkyl group.

Compounds having a plural number of fluorine atom at a terminal of the molecule of the formula (11) (DE-4027840A1), and formulas (12-1) and (12-2) (Laid-open Japanese Patent Publication No. Hei 2-233626) have a comparatively high dielectric anisotropy. However, when compounds of the formula (11) are used as component of liquid crystal compositions, the extent to which threshold voltage of the compositions is lowered is small since the compounds have a large elastic constant whereas trifluoromethyl group in the compounds contributes to a high dielectric anisotropy. Also, they induce a low pretilt angle. Accordingly, the compounds can not be said to be suitable for the applications at a low voltage. When compounds of the formulas (12-1) are used, the compositions exhibit a comparatively high voltage holding ratio and are small in dependency of voltage holding ratio on temperature. However, their dielectric anisotropy is lower than the case where a compound of the formula (11) is used. Whereas compounds of the formula (12-2) have a high dielectric anisotropy due to the contribution by 3,4,5-trifulorophenyl group and ester bonding group, and are larger in contribution to the pretilt angle in liquid crystal compositions than compounds of the formula (11), the compounds are large in dependency of voltage holding ratio on temperature. Thus, applications of compounds of the formula (12-2) are limited. Accordingly, liquid crystalline compounds from which liquid crystal compositions having a low threshold voltage, exhibiting a high voltage holding ratio, and being small in dependency of voltage holding ratio on temperature can be produced have been desired.

DISCLOSURE OF THE INVENTION

A subject of the present invention is to provide liquid crystal compositions which 1) are low in threshold voltage,
2) induce a large pretilt angle, and
3) are high in voltage holding ratio and are low in its dependency on temperature, to make the driving of liquid crystal display devices at a low voltage possible and to impart a high reliability to the devices at the same time. Further subject of the present invention is to find novel liquid crystalline compounds which are essential as component of the liquid crystal compositions and are excellent in miscibility with other liquid crystal compositions, particularly in the miscibility at low temperatures.

It was predicted by the present inventors that in the compounds of the formula (10) disclosed in the Laid-open Japanese Patent Publication No. Hei 2-501311 mentioned above, the oxygen atom in trifluoromethoxy group contributes in increasing pretilt angle. Based on this forecast, the following model compounds (13) (Compound No. 195) and (14) (Compound No. 199) in which one or two alkoxy groups are introduced at position 3 and position 5 in 4-fluorophenyl group were synthesized and then their physical property values were compared to study.

(13)

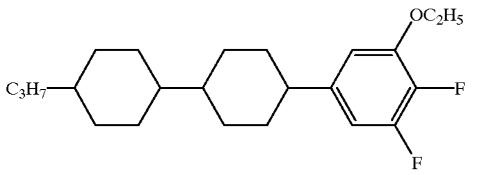

(Compound No. 195)

(14)

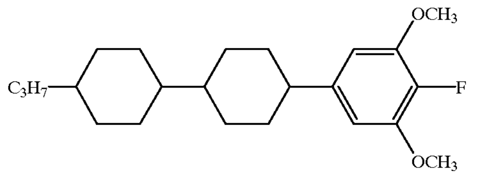

(Compound No. 199)

As the result, it has been found out that these compounds have a remarkably higher dielectric anisotropy than the compounds in which a halogen atom is introduced at the same position as those in the compounds (13) and (14), and are excellent in miscibility with liquid crystal compositions, particularly in the miscibility at low temperatures. When liquid crystal compositions were prepared by using the compounds in which one or more alkoxy groups were introduced, it was found out that pretilt angle of the compositions became larger than expected, their voltage holding ratio was high, and dependency of voltage holding ratio on temperature was small. As the result of further investigation to generalize the forecast described above, the present invention has now been accomplished.

The present invention to achieve the purposes described above is summarized in the following aspects [1] to [23]:

[1] A liquid crystalline compound expressed by the general formula (1)

(1)

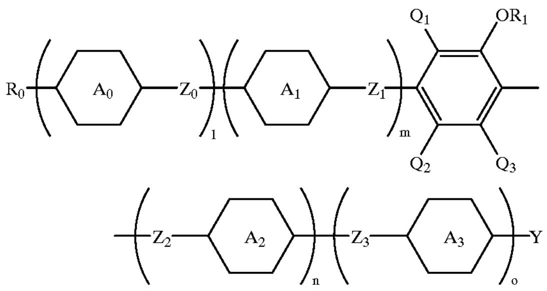

wherein $R_0$ and $R_1$ independently represent an alkyl group having 1 to 10 carbon atoms in which alkyl group one or more not-adjacent methylene groups may be replaced by oxygen atom, sulfur atom, $—SiH_2—$, $—CH{=}CH—$, or $—C{\equiv}C—$, and any hydrogen atom in the alkyl group may be replaced by a halogen atom;

ring $A_0$, ring $A_1$, ring $A_2$, and ring $A_3$ independently represent 1,4-cyclohexylene group, 1,3-dioxane-2,5-diyl group, 1,4-phenylene group in which one or more hydrogen atoms on the ring may be replaced by a halogen atom or $R_2O$ group, pyridine-2,5-diyl group, or pyrimidine-2,5-diyl group;

$Z_0$, $Z_1$, $Z_2$, and $Z_3$ independently represent $—CH_2CH_2—$, $—CH{=}CH—$, $—C{\equiv}C—$, $—CH_2O—$, $—OCH_2—$, $—CF_2O—$, $—OCF_2—$, $—COO—$, $—OCO—$, $—(CH_2)_4—$, or single bond;

$Q_1$ and $Q_2$ independently represent hydrogen atom or a halogen atom;

$Q_3$ represents hydrogen atom, a halogen atom, or $R_2O$ group;

$R_2$ represents an alkyl group having 1 to 10 carbon atoms in which alkyl group one or more not-adjacent methylene groups may be replaced by $—SiH_2—$, $—CH{=}CH—$, or $—C{\equiv}C—$, and any hydrogen atom in the alkyl group may be replaced by a halogen atom;

Y represents a halogen atom, cyano group, or an alkyl group having 1 to 10 carbon atoms in which alkyl group one or more not-adjacent methylene groups may be replaced by oxygen atom, sulfur atom, $—SiH_2—$, $—CH{=}CH—$, or $—C{\equiv}C—$, and any hydrogen atom in the alkyl group may be replaced by a halogen atom;

l, m, n and o are independently 0, 1, or 2 with the proviso that $l+m+n+o \leqq 3$;

provided that when one of $Z_0$, $Z_1$, $Z_2$, and $Z_3$ is $—COO—$, then Y is not cyano group, and that when n=o=0, $Z_0$ and $Z_1$ are a group selected from $—CH_2CH_2—$, $—CH_2O—$, $—OCH_2—$, $—(CH_2)_4—$, $—C{\equiv}C—$, and single bond, $Q_3$ is fluorine atom, and Y is fluorine atom or chlorine atom, then $R_2$ is $C_2H_5$ group; and the atom which constitutes this compound may be replaced by its isotope.

[2] The liquid crystalline compound of the aspect [1] of the present invention wherein l=1, and m=n=o=0 in the general formula (1).

[3] The liquid crystalline compound of the aspect [1] of the present invention wherein l=m=1, and n=o=0 in the general formula (1).

[4] The liquid crystalline compound of the aspect [1] of the present invention wherein l=n=1, and m=o=0 in the general formula (1).

[5] The liquid crystalline compound of the aspect [1] of the present invention wherein l=2, m=1, and n=o=0 in the general formula (1).

[6] The liquid crystalline compound of the aspect [1] of the present invention wherein l=1, m=2, and n=o=0 in the general formula (1).

[7] The liquid crystalline compound of the aspect [1] of the present invention wherein l=m=n=1, and o=0 in the general formula (1).

[8] The liquid crystalline compound of the aspect [2] of the present invention wherein $Q_3$ is $R_2O$ group in the general formula (1).

[9] The liquid crystalline compound of the aspect [3] of the present invention wherein $Q_3$ is $R_2O$ group in the general formula (1).

[10] The liquid crystalline compound of the aspect [4] of the present invention wherein $Q_3$ is $R_2O$ group in the general formula (1).

[11] The liquid crystalline compound of the aspect [5] of the present invention wherein $Q_3$ is $R_2O$ group in the general formula (1).

[12] The liquid crystalline compound of the aspect [6] of the present invention wherein $Q_3$ is $R_2O$ group in the general formula (1).

[13] The liquid crystalline compound of the aspect [7] of the present invention wherein $Q_3$ is $R_2O$ group in the general formula (1).

[14] The liquid crystalline compound of the aspect [1] of the present invention wherein any one of $Z_0$, $Z_1$, $Z_2$, and $Z_3$ is —$CF_2O$— group in the general formula (1).

[15] The liquid crystalline compound of the aspect [1] of the present invention wherein at least one of ring $A_0$, ring $A_1$, ring $A_2$, and ring $A_3$ is 1,4-phenylene group in which one or more hydrogen atoms may be replaced by $R_2O$ group in the general formula (1).

[16] A liquid crystal composition comprising at least two components and comprising at least one compound expressed by the general formula (1).

[17] A liquid crystal composition comprising, as a first component, at least one compound recited in any one of the aspects [1] to [15], and comprising, as a second component, at least one compound selected from the group consisting of the compounds expressed by any one of the general formulas (2), (3), and (4)

(2)

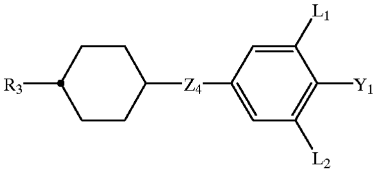

(3)

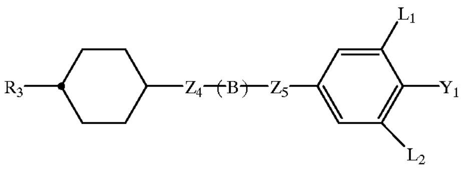

-continued (4)

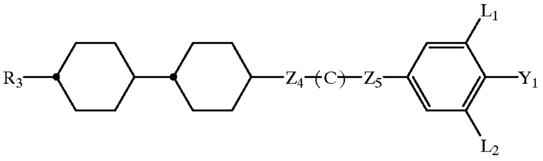

wherein $R_3$ represents an alkyl group having 1 to 10 carbon atoms in which alkyl group one or more not-adjacent methylene groups may be replaced by oxygen atom or —CH=CH—, and any hydrogen atom in the alkyl group may be replaced by fluorine atom;

$Y_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$;

$L_1$ and $L_2$ independently represent hydrogen atom or fluorine atom;

$Z_4$ and $Z_5$ independently represent 1,2-ethylene group, 1,4-butylene group, —COO—, —$CF_2O$—, —$OCF_2$—, —C=CH—, or single bond;

ring B represents trans-1,4-cyclohexylene, 1,3-dioxane-2,5-diyl, or 1,4-phenylene in which hydrogen atom may be replaced by fluorine atom;

ring C represents 1,4-cyclohexylene, or 1,4-phenylene in which hydrogen atom may be replaced by fluorine atom; and the atom which constitutes this compound may be replaced by its isotope.

[18] A liquid crystal composition comprising, as a first component, at least one compound recited in any one of the aspects [1] to [15], and comprising, as a second component, at least one compound selected from the group consisting of the compounds expressed by the general formula (5) or (6)

(5)

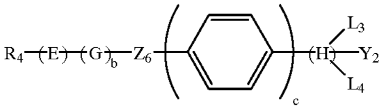

(6)

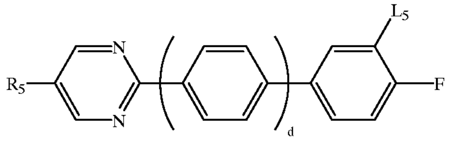

wherein $R_4$ and $R_5$ independently represent an alkyl group having 1 to 10 carbon atoms in which alkyl group one or more not-adjacent methylene groups may be replaced by oxygen atom or —CH=CH—, and any hydrogen atom in the alkyl group may be replaced by fluorine atom;

$Y_2$ represents cyano group or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene, 1,4-phenylene in which hydrogen atom may be replaced by fluorine atom, or pyrimidine-2,5-diyl;

ring H represents trans-1,4-cyclohexylene or 1,4-phenylene;

$Z_6$ represents —$CH_2CH_2$—, —COO—, or single bond;

$L_3$, $L_4$, and $L_5$ independently represent hydrogen atom or fluorine atom;

b, c, and d are independently 0 or 1; and the atom which constitutes this compound may be replaced by its isotope.

[19] A liquid crystal composition comprising, as a first component, at least one compound recited in any one of the aspects [1] to [15], comprising, as a second component, at least one compound selected from the group consisting of the compounds expressed by any one of the general formulas (2), (3), and (4) described above, and comprising, as a third component, at least one compound selected from the group consisting of the compounds expressed by any one of the general formulas (7), (8), and (9)

(7)

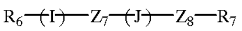

(8)

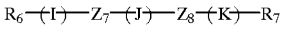

(9)

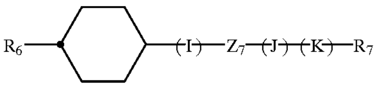

wherein $R_6$ and $R_7$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

ring I, ring J, and ring K independently represent trans-1,4-cyclohexylene, pyrimidine-2,5-diyl, or 1,4-phenylene in which hydrogen atom may be replaced by fluorine atom;

$Z_7$ and $Z_8$ independently represent —C≡C—, —COO—, —$CH_2CH_2$—, —CH═CH—, or single bond; and the atom which constitutes this compound may be replaced by its isotope.

[20] A liquid crystal composition comprising, as a first component, at least one compound recited in any one of the aspects [1] to [15], as a second component, at least one compound selected from the group consisting of the compounds expressed by the general formula (5) or (6) described above, and comprising, as a third component, at least one compound selected from the group consisting of the compounds expressed by any one of the general formulas (7), (8), and (9) described above.

[21] A liquid crystal composition comprising, as a first component, at least one compound defined in any one of the aspects [1] to [15], comprising, as a second component, at least one compound selected from the group consisting of the compounds expressed by any one of the general formulas (2), (3), and (4) described above, comprising, as a third component, at least one compound selected from the group consisting of the compounds expressed by the genera formula (5) or (6) described above, and comprising, as a fourth component, at least one compound selected from the group consisting of the compounds expressed by any one of the general formulas (7), (8), and (9) described above.

[22] A liquid crystal composition further comprising at least one optically active compound in addition to the liquid crystal composition recited in any one of the aspects [16] to [21].

[23] A liquid crystal display device fabricated by using a liquid crystal composition recited in any one of the aspects [16] to [22].

Compounds of the present invention expressed by the general formula (1) are excellent in miscibility when added in liquid crystal compositions, particularly in the miscibility at low temperatures. Liquid crystal compositions comprising the compound of the present invention are remarkably high in dielectric anisotropy, low in threshold voltage, large in pretilt angle, high in voltage holding ratio, and small in the dependency of voltage holding ratio on temperature. While the compounds of the present invention exhibit preferable physical properties as described above, more appropriate liquid crystal compositions can be produced to fabricate liquid crystal display devices by selecting $R_0$, $R_1$, $R_2$, ring $A_0$, ring $A_1$, ring $A_2$, ring $A_3$, $Z_0$, $Z_1$, $Z_2$, $Z_3$, $Q_1$, $Q_2$, $Q_3$, l, m, n, and o in the general formula (1) according to the purposes.

When a high dielectric anisotropy is required, it is better to select cyano group, $CF_3$ group, $OCF_3$ group, or $OCHF_2$ group as substituent Y. When a higher dielectric anisotropy is required, it is better to select —$CF_2O$— or —COO— for at least one of bonding groups $Z_0$, $Z_1$, $Z_2$, and $Z_3$, and further to introduce a halogen atom, preferably fluorine atom to a lateral position of ring $A_0$, ring $A_1$, ring $A_2$, or ring $A_3$ so that dipole moment of the molecule is increased. In this connection, compounds in which an atom at a lateral position of ring $A_0$, ring $A_1$, ring $A_2$, or ring $A_3$ is replaced by fluorine atom are excellent in the miscibility, particularly in the miscibility at low temperature compared with the compounds in which the replacement is not taken place.

In the case where substituent $R_0$ is an alkenyl group and Y is cyano group, the compounds are extremely useful for the applications where devices are driven at a low voltage since the viscosity is low and dielectric anisotropy is high. As will be clear from Examples and Comparative Examples, while the compounds of the present invention exhibit a high dielectric anisotropy, this is caused by the effect of $R_1O$ group on 1,4-phenylene group. In other words, this is because the dipole based on an unshared electron pair of the oxygen atom in $R_1O$ group efficiently acts to the direction of major axis of the molecule.

In the case of the compound of the formula (13) (Compound No. 195), it can be considered that the compound has a high dielectric anisotropy since the direction of dipole based on an unshared electron pair of the oxygen atom in ethoxy group existing at ortho position to fluorine atom is the same as that of dipole based on fluorine atom. Also, the oxygen atom in the ethoxy group can be considered to contribute even to a large pretilt angle.

Hereupon, the compound of the formula (A) which resembles the compounds of the present invention is disclosed in Laid-open Japanese Patent Publication No. Hei 8-143498.

(A)

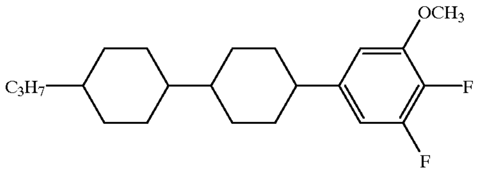

(Laid-open Japanese Patent Publication No. Hei 8-143498)

In the case of the compound of the formula (A) described above, the dipole moment based on an unshared electron pair of oxygen atom is offset by its free rotation, and as the result, an effect of increasing dielectric anisotropy can not be expected, because the substituent (alkoxy group) is methoxy group and exists at a terminal of the molecule, and the methoxy group substituted on benzene ring is small in energy barrier of free rotation and thus can readily rotates. On the other hand, in the case where the substituent is an alkoxy group having a chain length of ethoxy group or longer, an effect of largely increasing dielectric anisotropy can be expected, because the energy barrier of free rotation is large even when the substituents exist at a terminal of the molecule, and the free rotation is inhibited, and thus, when compounds have the same skeleton as the compound of the formula (A) described above, the stable direction of an unshared electron pair of the oxygen atom in alkoxy group is the same as that of the dipole moment of fluorine atom substituted at ortho position. However, ethoxy group is preferable as the alkoxy group at a terminal position of molecule, since mesomorphism is considerably deteriorated and viscosity is remarkably increased when the substituent is an alkoxy group having a chain length of propoxy group or longer.

Compounds expressed by the general formula (1) have a higher dielectric anisotropy than the compounds described in the section of BACKGROUND ART, and are not deteriorated under such severe conditions as heating or irradiation of ultraviolet ray. Also, the compounds of the general formula (1) are high in voltage holding ratio and low in its dependency on temperature.

Particularly, when liquid crystal compositions having a high reliability are to be produced, compounds in which an alkyl group or fluoroalkyl group is selected as side chain $R_0$ and $R_1$, a group which is not an ester group is selected as bonding group $Z_0$, $Z_1$, $Z_2$, and $Z_3$, and a group which is not cyano group is selected as substituent Y are used.

When liquid crystal compositions having a higher upper limit temperature up to which the compositions exhibit liquid crystal phase are to be produced, it is better that four-ring system compounds in which l+m+n+o=3 in the general formula (1) are adopted, and an alkyl group having such a short carbon chain as methyl group, ethyl group, ethenyl group, and fluoromethyl group, alkenyl group, or halogen substituted alkyl group is selected as substituent $R_1$. On the other hand, when liquid crystal compositions having a lower viscosity are to be produced, it is better to use a two-ring system or three-ring system compound, preferably a two-ring system compound.

Optical anisotropy can be controlled by selecting a suitable $R_0$, $R_1$, $R_2$, ring $A_0$, ring $A_1$, ring $A_2$, ring $A_3$, $Z_0$, $Z_1$, $Z_2$, $Z_3$, $Q_1$, $Q_2$, $Q_3$, l, m, n, and o in the general formula (1). When a high optical anisotropy is required, it is sufficient to select compounds which have many 1,4-phenylene and in which $Z_0$, $Z_1$, $Z_2$, and $Z_3$ are single bond. On the other hand, when a low optical anisotropy is required, it is sufficient to select compounds having many trans-1,4-cyclohexylene.

As described above, novel liquid crystal display devices which can be driven at a low voltage and have a high reliability while having required physical properties can be provided by using a liquid crystal composition comprising the compound of the present invention.

As the substituent represented by $R_0$ in the general formula (1), an alkyl group, alkoxy group, alkoxyalkyl group, alkenyl group, alkynyl group, alkenyloxy group, alkynyloxy group, halogen substituted alkyl group, halogenated alkoxy group, halogen substituted alkoxyalkyl group, halogen substituted alkenyl group, and halogen substituted alkynyl group can specifically be mentioned. As the group represented by $R_1$ or $R_2$, an alkyl group, alkenyl group, alkynyl group, halogen substituted alkyl group, halogen substituted alkenyl group, and halogen substituted alkynyl group can specifically be mentioned.

As more specific description of the substituent represented by $R_0$, $R_1$, or $R_2$, methyl group, ethyl group, propyl group, butyl group, pentyl group, hexyl group, heptyl group, octyl group, nonyl group, and decyl group can be mentioned as examples of the alkyl group; and as examples of the alkoxy group, methoxy group, ethoxy group, propoxy group, butoxy group, pentoxy group, hexyloxy group, heptyloxy group, nonyloxy group, and decyloxy group; as examples of the alkoxyalkyl group, methoxymethyl group, ethoxymethyl group, propoxymethyl group, butoxymethyl group, methoxyethyl group, methoxypropyl group, methoxybutyl group, ethoxyethyl group, ethoxypropyl group, propoxyethyl group, and propoxypropyl group; as examples of the alkenyl group, vinyl group, 1-propenyl group, 1-butenyl group, 1-pentenyl group, 3-butenyl group, and 3-pentenyl group; as examples of the alkynyl group, ethynyl group, 1-propynyl group, 1-butynyl group, 1-pentynyl group, 3-butynyl group, and 3-pentynyl group; as an example of the alkenyloxy group, allyloxy group; as examples of the halogen substituted alkyl group, trifluoromethyl group, difluoromethyl group, difluorochloromethyl group, 2,2,2-trifluoroethyl group, 2-fluoroethyl group, 3-fluoropropyl group, 4-fluorobutyl group, 5-fluoropentyl group, and 3-chloropropyl group; as examples of the halogenated alkoxy group, trifluoromethoxy group, difluoromethoxy group, difluorochloromethoxy group, pentafluoroethoxy group, 1,1,2,2-tetrafluoroethoxy group, heptafluoropropoxy group, and 1,1,2,3,3,3-hexafluoropropoxy group; as an example of the halogen substituted alkoxyalkyl group, trifluoromethoxymethyl group; as examples of the halogen substituted alkenyl group, 2-fluoroethenyl group, 2,2-difluoroethenyl group, 1,2,2-trifluoroethenyl group, 3-fluoro-1-butenyl group, and 4-fluoro-1-butenyl group; and as an example of the halogen substituted alkynyl group, 3,3,3-trifluoro-1-propynyl group can be mentioned, respectively.

As examples of the substituent represented by Y in the general formula (1), fluorine atom, chlorine atom, bromine atom, cyano group, and an alkyl group, alkoxy group, alkoxyalkyl group, alkenyl group, alkynyl group, alkenyloxy group, alkynyloxy group, halogen substituted alkyl group, halogenated alkoxy group, halogen substituted alkoxyalkyl group, halogen substituted alkenyl group, and halogen substituted alkynyl group can be mentioned. As more specific examples of the alkyl group to halogen substituted alkynyl group mentioned above, the same substituents as those which were mentioned above for $R_0$ can be named.

Preferable embodiments of the alkoxybenzene derivatives expressed by the general formula (1) and used in the aspect [1] of the present invention are the compounds expressed by one of the following general formulas (1-1) to (1-22).

(1-1)
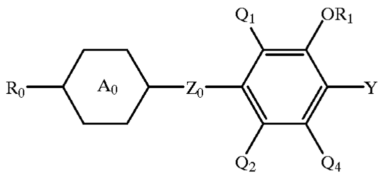
(1-2)
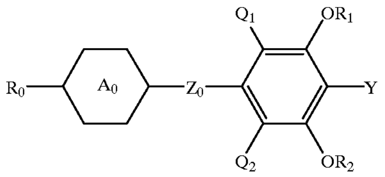
(1-3)
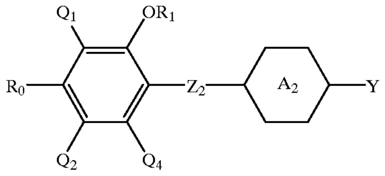
(1-4)
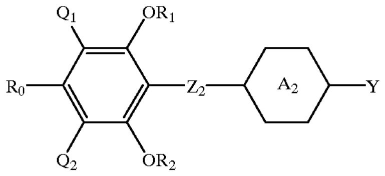
(1-5)
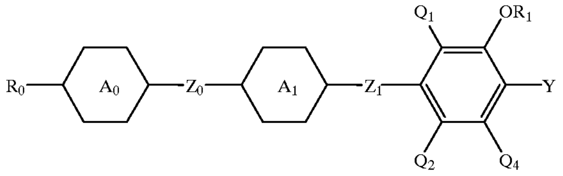
(1-6)
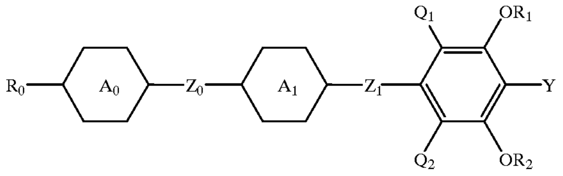
(1-7)
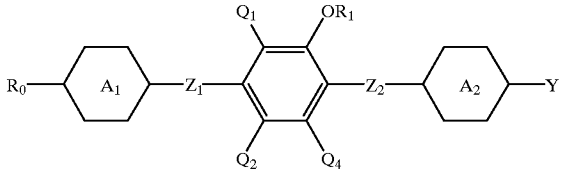
(1-8)
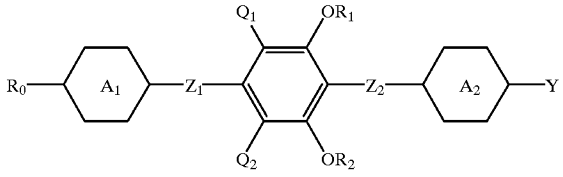

-continued
(1-9)
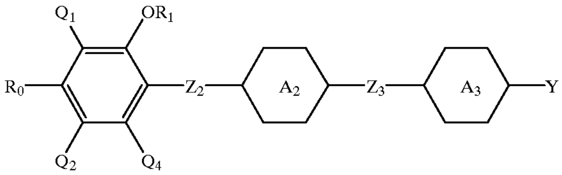
(1-10)
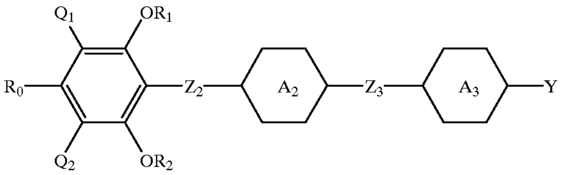
(1-11)
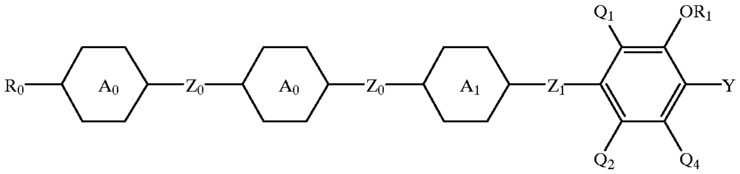
(1-12)
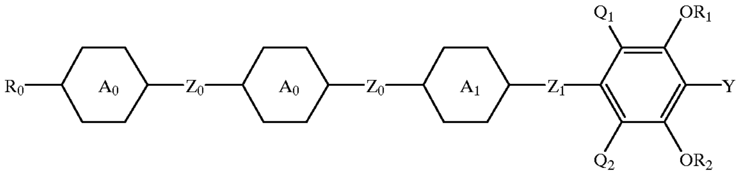
(1-13)
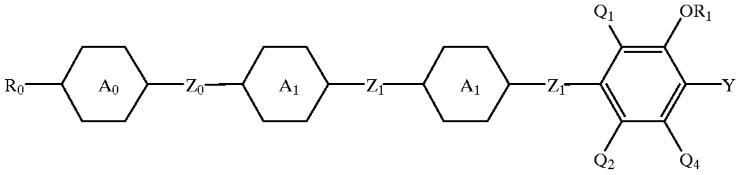
(1-14)
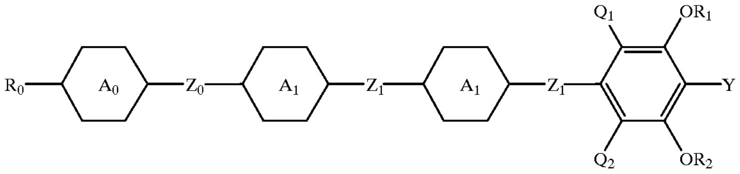
(1-15)
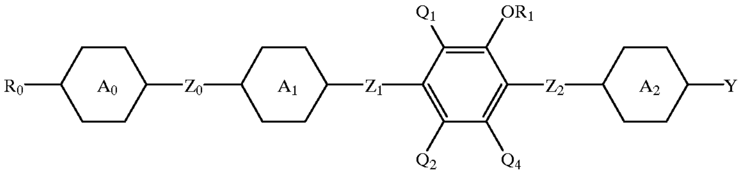
(1-16)
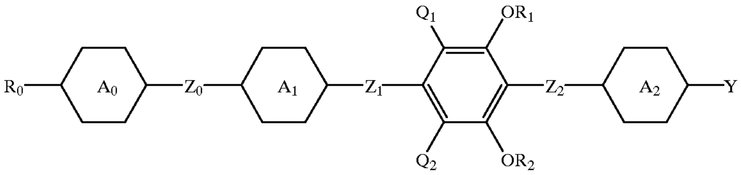

-continued (1-17)

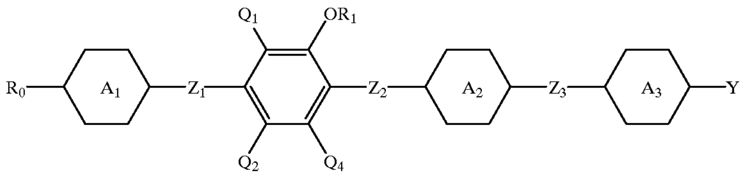

(1-18)

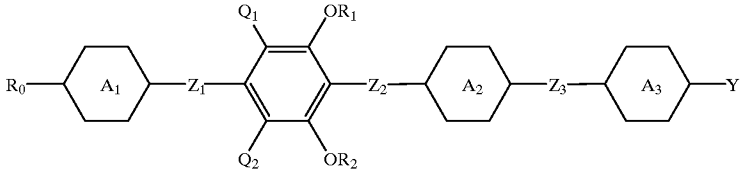

(1-19)

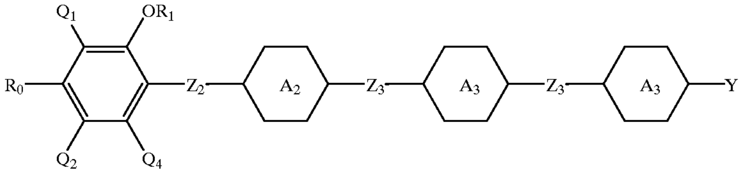

(1-20)

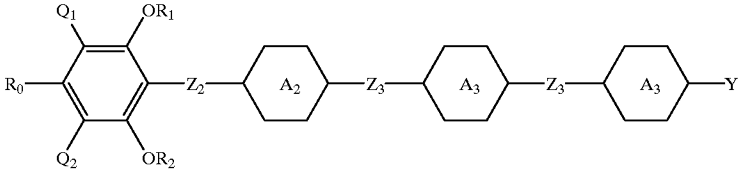

(1-21)

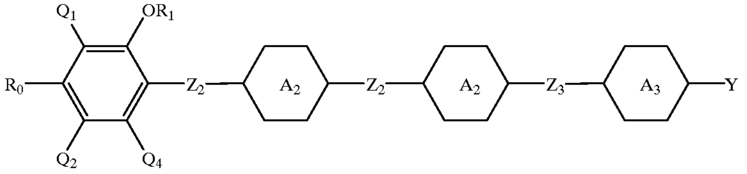

(1-22)

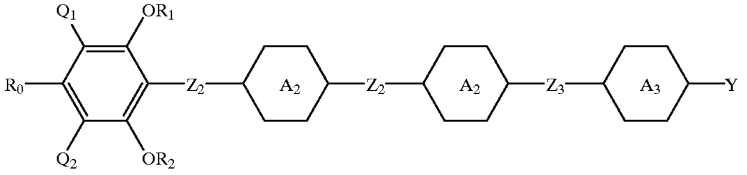

wherein $R_0$, $R_1$, $R_2$, ring $A_0$, ring $A_1$, ring $A_2$, ring $A_3$, $Z_0$, $Z_1$, $Z_2$, $Z_3$, $Q_1$, and $Q_2$ have the same meaning as described above, and $Q_4$ represents hydrogen atom or a halogen atom.

The first of the liquid crystal compositions of the present invention comprises at least one compound expressed by the general formula (1) in an amount of 0.1 to 99.9% by weight, preferably 1 to 50% by weight, and more desirably 3 to 20% by weight. The second of the liquid crystal compositions of the present invention is completed by mixing one or more compounds optionally selected from the group consisting of the compounds expressed by one of the general formulas (2) to (9) with a first component comprising at least one compound expressed by the general formula (1).

As more specific indication of the compounds expressed by one of the general formulas (2) to (4), the compounds expressed by one of the following general formulas can be mentioned.

(2-1)
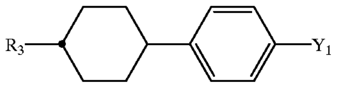
(2-2)
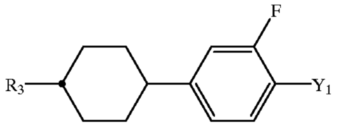
(2-3)
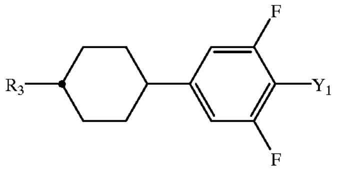
(2-4)
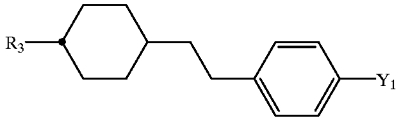
(2-5)
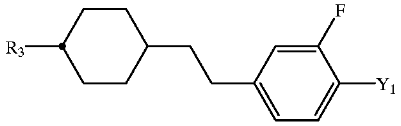
(2-6)
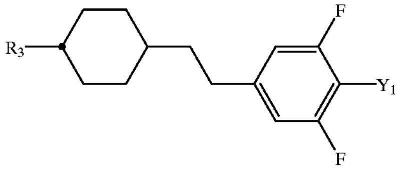
(2-7)
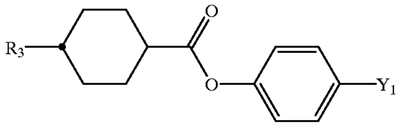
(2-8)
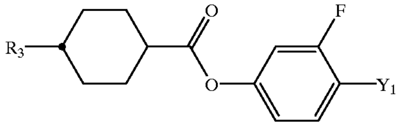
(2-9)
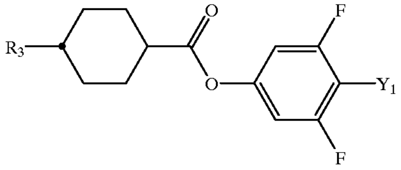
(3-1)
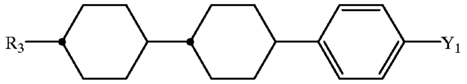

-continued
(3-2)
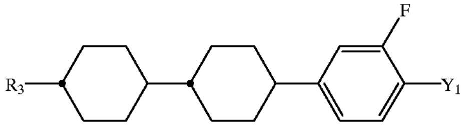
(3-3)
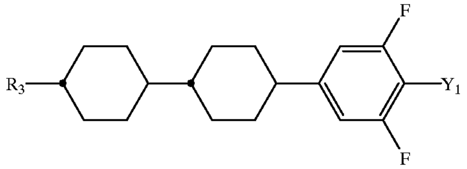
(3-4)
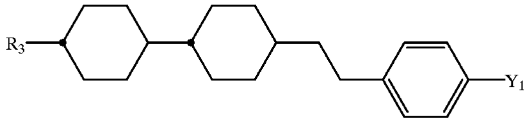
(3-5)
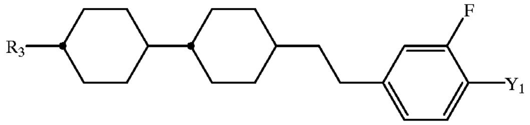
(3-6)
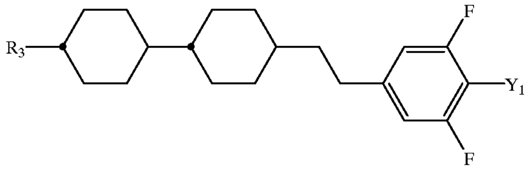
(3-7)
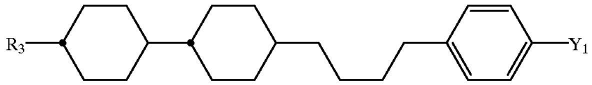
(3-8)
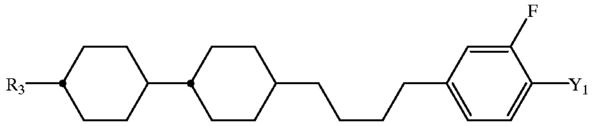
(3-9)
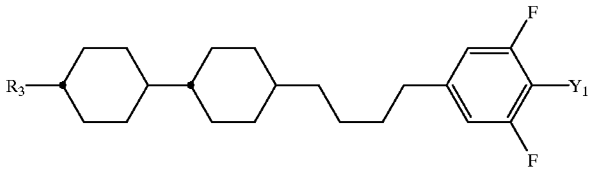
(3-10)
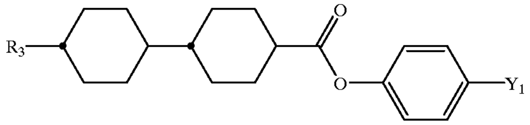
(3-11)
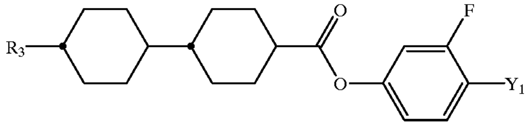

-continued
(3-12)
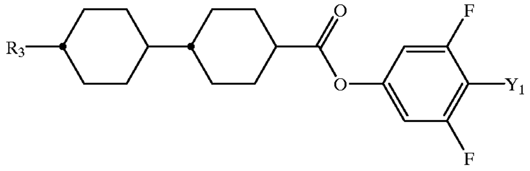
(3-13)
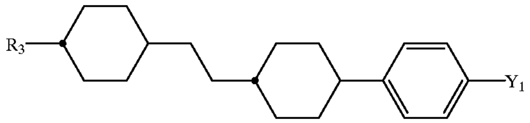
(3-14)
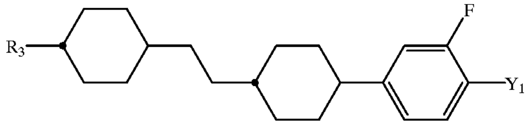
(3-15)
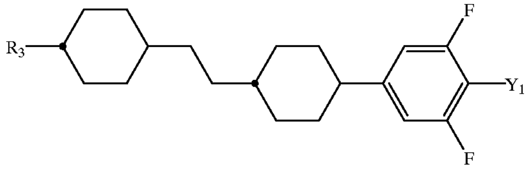
(3-16)
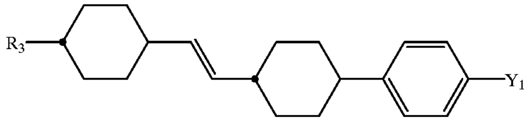
(3-17)
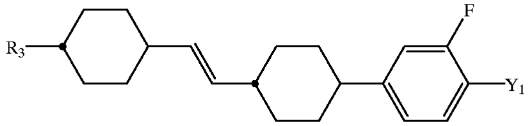
(3-18)
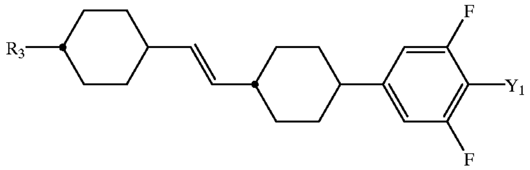
(3-19)
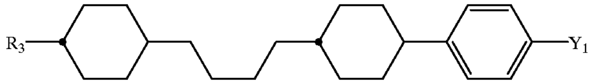
(3-20)
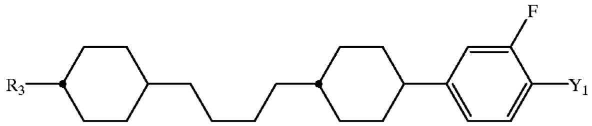
(3-21)
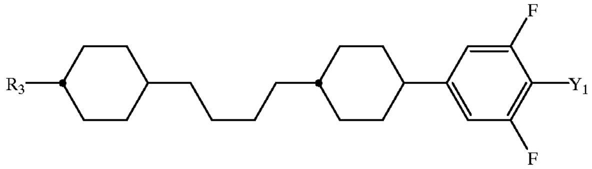

-continued
(3-22)
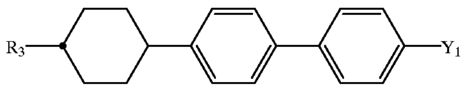
(3-23)
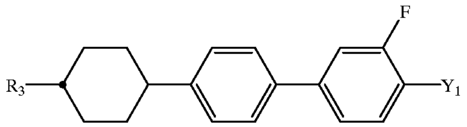
(3-24)
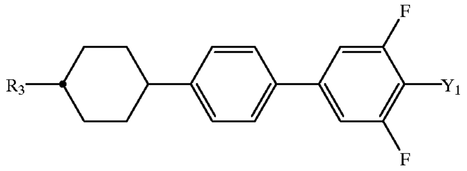
(3-25)
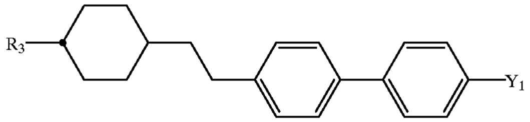
(3-26)
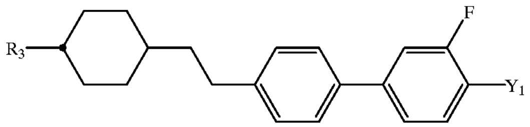
(3-27)
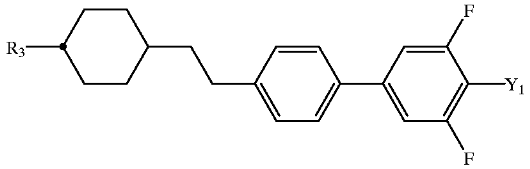
(3-28)
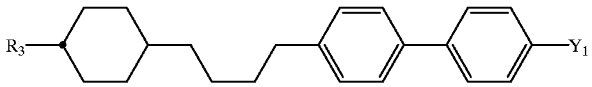
(3-29)
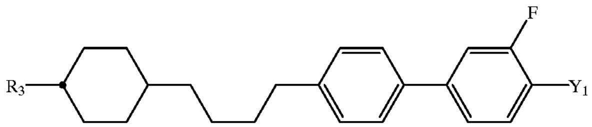
(3-30)
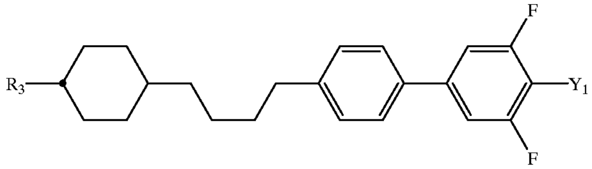
(3-31)
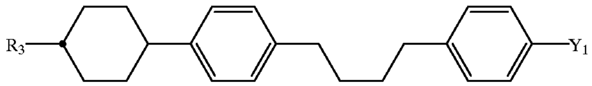

-continued
(3-32)
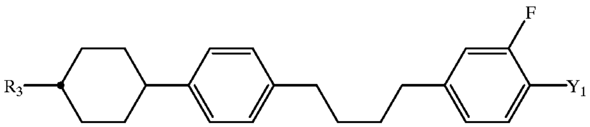
(3-33)
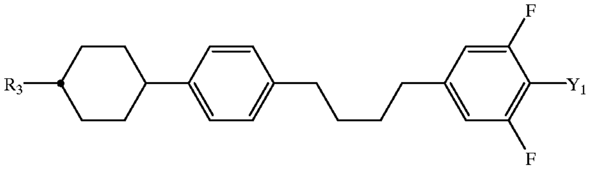
(3-34)
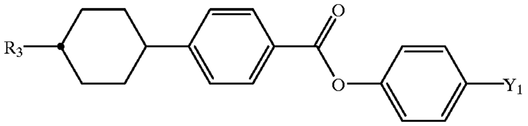
(3-35)
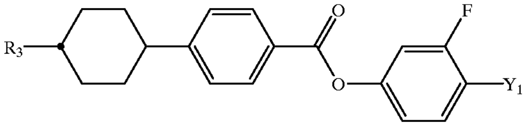
(3-36)
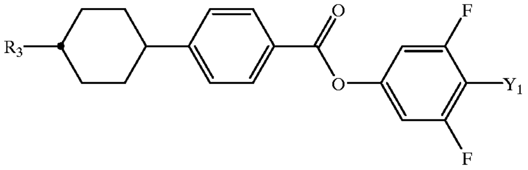
(3-37)
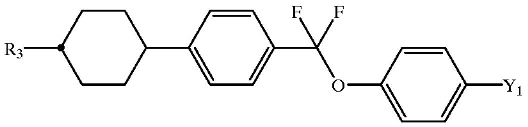
(3-38)
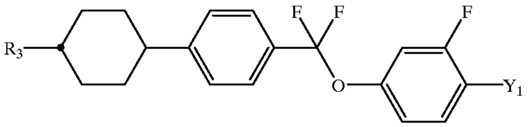
(3-39)
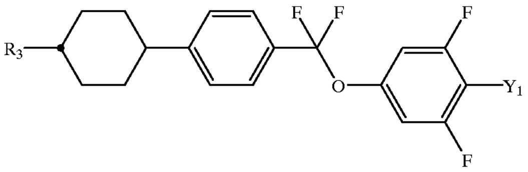
(3-40)
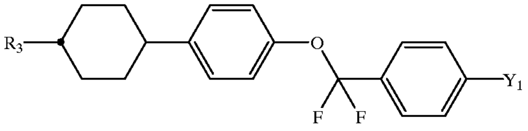
(3-41)
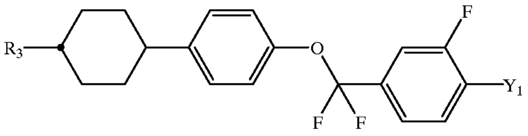

-continued
(3-42)
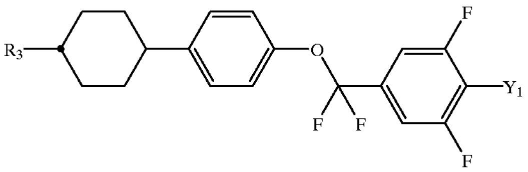
(3-43)
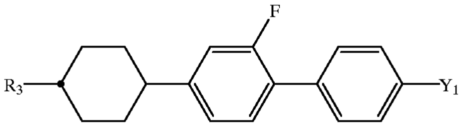
(3-44)
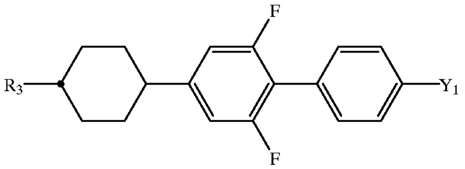
(3-45)
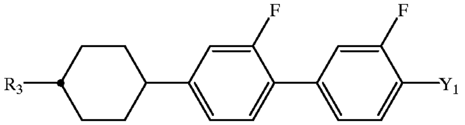
(3-46)
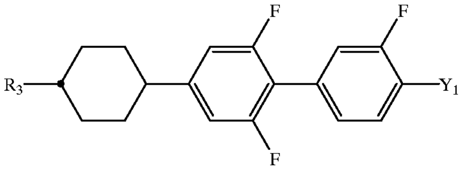
(3-47)
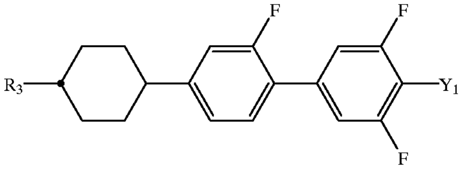
(3-48)
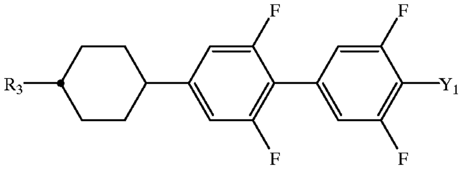
(3-49)
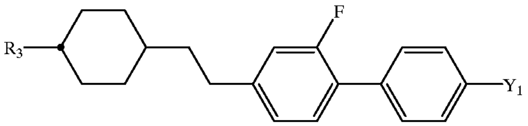
(3-50)
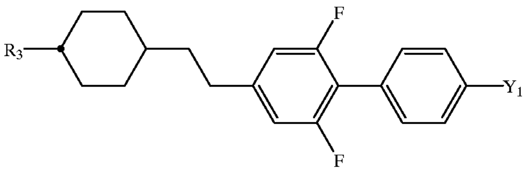

-continued
(3-51)
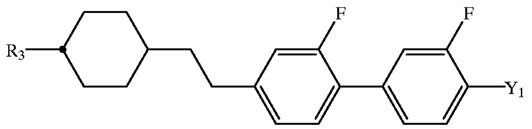
(3-52)
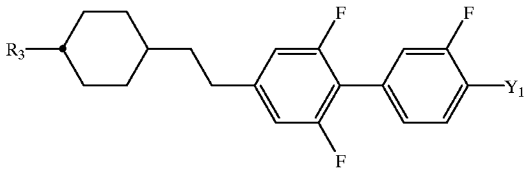
(3-53)
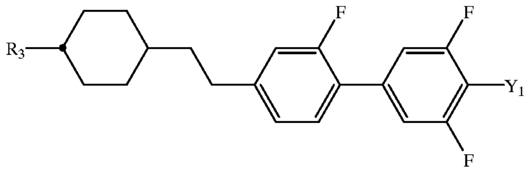
(3-54)
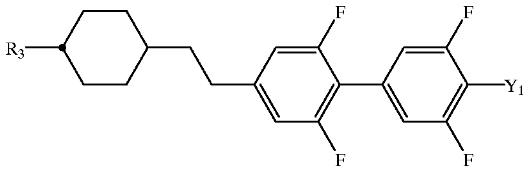
(3-55)
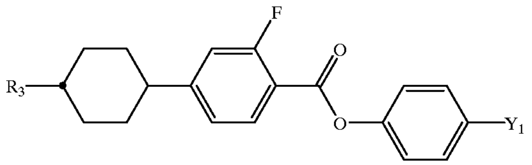
(3-56)
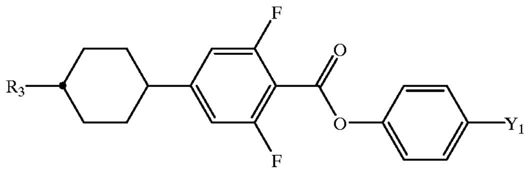
(3-57)
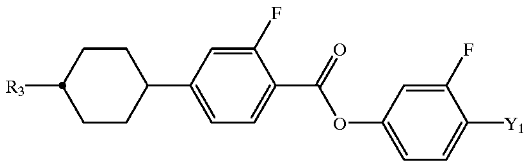
(3-58)
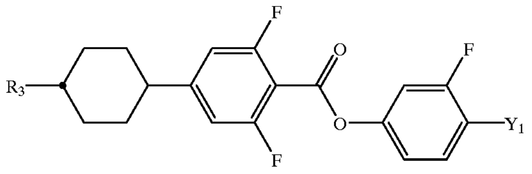

-continued
(3-59)
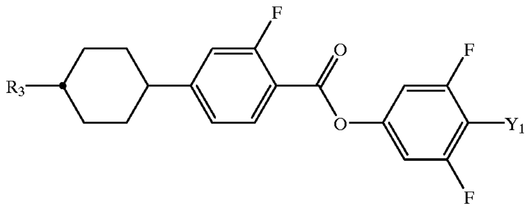
(3-60)
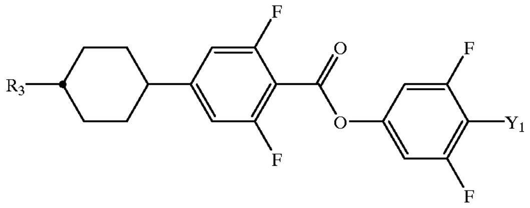
(3-61)
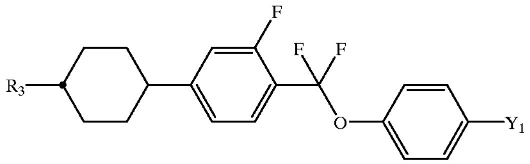
(3-62)
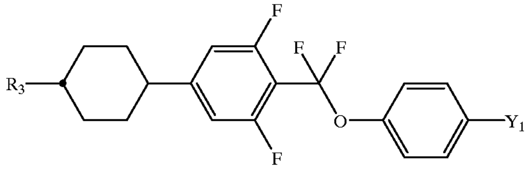
(3-63)
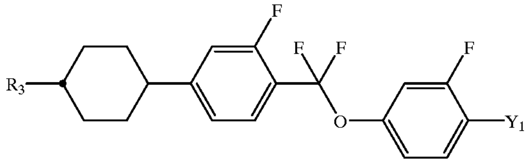
(3-64)
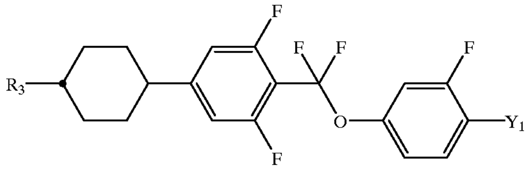
(3-65)
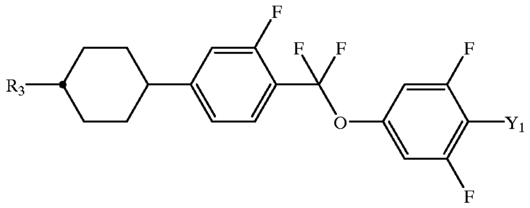

-continued
(3-66)
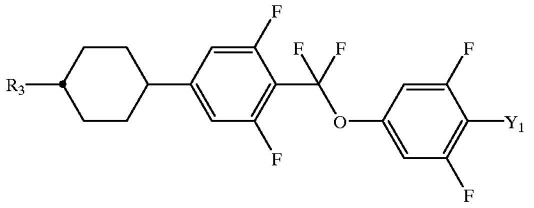
(3-67)
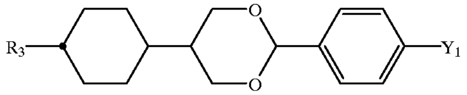
(3-68)
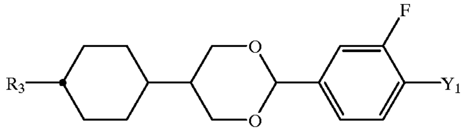
(3-69)
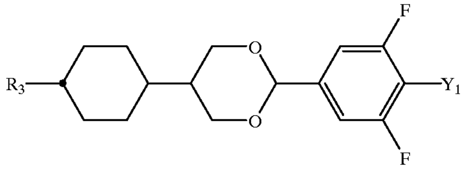
(4-1)
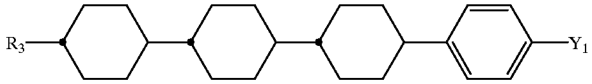
(4-2)
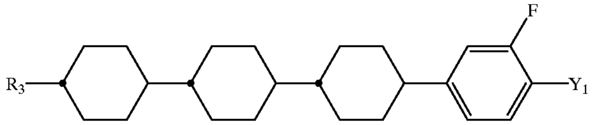
(4-3)
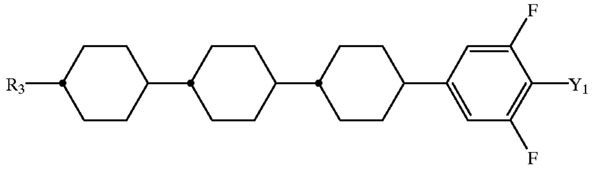
(4-4)
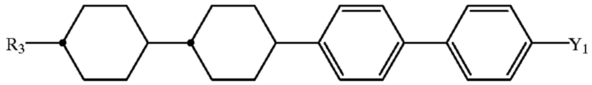
(4-5)
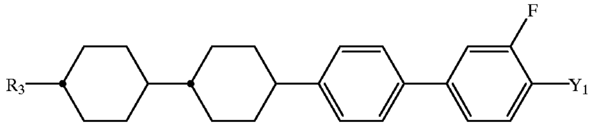
(4-6)
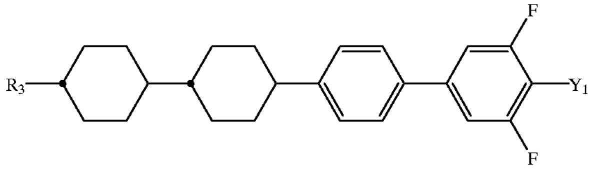

-continued
(4-7)
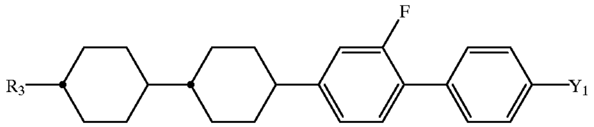
(4-8)
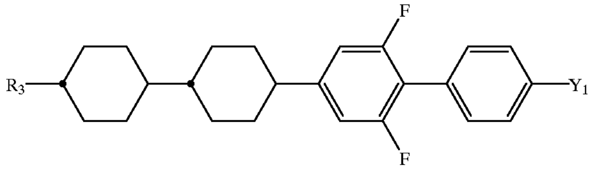
(4-9)
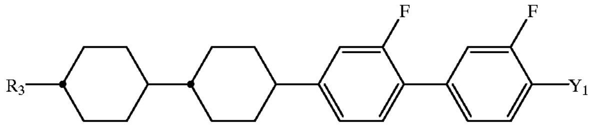
(4-10)
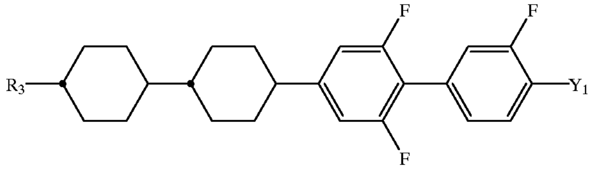
(4-11)
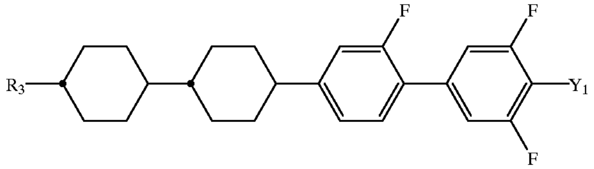
(4-12)
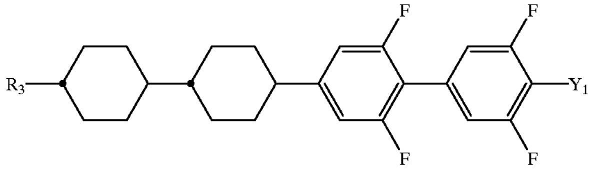
(4-13)
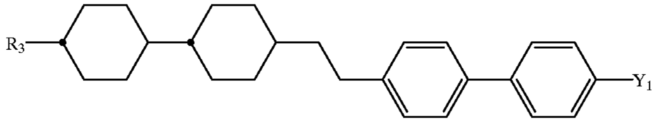
(4-14)
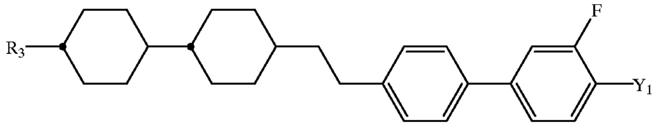
(4-15)
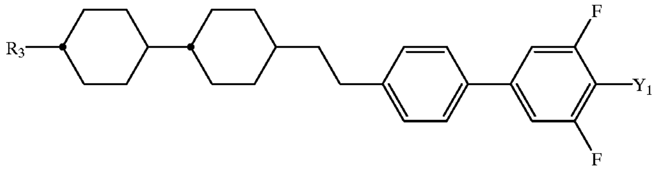

-continued
(4-16)
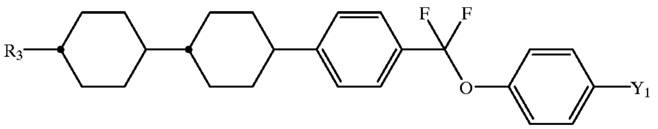
(4-17)
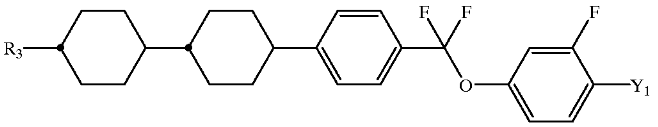
(4-18)
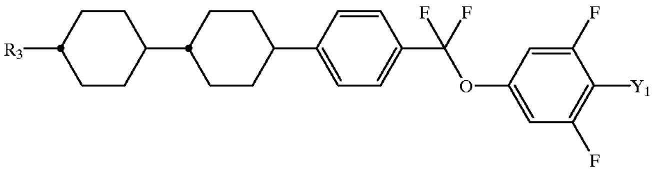
(4-19)
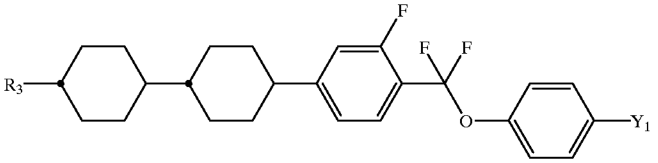
(4-20)
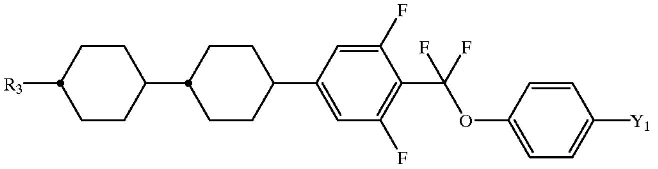
(4-21)
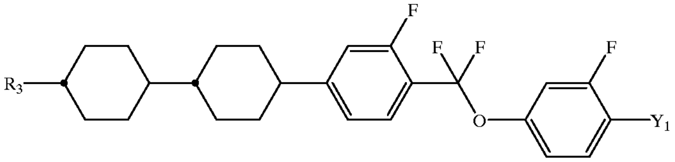
(4-22)
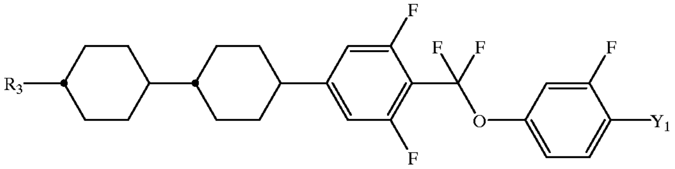
(4-23)
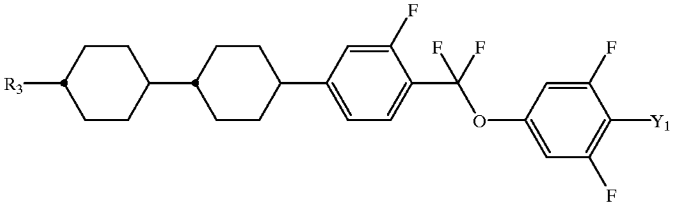

-continued (4-24)

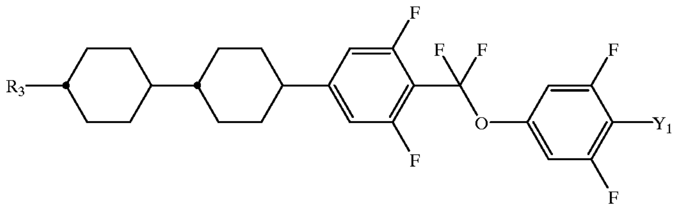

wherein $R_3$ and $Y_1$ have the same meaning as described above.

Compounds expressed by one of the general formulas (2) to (4) are useful when liquid crystal compositions for liquid crystal display devices of which a high reliability is required are produced, since the compounds have a positive dielectric anisotropy, are excellent in thermal stability and chemical stability, and have a high voltage holding ratio. In this case, while the amount of the compound expressed by one of the general formulas (2) to (4) to be used is optional in the range of 1 to 99% by weight based on the total amount of liquid crystal composition, it is preferably 10 to 97% by weight and more desirably 40 to 95% by weight. The liquid crystal compositions may further comprise one or more compounds expressed by one of the general formulas (7) to (9) as necessary. On the other hand, even when liquid crystal compositions for liquid crystal display devices which are driven at a low voltage are produced, the compounds expressed by one of the general formulas (2) to (4) can be used. In this case, however, the amount of the compounds to be used is preferably less than 50% by weight.

As the compounds expressed by the general formula (5) or (6), the compounds of the following general formulas can preferably be mentioned.

(5-1)

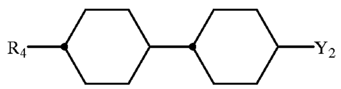

(5-2)

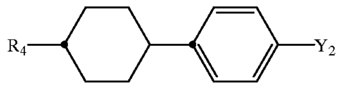

(5-3)

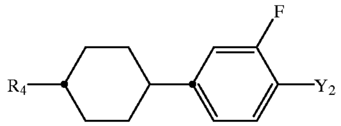

(5-4)

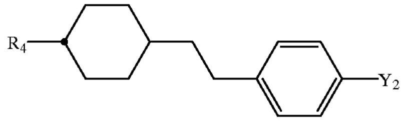

(5-5)

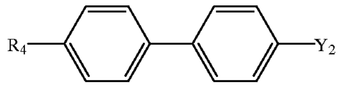

(5-6)

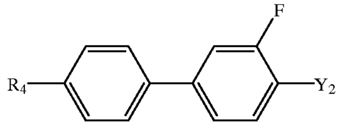

(5-7)

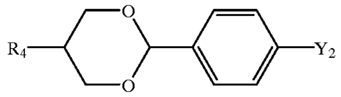

-continued
(5-8)
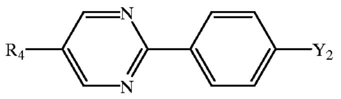
(5-9)
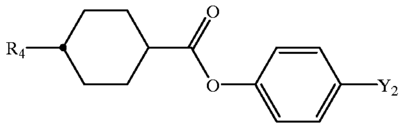
(5-10)
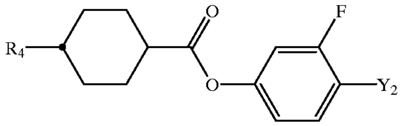
(5-11)
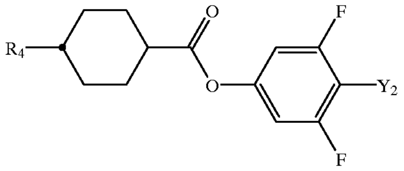
(5-12)
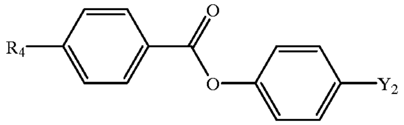
(5-13)
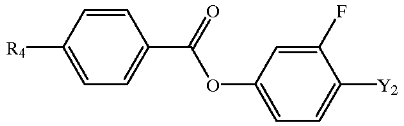
(5-14)
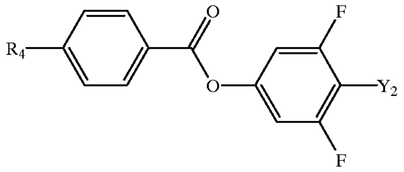
(5-15)
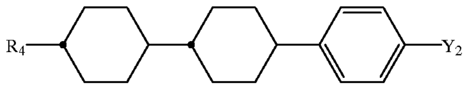
(5-16)
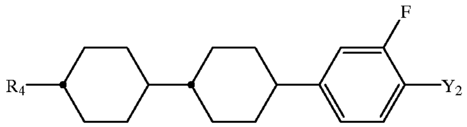
(5-17)
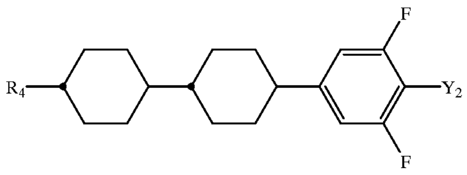

-continued
(5-18)
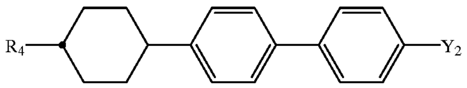
(5-19)
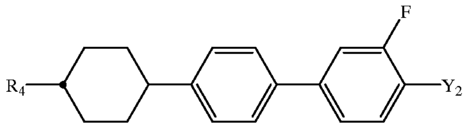
(5-20)
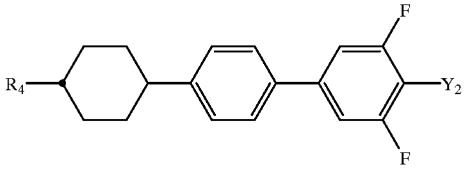
(5-21)
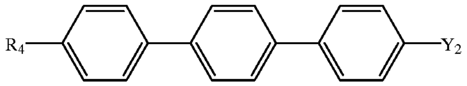
(5-22)
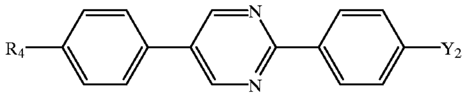
(5-23)
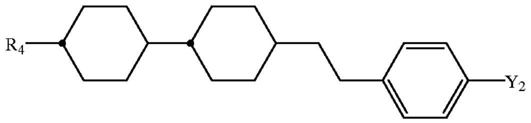
(5-24)
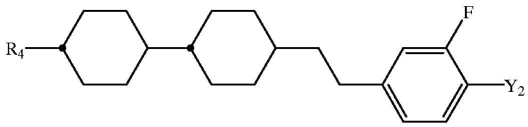
(5-25)
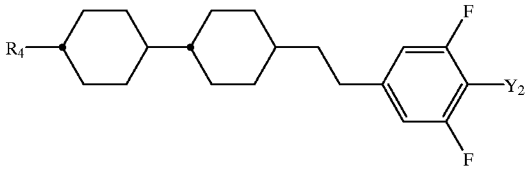
(5-26)
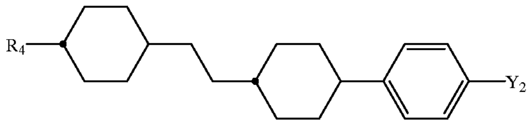
(5-27)
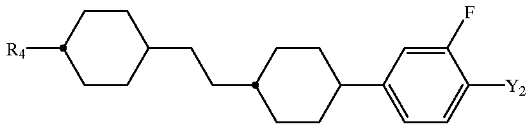

-continued
(5-28)
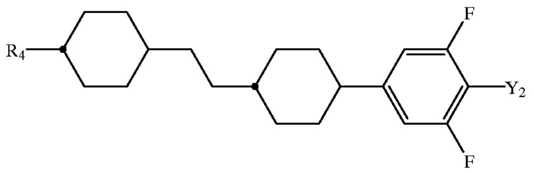
(5-29)
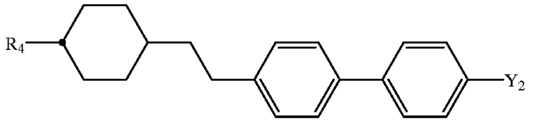
(5-30)
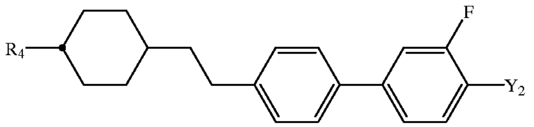
(5-31)
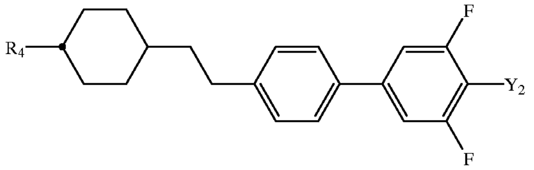
(5-32)
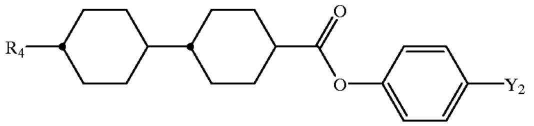
(5-33)
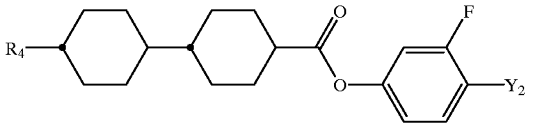
(5-34)
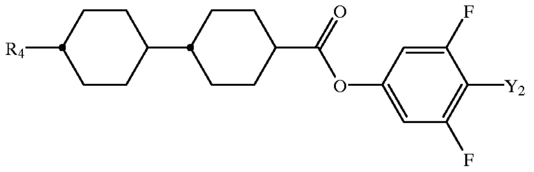
(5-35)
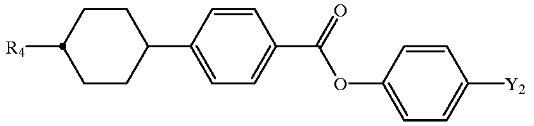
(5-36)
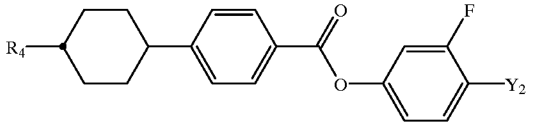

-continued (5-37)

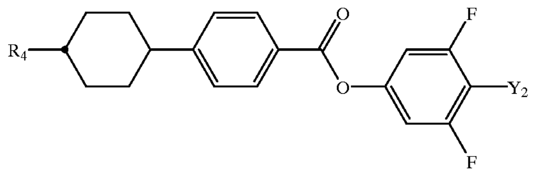

(5-38)

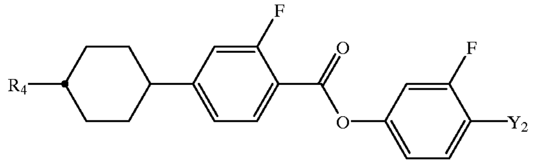

(5-39)

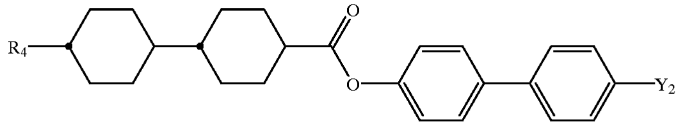

(5-40)

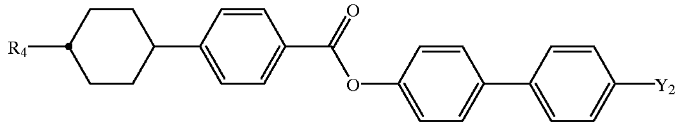

(6-1)

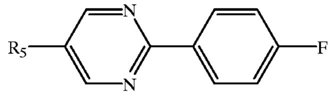

(6-2)

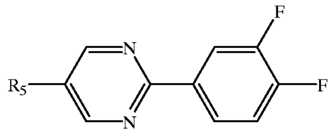

(6-3)

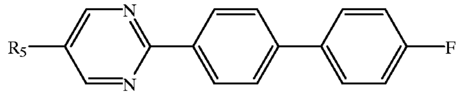

wherein $R_4$, $R_5$, and $Y_2$ have the same meaning as described above.

Compounds expressed by the general formula (5) or (6) have a high positive dielectric anisotropy and are used for the purpose of lowering threshold voltage of liquid crystal compositions. The compounds are used also for the purpose of improving the steepness in the curve of an electrooptical characteristic. In addition, they can also be used for adjusting optical anisotropy and even for the purpose of raising clearing point to expand nematic phase range. Accordingly, the compounds of the general formula (5) or (6) are suitable when liquid crystal compositions for liquid crystal display devices which are driven at a low voltage are produced in particular.

When the amount of the compound of the general formula (5) or (6) actually used is increased, threshold voltage of liquid crystal compositions becomes lower. Accordingly, it is advantageous to use a large amount of the compounds so far as physical properties such as viscosity of liquid crystal compositions are satisfied. While the compounds of the general formula (5) or (6) can be used in an optional amount in the range of 0.1 to 99.9% by weight based on the total amount of liquid crystal composition in this case, the amount is preferably 10 to 97% by weight and more desirably 40 to 95% by weight.

As the compounds expressed by one of the general formulas (7) to (9), the compounds of the following general formulas can be mentioned.

(7-1)
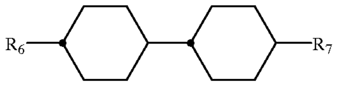
(7-2)
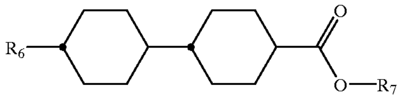
(7-3)
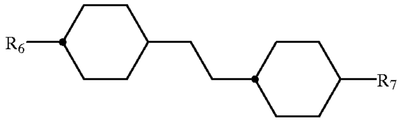
(7-4)
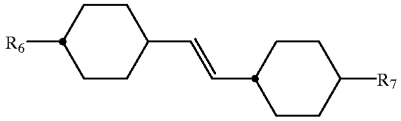
(7-5)
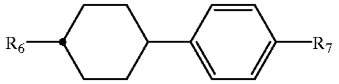
(7-6)
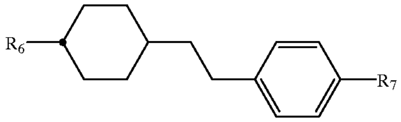
(7-7)
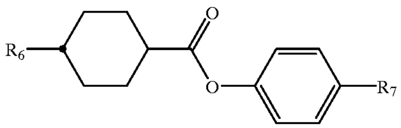
(7-8)
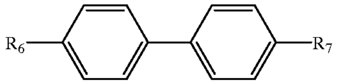
(7-9)
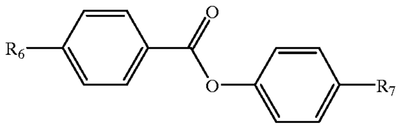
(7-10)
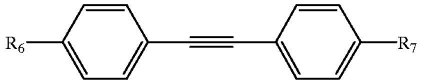
(7-11)
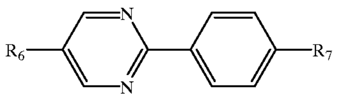
(8-1)
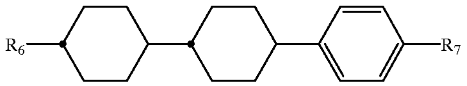

-continued
(8-2)
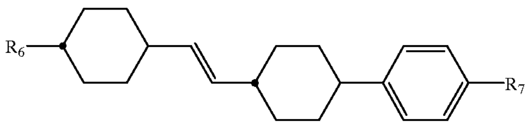
(8-3)
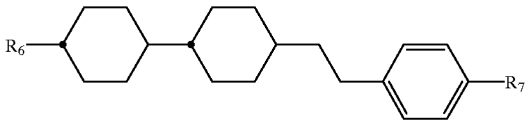
(8-4)
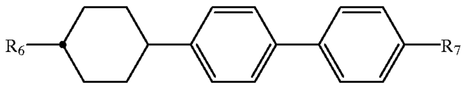
(8-5)
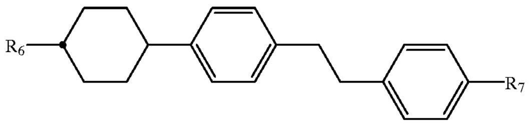
(8-6)
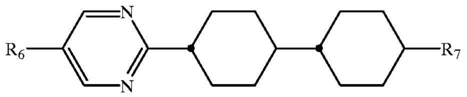
(8-7)
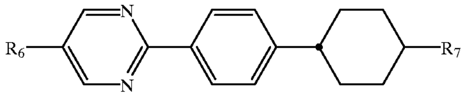
(8-8)
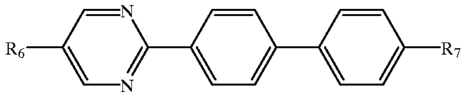
(8-9)
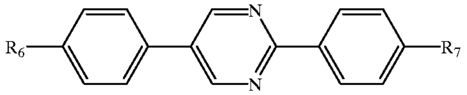
(8-10)
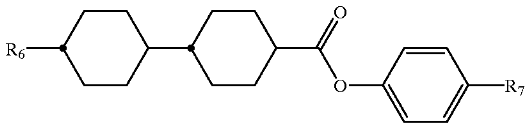
(8-11)
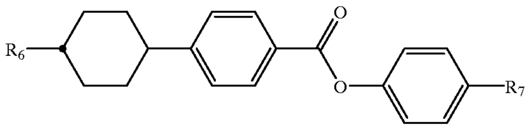
(8-12)
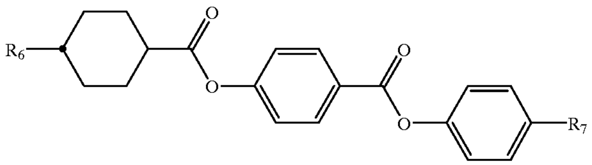

-continued
(8-13)
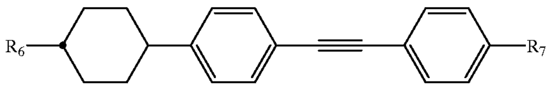
(8-14)
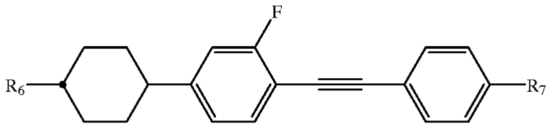
(8-15)
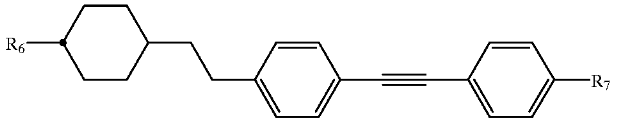
(8-16)
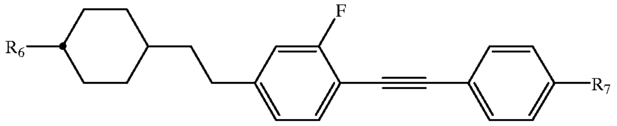
(8-17)
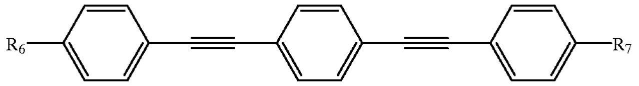
(8-18)
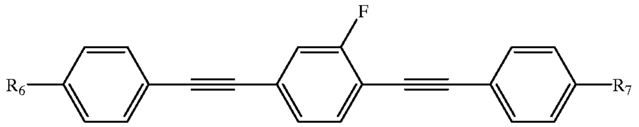
(9-1)
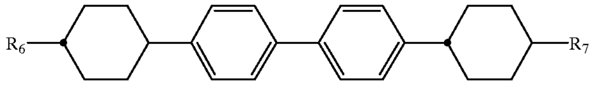
(9-2)
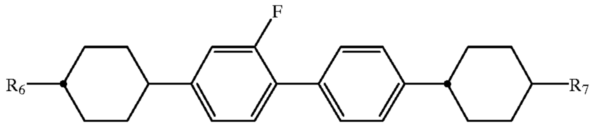
(9-3)
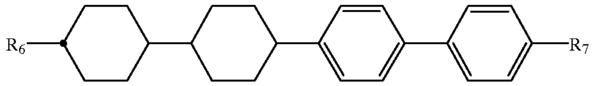
(9-4)
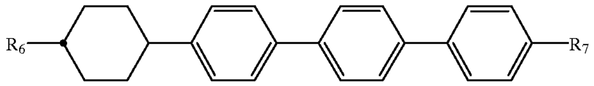
(9-5)
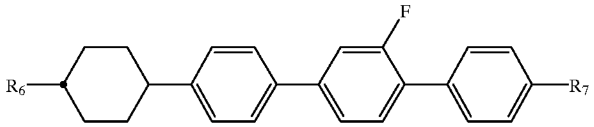

-continued (9-6)

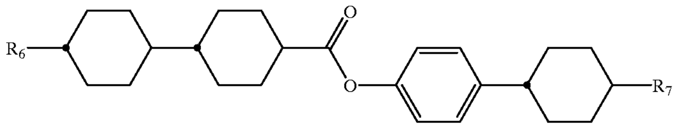

wherein $R_6$ and $R_7$ have the same meaning as described above.

Compounds expressed by one of the general formulas (7) to (9) have a small absolute value of dielectric anisotropy. Compounds of the general formula (7) are used principally for the purpose of adjusting viscosity and optical anisotropy. On the other hand, the compounds of the general formula (8) or (9) are used for the purpose of raising clearing point to expand nematic phase range, or for the purpose of adjusting optical anisotropy.

As the amount of the compounds expressed by one of the general formulas (7) to (9) actually used is increased, threshold voltage of liquid crystal compositions rises and viscosity lowers. Accordingly, the compounds are desirably used in a large amount so far as required threshold voltage of liquid crystal composition is satisfied. When a high reliability is required, the amount of the compounds expressed by one of the general formulas (7) to (9) to be used is preferably less than 40% by weight and more desirably less than 35% by weight. When a low threshold voltage is required, the amount is preferably less than 70% by weight and more desirably less than 60% by weight.

Further, in the liquid crystal compositions of the present invention, an optically active compound may be incorporated for the purpose of inducing helical structure of liquid crystal composition or for the purpose of avoiding the reverse twist. For the purpose of adjusting dependency of the pitch on temperature, two or more kind of optically active compounds may be added to the compositions. While any known compounds may be used as the optically active compound, the following compounds can be mentioned as preferable examples.

[Symbol: C15]

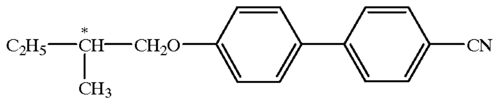

[Symbol: CB15]

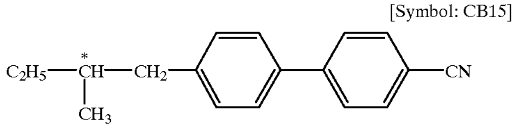

[Symbol: CM21]

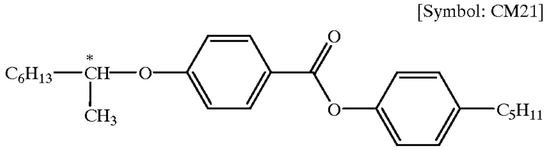

-continued

[Symbol: CM33]

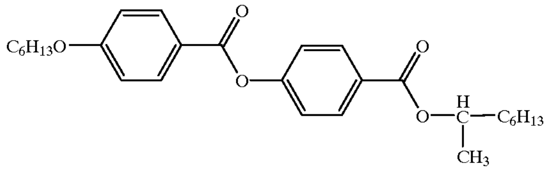

[Symbol: CM44]

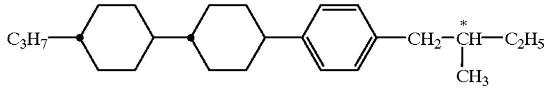

[Symbol: CM45]

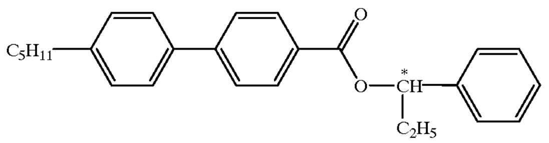

[Symbol: CM47]

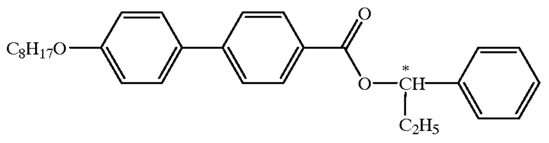

[Symbol: CN]

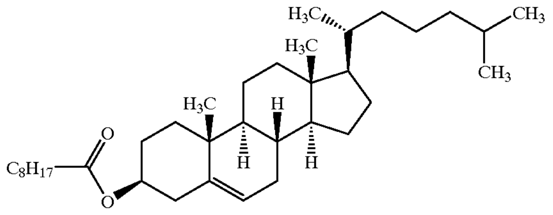

Further, the liquid crystal compositions of the present invention can be used for display devices of either field effect type and current effect type. For instance, the compositions can be used as liquid crystal compositions for devices of guest-host mode by incorporating a dichroic dye such as merocyanine type, styryl type, azo type, azomethine type, azoxy type, quinophthalone type, anthraquinone type, or tetrazine type, in addition to twisted nematic mode, twisted nematic mode combined with active matrix structure, super twisted nematic mode, and electrically controlled birefringence mode. Also, the compositions of the present invention can be used in the application of display devices in which a microcapsulate liquid crystal compositions are dispersed in a polymer or display devices in which a liquid crystal composition exists in a sponge like polymer.

As the nematic liquid crystal compositions comprising the liquid crystalline compound of the present invention, the following Composition Examples (Composition Examples 1 through 34) can be mentioned. In the Compositions Examples, compounds are designated by using abbreviation according to the definition shown in Table 1.

TABLE 1

Method for Designating Compounds by Using Symbols $R-(A_1)-Z_1- \cdots -Z_n-(A_n)-X$

| 1) | Left side terminal group R— | Symbol | 3) | Bonding group $-Z_1-$, $-Z_n-$ | Symbol |
|---|---|---|---|---|---|
| | $C_nH_{2n+1}-$ | n— | | $-C_2H_4-$ | 2 |
| | $C_nH_{2n+1}O-$ | nO— | | $-C_4H_8-$ | 4 |
| | $C_nH_{2n+1}OC_mH_{2m}-$ | nOm— | | —COO— | E |
| | $CH_2=CH-$ | V— | | $-C\equiv C-$ | T |
| | $CH_2=CHC_nH_{2n}-$ | Vn— | | —CH=CH— | V |
| | $C_nH_{2n+1}CH=CHC_mH_{2m}-$ | nVm— | | $-CF_2O-$ | CF2O |
| | $C_nH_{2n+1}CH=CHC_mH_{2m}CH=CHC_kH_{2k}-$ | nVmVk— | | $-OCF_2-$ | OCF2 |

| 2) Ring structure $-(A_1)-$, $-(A_n)-$ | Symbol | | | 4) Right side terminal group —X | Symbol |
|---|---|---|---|---|---|
| 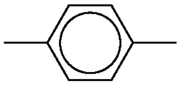 | B | 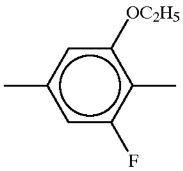 | B(O2,F) | —F | —F |
| 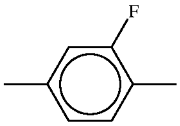 | B(F) | 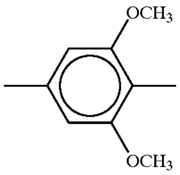 | B (O1,O1) | —Cl | —CL |
| 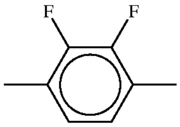 | B(2F,3F) | 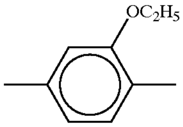 | B(O2) | —CN | —C |
| 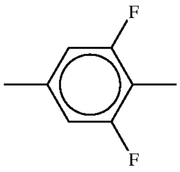 | B(F,F) | | | $-CF_3$ | $-CF_3$ |
| 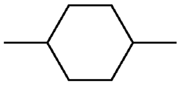 | H | | | $-OCF_3$ | —OCF3 |
| 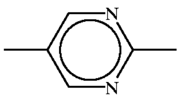 | Py | | | $-OCF_2H$ | —OCF2H |
| 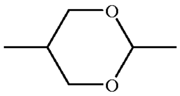 | D | | | $-C_nH_{2n+1}$ | —n |
| 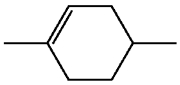 | Ch | | | $-OC_nH_{2n+1}$ | —On |

TABLE 1-continued

Method for Designating Compounds by Using Symbols $R-(A_1)-Z_1- \cdots -Z_n-(A_n)-X$

| | |
|---|---|
| $-COOCH_3$ | —EMe |
| $-C_nH_{2n}CH{=}CH_2$ | —nV |
| $-C_mH_{2m}CH{=}CHC_nH_{2n+1}$ | —mVn |
| $-C_mH_{2m}CH{=}CHC_nH_{2n}F$ | —mVnF |
| $-CH{=}CF_2$ | —VFF |
| $-C_nH_{2n}CH{=}CF_2$ | —nVFF |
| $-C{\equiv}C-CN$ | —TC |

5) Examples of Designation

Example 1 3—H2B(F,F)B(F)—F

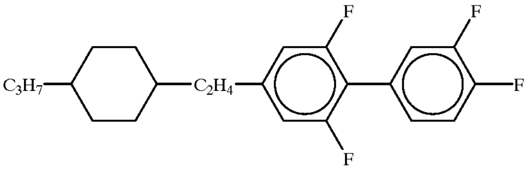

Example 3 1V2-BEB(F,F)—C

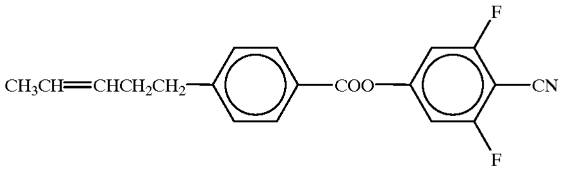

Example 2 3-HB(F)TB-2

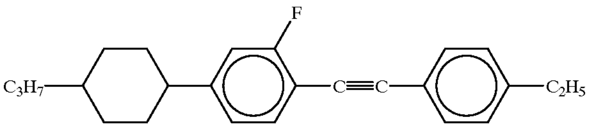

When hydrogen atom of trans-1,4-cyclohexylene group is replaced by heavy hydrogen (deuterium) atom at $Q_4$, $Q_5$, $Q_6$ position in the following partial structural formula, they are designated as H[4D,5D,6D], and when the hydrogen atom is replaced by heavy hydrogen atom at Q8, Q9, and Q10, they are designated as H[8D,9D,10D].

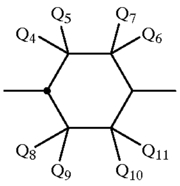

COMPOSITION EXAMPLE 1

| | |
|---|---|
| 3-HHB(O2,F)—F | 3.0% |
| 3-HHB(O1,O1)-F | 3.0% |
| 1V2-BEB(F,F)—C | 5.0% |
| 3-HB—C | 22.0% |
| 1-BTB-3 | 5.0% |
| 2-BTB-1 | 7.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

$T_{NI}$ = 88.1 (° C.)

-continued $\eta$ = 22.6 (mPa · s)
$\Delta n$ = 0.152
$\Delta\epsilon$ = 7.2
$V_{th}$ = 2.07 (V)
P = 11 μm (determined after 0.8% by weight of chiral dopant CM 33 was added to liquid crystal composition)

COMPOSITION EXAMPLE 2

| | |
|---|---|
| 3-HHB(O1,O1)-F | 4.0% |
| 3-HBB(O2,F)—F | 4.0% |
| V2-HB—C | 4.0% |
| 1V2-HB—C | 12.0% |
| 3-HB—C | 15.0% |
| 3-H[1D,2D,3D]—C | 9.0% |
| 3-HB(F)—C | 5.0% |
| 2-BTB-1 | 2.0% |
| 3-HH-4 | 8.0% |
| 3-HH—VFF | 6.0% |
| 2-H[1D,2D,3D]HB—C | 3.0% |
| 3-HHB—C | 6.0% |
| 3-HB(F)TB-2 | 8.0% |
| 3-H2BTB-2 | 5.0% |
| 3-H2BTB-3 | 5.0% |
| 3-H2BTB-4 | 4.0% |

$T_{NI}$ = 83.0 (° C.)
$\eta$ = 27.8 (mPa · s)
$\Delta n$ = 0.144
$\Delta\epsilon$ = 8.9
$V_{th}$ = 1.95 (V)

COMPOSITION EXAMPLE 3

| | |
|---|---|
| 3-HB(F,F)CF2OB(O2)—OCF3 | 4.0% |
| 3-BB(F,F)B(O2)-OCF3 | 4.0% |
| 2O1-BEB(F)—C | 5.0% |
| 3O1-BEB(F)—C | 15.0% |
| 4O1-BEB(F)—C | 13.0% |
| 5O1-BEB(F)—C | 5.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB—O1 | 4.0% |
| $T_{NI}$ = 91.5 (° C.) | |
| η = 89.6 (mPa · s) | |
| Δn = 0.148 | |
| Δε = 30.5 | |
| $V_{th}$ = 0.87 (V) | |

COMPOSITION EXAMPLE 4

| | |
|---|---|
| 3-HHB(O2,F)—F | 5.0% |
| 5-PyB—F | 4.0% |
| 3-PyB(F)—F | 4.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| $T_{NI}$ = 92.9 (° C.) | |
| η = 38.5 (mPa · s) | |
| Δn = 0.193 | |
| Δε = 5.8 | |
| $V_{th}$ = 2.38 (V) | |

COMPOSITION EXAMPLE 5

| | |
|---|---|
| 3-HHB(O1,O1)-F | 5.0% |
| 3-DB—C | 10.0% |
| 4-DB—C | 10.0% |
| 2-BEB—C | 9.0% |
| 3-BEB—C | 4.0% |
| 3-PyB(F)—F | 6.0% |
| 3-HEB—O4 | 6.0% |
| 4-HEB—O2 | 6.0% |
| 5-HEB—O1 | 6.0% |
| 3-HEB—O2 | 5.0% |
| 5-HEB—O2 | 4.0% |
| 5-HEB-5 | 5.0% |
| 4-HEB-5 | 5.0% |
| 1O—BEB-2 | 4.0% |
| 3-HHB-1 | 6.0% |
| 3-HHEBB—C | 3.0% |

-continued

| | |
|---|---|
| 3-HBEBB—C | 3.0% |
| 5-HBEBB—C | 3.0% |
| $T_{NI}$ = 65.1 (° C.) | |
| η = 46.4 (mPa · s) | |
| Δn = 0.113 | |
| Δε = 11.0 | |
| $V_{th}$ = 1.40 (V) | |

COMPOSITION EXAMPLE 6

| | |
|---|---|
| 3-HHB(O2,F)—F | 5.0% |
| 3-HB(F,F)CF2OB(O2)-OCF3 | 5.0% |
| 3-HB—C | 18.0% |
| 7-HB—C | 3.0% |
| 1O1-HB—C | 5.0% |
| 3-HB(F)—C | 5.0% |
| 2-PyB-2 | 2.0% |
| 3-PyB-2 | 2.0% |
| 4-PyB-2 | 2.0% |
| 1O1-HH-3 | 7.0% |
| 2-BTB—O1 | 7.0% |
| 3-HHB-1 | 7.0% |
| 3-HHB—F | 4.0% |
| 3-HHB—O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| $T_{NI}$ = 76.9 (° C.) | |
| η = 24.5 (mPa · s) | |
| Δn = 0.134 | |
| Δε = 7.8 | |
| $V_{th}$ = 1.79 (V) | |

COMPOSITION EXAMPLE 7

| | |
|---|---|
| 3-HHB(O1,O1)-F | 3.0% |
| 3-BB(F,F)B(O2)-OCF3 | 3.0% |
| 2O1-BEB(F)—C | 5.0% |
| 3O1-BEB(F)—C | 12.0% |
| 1V2-BEB(F,F)—C | 10.0% |
| 3-HH-EMe | 10.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F,F)—C | 2.0% |
| 3-HHB—F | 4.0% |
| 3-HHB—O1 | 4.0% |
| 3-HHB-3 | 11.0% |
| 3-HEBEB—F | 2.0% |
| 3-HEBEB-1 | 2.0% |
| $T_{NI}$ = 72.8 (° C.) | |
| η = 41.1 (mPa · s) | |
| Δn = 0.112 | |
| Δε = 23.3 | |
| $V_{th}$ = 1.01 (V) | |

COMPOSITION EXAMPLE 8

| | |
|---|---|
| 3-HBB(O2,F)—F | 5.0% |
| 5-BEB(F)—C | 5.0% |
| V—HB—C | 6.0% |
| 5-PyB—C | 6.0% |
| 4-BB-3 | 11.0% |
| 3-HH-2V | 10.0% |
| 5-HH—V | 11.0% |
| V—HHB-1 | 7.0% |
| V2-HHB-1 | 15.0% |
| 3-HHB-1 | 9.0% |
| 1V2-HBB-2 | 10.0% |
| 3-HHEBH-3 | 5.0% |
| $T_{NI}$ = 88.0 (° C.) | |
| $\eta$ = 19.8 (mPa · s) | |
| $\Delta n$ = 0.110 | |
| $\Delta\epsilon$ = 4.9 | |
| $V_{th}$ = 2.33 (V) | |

COMPOSITION EXAMPLE 9

| | |
|---|---|
| 3-HBB(O2,F)—F | 4.0% |
| 3-BB(F,F)B(O2)-OCF3 | 4.0% |
| 2O1-BEB(F)—C | 5.0% |
| 3O1-BEB(F)—C | 12.0% |
| 1V2-BEB(F,F)—C | 16.0% |
| 3-HB—O2 | 10.0% |
| 3-HH-4 | 3.0% |
| 3-HHB—F | 3.0% |
| 3-HHB-1 | 4.0% |
| 3-HHB—O1 | 4.0% |
| 3-HBEB—F | 4.0% |
| 3-HHEB—F | 7.0% |
| 5-HHEB—F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |
| $T_{NI}$ = 84.8 (° C.) | |
| $\eta$ = 46.8 (mPa · s) | |
| $\Delta n$ = 0.140 | |
| $\Delta\epsilon$ = 28.7 | |
| $V_{th}$ = 0.97 (V) | |

COMPOSITION EXAMPLE 10

| | |
|---|---|
| 3-HHB(O2,F)—F | 3.0% |
| 3-HB(F,F)CF2OB(O2)-OCF3 | 3.0% |
| 2-BEB—C | 12.0% |
| 4-BEB—C | 6.0% |
| 3-HB—C | 28.0% |
| 3-HEB—O4 | 10.0% |
| 4-HEB—O2 | 8.0% |
| 5-HEB—O1 | 8.0% |
| 3-HEB—O2 | 6.0% |
| 5-HEB—O2 | 5.0% |
| 3-HHB-1 | 7.0% |
| 3-HHB—O1 | 4.0% |
| $T_{NI}$ = 66.9 (° C.) | |
| $\eta$ = 29.5 (mPa · s) | |
| $\Delta n$ = 0.106 | |
| $\Delta\epsilon$ = 10.0 | |
| $V_{th}$ = 1.35 (V) | |

COMPOSITION EXAMPLE 11

| | |
|---|---|
| 3-HB(F,F)CF2OB(O2)-OCF3 | 5.0% |
| 2-BEB—C | 10.0% |
| 5-BB—C | 12.0% |
| 7-BB—C | 7.0% |
| 1-BTB-3 | 7.0% |
| 2-BTB-1 | 5.0% |
| 1O—BEB-2 | 10.0% |
| 1O—BEB-5 | 12.0% |
| 2-HHB-1 | 4.0% |
| 3-HHB—F | 4.0% |
| 3-HHB-1 | 7.0% |
| 3-HHB—O1 | 4.0% |
| 3-HHB-3 | 13.0% |
| $T_{NI}$ = 64.5 (° C.) | |
| $\eta$ = 25.0 (mPa · s) | |
| $\Delta n$ = 0.152 | |
| $\Delta\epsilon$ = 7.2 | |
| $V_{th}$ = 1.72 (V) | |

COMPOSITION EXAMPLE 12

| | |
|---|---|
| 3-BB(F,F)B(O2)-OCF3 | 5.0% |
| 1V2-BEB(F,F)—C | 8.0% |
| 3-HB—C | 5.0% |
| V2V—HB—C | 14.0% |
| V2V—HH-3 | 19.0% |
| 3-HB—O2 | 4.0% |
| 3-HHB-1 | 10.0% |
| 3-HHB-3 | 15.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |
| $T_{NI}$ = 98.0 (° C.) | |
| $\eta$ = 22.8 (mPa · s) | |
| $\Delta n$ = 0.131 | |
| $\Delta\epsilon$ = 8.4 | |
| $V_{th}$ = 1.92 (V) | |

COMPOSITION EXAMPLE 13

| | |
|---|---|
| 3-HHB(O2,F)—F | 3.0% |
| 3-HBB(O2,F)—F | 3.0% |
| 5-BTB(F)TB-3 | 10.0% |
| V2-HB—TC | 10.0% |
| 3-HB—TC | 10.0% |
| 3-HB—C | 7.0% |
| 5-HB—C | 7.0% |
| 5-BB—C | 3.0% |
| 2-BTB-1 | 10.0% |
| 2-BTB—O1 | 5.0% |
| 3-HH-4 | 5.0% |
| 3-HHB-1 | 10.0% |
| 3-HHB-3 | 11.0% |
| 3-H2BTB-3 | 3.0% |
| 3-HB(F)TB-2 | 3.0% |
| $T_{NI}$ = 94.2 (° C.) | |
| $\eta$ = 19.6 (mPa · s) | |
| $\Delta n$ = 0.195 | |
| $\Delta\epsilon$ = 7.1 | |
| $V_{th}$ = 2.00 (V) | |

COMPOSITION EXAMPLE 14

| | |
|---|---|
| 3-HHB(O2,F)—F | 3.0% |
| 3-BB(F,F)B(O2)-OCF3 | 3.0% |
| 1V2-BEB(F,F)—C | 4.0% |
| 3-HB—C | 18.0% |
| 2-BTB-1 | 10.0% |
| 5-HH—VFF | 30.0% |
| 1-BHH—VFF | 8.0% |
| 1-BHH-2VFF | 11.0% |
| 3-H2BTB-2 | 5.0% |
| 3-H2BTB-4 | 4.0% |
| 3-HHB-1 | 4.0% |
| $T_{NI}$ = 74.5 (° C.) | |
| η = 17.2 (mPa · s) | |
| Δn = 0.121 | |
| Δε = 6.3 | |
| $V_{th}$ = 2.10 (V) | |

COMPOSITION EXAMPLE 15

| | |
|---|---|
| 3-HHB(O1,O1)-F | 3.0% |
| 3-HB(F,F)CF2OB(O2)-OCF3 | 3.0% |
| 2-HB—C | 5.0% |
| 3-HB—C | 9.0% |
| 3-HB—O2 | 15.0% |
| 2-BTB-1 | 3.0% |
| 3-HHB-1 | 8.0% |
| 3-HHB—F | 4.0% |
| 3-HHB—O1 | 5.0% |
| 3-HHB-3 | 14.0% |
| 3-HHEB—F | 4.0% |
| 5-HHEB—F | 4.0% |
| 2-HHB(F)—F | 7.0% |
| 3-HHB(F)—F | 7.0% |
| 5-HHB(F)—F | 7.0% |
| 3-HHB(F,F)—F | 2.0% |
| $T_{NI}$ = 94.6 (° C.) | |
| η = 24.7 (mPa · s) | |
| Δn = 0.095 | |
| Δε = 4.6 | |
| $V_{th}$ = 2.54 (V) | |

COMPOSITION EXAMPLE 16

| | |
|---|---|
| 3-HHB(O2,F)—F | 3.0% |
| 3-HB(F,F)CF2OB(O2)-OCF3 | 3.0% |
| 2-HHB(F)—F | 17.0% |
| 3-HHB(F)—F | 17.0% |
| 5-HHB(F)—F | 16.0% |
| 2-H2HB(F)—F | 10.0% |
| 3-H2HB(F)—F | 5.0% |
| 5-H2HB(F)—F | 10.0% |
| 3-HBB(F)—F | 6.0% |
| 5-HBB(F)—F | 13.0% |
| $T_{NI}$ = 99.0 (° C.) | |
| η = 28.6 (mPa · s) | |
| Δn = 0.090 | |
| Δε = 5.8 | |
| $V_{th}$ = 2.05 (V) | |
| P = 79 μm (determined after 0.3% by weight of chiral dopant CN was added to liquid crystal composition) | |

COMPOSITION EXAMPLE 17

| | |
|---|---|
| 3-HHB(O2,F)—F | 4.0% |
| 3-HHB(O1,O1)-F | 4.0% |
| 7-HB(F)—F | 5.0% |
| 5-H2B(F)—F | 5.0% |
| 3-HB—O2 | 10.0% |
| 3-HH-4 | 2.0% |
| 3-HH[5D,6D,7D]-4 | 3.0% |
| 2-HHB(F)—F | 10.0% |
| 3-HHB(F)—F | 10.0% |
| 5-HH[5D,6D,7D]B(F)—F | 10.0% |
| 3-H2HB(F) | 5.0% |
| 2-HBB(F)—F | 3.0% |
| 5-HBB(F)—F | 6.0% |
| 3-H2BB(F)—F | 6.0% |
| 3-HHB-1 | 8.0% |
| 3-HHB—O1 | 5.0% |
| 3-HHB-3 | 4.0% |
| $T_{NI}$ = 82.9 (° C.) | |
| η = 27.1 (mPa · s) | |
| Δn = 0.084 | |
| Δε = 3.7 | |
| $V_{th}$ = 2.52 (V) | |

COMPOSITION EXAMPLE 18

| | |
|---|---|
| 3-HBB(O2,F)—F | 5.0% |
| 3-HB(F,F)CF2OB(O2)-OCF3 | 5.0% |
| 7-HB(F,F)—F | 3.0% |
| 3-HB—O2 | 7.0% |
| 2-HHB(F)—F | 10.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| $T_{NI}$ = 78.6 (° C.) | |
| η = 31.2 (mPa · s) | |
| Δn = 0.109 | |
| Δε = 6.6 | |
| $V_{th}$ = 1.94 (V) | |

COMPOSITION EXAMPLE 19

| | |
|---|---|
| 3-HHB(O2,F)—F | 4.0% |
| 3-BB(F,F)B(O2)-OCF3 | 4.0% |
| 7-HB(F,F)—F | 3.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 5.0% |
| 4-HHB(F,F)—F | 5.0% |
| 3-HH2B(F,F)—F | 15.0% |
| 5-HH2B(F,F)—F | 10.0% |
| 3-HBB(F,F)—F | 4.0% |
| 5-HBB(F,F)—F | 12.0% |
| 3-HBCF2OB(F,F)—F | 6.0% |
| $T_{NI}$ = 68.0 (° C.) | |
| η = 32.0 (mPa · s) | |
| Δn = 0.083 | |
| Δε = 9.8 | |
| $V_{th}$ = 1.45 (V) | |

COMPOSITION EXAMPLE 20

| | |
|---|---|
| 3-HHB(O2,F)—F | 5.0% |
| 7-HB(F,F)—F | 5.0% |
| 3-H2HB(F,F)—F | 12.0% |
| 4-H2HB(F,F)—F | 10.0% |
| 3-HHB(F,F)—F | 10.0% |
| 4-HHB(F,F)—F | 5.0% |
| 3-HBB(F,F)—F | 10.0% |
| 3-HHEB(F,F)—F | 10.0% |
| 4-HHEB(F,F)—F | 3.0% |
| 5-HHEB(F,F)—F | 3.0% |
| 2-HBEB(F,F)—F | 3.0% |
| 3-HBEB(F,F)—F | 5.0% |
| 5-HBEB(F,F)—F | 3.0% |
| 3-HDB(F,F)—F | 10.0% |
| 3-HHBB(F,F)—F | 6.0% |
| $T_{NI}$ = 73.5 (° C.) | |
| $\eta$ = 38.2 (mPa · s) | |
| $\Delta n$ = 0.082 | |
| $\Delta\epsilon$ = 13.2 | |
| $V_{th}$ = 1.37 (V) | |

COMPOSITION EXAMPLE 21

| | |
|---|---|
| 3-HHB(O2,F)—F | 5.0% |
| 3-HBB(O2,F)—F | 5.0% |
| 3-BB(F,F)B(O2)-OCF3 | 5.0% |
| 3-HB—CL | 10.0% |
| 5-HB—CL | 4.0% |
| 7-HB—CL | 4.0% |
| 1O1-HH-5 | 5.0% |
| 3-HBB(F)—F | 8.0% |
| 5-HBB(F)—F | 7.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |
| $T_{NI}$ = 80.8 (° C.) | |
| $\eta$ = 31.3 (mPa · s) | |
| $\Delta n$ = 0.120 | |
| $\Delta\epsilon$ = 7.0 | |
| $V_{th}$ = 1.99 (V) | |

COMPOSITION EXAMPLE 22

| | |
|---|---|
| 3-HHB(O1,O1)-F | 5.0% |
| 3-HBB(O2,F)—F | 10.0% |
| 3-HB(F,F)CF2OB(O2)-OCF3 | 5.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-4 | 4.0% |
| 1O1-HBBH-5 | 4.0% |
| $T_{NI}$ = 81.9 (° C.) | |
| $\eta$ = 52.1 (mPa · s) | |
| $\Delta n$ = 0.099 | |
| $\Delta\epsilon$ = 10.2 | |
| $V_{th}$ = 1.62 (V) | |

COMPOSITION EXAMPLE 23

| | |
|---|---|
| 3-HHB(O1,O1)-F | 5.0% |
| 5-HB—F | 12.0% |
| 6-HB—F | 9.0% |
| 7-HB—F | 7.0% |
| 2-HHB—OCF3 | 7.0% |
| 3-HHB—OCF3 | 7.0% |
| 4-HHB—OCF3 | 7.0% |
| 3-HH2B—OCF3 | 4.0% |
| 5-HH2B—OCF3 | 4.0% |
| 3-HHB(F,F)—OCF3 | 5.0% |
| 3-HBB(F)—F | 10.0% |
| 5-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |
| $T_{NI}$ = 79.3 (° C.) | |
| $\eta$ = 22.4 (mPa · s) | |
| $\Delta n$ = 0.088 | |
| $\Delta\epsilon$ = 4.8 | |
| $V_{th}$ = 2.32 (V) | |

COMPOSITION EXAMPLE 24

| | |
|---|---|
| 3-HBB(O2,F)—F | 5.0% |
| 3-BB(F,F)B(O2)-OCF3 | 5.0% |
| 5-H4HB(F,F)—F | 7.0% |
| 5-H4HB—OCF3 | 15.0% |
| 3-H4HB(F,F)—CF3 | 8.0% |
| 5-H4HB(F,F)—CF3 | 5.0% |
| 3-HB—CL | 6.0% |
| 5-HB—CL | 4.0% |
| 3-H2BB(F)—F | 10.0% |
| 5-HVHB(F,F)—F | 5.0% |
| 3-HHB—OCF3 | 5.0% |
| 3-H2HB—OCF3 | 5.0% |
| V—HHB(F)—F | 5.0% |
| 3-HHB(F)—F | 5.0% |
| 5-HHEB—OCF3 | 2.0% |
| 3-HBEB(F,F)—F | 5.0% |
| 5-HH—V2F | 3.0% |
| $T_{NI}$ = 64.4 (° C.) | |
| $\eta$ = 33.2 (mPa · s) | |
| $\Delta n$ = 0.086 | |
| $\Delta\epsilon$ = 9.4 | |
| $V_{th}$ = 1.62 (V) | |

COMPOSITION EXAMPLE 25

| | |
|---|---|
| 3-HBB(O2,F)—F | 5.0% |
| 3-HB(F,F)CF2OB(O2)-OCF3 | 5.0% |
| 3-BB(F,F)B(O2)-OCF3 | 5.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 10.0% |
| 5-HBB(F,F)—F | 19.0% |
| 1O1-HBBH-4 | 5.0% |
| 1O1-HBBH-5 | 5.0% |
| $T_{NI}$ = 85.8 (° C.) | |
| $\eta$ = 46.8 (mPa · s) | |

-continued

| | |
|---|---|
| Δn = 0.128 | |
| Δϵ = 8.7 | |
| $V_{th}$ = 1.76 (V) | |

COMPOSITION EXAMPLE 26

| | |
|---|---|
| 3-HB(F,F)CF2OB(O2)-OCF3 | 5.0% |
| 5-HB—CL | 12.0% |
| 3-HH-4 | 7.0% |
| 3-HB—O2 | 20.0% |
| 3-H2HB(F,F)—F | 3.0% |
| 3-HHB(F,F)—F | 8.0% |
| 3-HBB(F,F)—F | 6.0% |
| 2-HHB(F)—F | 5.0% |
| 3-HHB(F)—F | 5.0% |
| 5-HHB(F)—F | 5.0% |
| 2-H2HB(F)—F | 2.0% |
| 3-H2HB(F)—F | 1.0% |
| 5-H2HB(F)—F | 2.0% |
| 3-HHBB(F,F)—F | 4.0% |
| 3-HBCF2OB—OCF3 | 4.0% |
| 5-HBCF2OB(F,F)—CF3 | 4.0% |
| 3-HHB-1 | 3.0% |
| 3-HHB—O1 | 4.0% |
| $T_{NI}$ = 67.3 (° C.) | |
| η = 18.1 (mPa · s) | |
| Δn = 0.084 | |
| Δϵ = 4.7 | |
| $V_{th}$ = 2.06 (V) | |

COMPOSITION EXAMPLE 27

| | |
|---|---|
| 3-BCF2OB(O2,F)—CF3 | 5.0% |
| 3-HHB(O2,F)—F | 4.0% |
| 3-BEB(F)—C | 8.0% |
| 3-HB—C | 4.0% |
| V—HB—C | 8.0% |
| 1V—HB—C | 8.0% |
| 3-HB—O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB—F | 7.0% |
| 3-H2BTB-2 | 6.0% |
| 3-H2BTB-3 | 6.0% |

COMPOSITION EXAMPLE 28

| | |
|---|---|
| 3-BCF2OB(O2,F)—CF3 | 5.0% |
| 3-HHB(O1,O1)-F | 5.0% |
| 3-H2HB(F,F)—F | 7.0% |
| 5-H2HB(F,F)—F | 8.0% |
| 3-HHB(F,F)—F | 10.0% |
| 4-HHB(F,F)—F | 5.0% |
| 3-HH2B(F,F)—F | 9.0% |
| 5-HH2B(F,F)—F | 9.0% |
| 3-HBB(F,F)—F | 5.0% |
| 5-HBB(F,F)—F | 15.0% |
| 3-HBEB(F,F)—F | 2.0% |
| 4-HBEB(F,F)—F | 2.0% |
| 5-HBEB(F,F)—F | 2.0% |
| 3-HHEB(F,F)—F | 10.0% |

-continued

| | |
|---|---|
| 4-HHEB(F,F)—F | 3.0% |
| 5-HHEB(F,F)—F | 3.0% |

COMPOSITION EXAMPLE 29

| | |
|---|---|
| 3-HB(O2)-OCF3 | 3.0% |
| 3-HBB(O2,F)—F | 4.0% |
| 3-HB(F,F)CF2OB(O1,O1)B(F,F)—F | 3.0% |
| 5-BTB(F)TB-3 | 10.0% |
| V2-HB—TC | 10.0% |
| 3-HB—TC | 10.0% |
| 3-HB—C | 10.0% |
| 5-HB—C | 7.0% |
| 5-BB—C | 3.0% |
| 2-BTB-1 | 10.0% |
| 2-BTB—O1 | 5.0% |
| 3-HH-4 | 5.0% |
| 3-HHB-3 | 11.0% |
| 3-H2BTB-2 | 3.0% |
| 3-H2BTB-3 | 3.0% |
| 3-HB(F)TB-2 | 3.0% |

COMPOSITION EXAMPLE 30

| | |
|---|---|
| 3-HEB(O2,F)—F | 4.0% |
| 3-HHB(F)B(O2,F)—CF3 | 4.0% |
| 1V2-BEB(F,F)—C | 6.0% |
| 3-HB—C | 10.0% |
| 2-BTB-1 | 10.0% |
| 5-HH—VFF | 30.0% |
| 1-BHH—VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

COMPOSITION EXAMPLE 31

| | |
|---|---|
| 3-HEB(O2,F)—F | 5.0% |
| 3-HB(O1,O1)-OCF3 | 5.0% |
| 3-HHB(O1,O1)-F | 10.0% |
| 3-HBB(O2,F)—F | 5.0% |
| 3-HHB(F)B(O2,F)—CF3 | 5.0% |
| 3-HB(F)B(O2)B(F)—C | 5.0% |
| 2-HB—C | 4.0% |
| 3-HB—C | 12.0% |
| 3-HB—O2 | 15.0% |
| 2-BTB-1 | 3.0% |
| 3-HHB-1 | 8.0% |
| 3-HHB—F | 4.0% |
| 3-HHB—O1 | 5.0% |
| 3-HHB-3 | 14.0% |

COMPOSITION EXAMPLE 32

| | |
|---|---|
| 4-HB(O2)-OCF3 | 10.0% |
| 3-HEB(O2,F)-F | 5.0% |
| 3-HHB(O2,F)-F | 5.0% |
| 3-HHB(O1,O1)-F | 10.0% |

-continued

| | |
|---|---|
| 3-HHB(F)B(O2,F)-CF3 | 5.0% |
| 3-HB(F,F)CF2OB(O1,O1)B(F,F)-F | 5.0% |
| 3-HHB(F,F)-F | 9.0% |
| 3-H2HB(F,F)-F | 8.0% |
| 5-H2HB(F,F)-F | 8.0% |
| 3-HBB(F,F)-F | 17.0% |
| 3-H2BB(F,F)-F | 10.0% |
| 1O1-HBBH-4 | 4.0% |
| 1O1-HBBH-5 | 4.0% |

COMPOSITION EXAMPLE 33

| | |
|---|---|
| 3-HEB(O2,F)-F | 5.0% |
| 3-HB(F)B(O2)B(F)-C | 5.0% |
| 5-HB-F | 12.0% |
| 6-HB-F | 9.0% |
| 7-HB-F | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HBB(F)-F | 7.0% |
| 5-HBB(F)-F | 10.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

COMPOSITION EXAMPLE 34

| | |
|---|---|
| 3-HB(O1,O1)-OCF3 | 4.0% |
| 3-HHB(F)B(O2,F)-CF3 | 4.0% |
| 5-H4HB(F,F)-F | 7.0% |
| 5-H4HB-OCF3 | 15.0% |
| 5-H4HB(F,F)-CF3 | 10.0% |
| 3-HB-CL | 6.0% |
| 5-HB-CL | 4.0% |
| 2-H2BB(F)-F | 5.0% |
| 3-H2BB(F)-F | 10.0% |
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F,F)-F | 5.0% |
| 5-HH-V2F | 3.0% |

Compounds of the present invention expressed by the general formula (1) can be produced by using ordinary procedures in organic synthetic chemistry in combination. For instance, it is sufficient to select, and use the methods described in Organic Synthesis (John Wiley & Sons, Inc.), Organic Reactions (John Wiley & Sons, Inc.), or Jikken Kagaku Kouza (Course of Chemical Experiment) (Maruzen Co., Ltd.) in a suitable combination.

When compounds of the formula (1-a) which are expressed by the general formula (1) wherein ring $A_1$ is 1,4-phenylene group and $Z_1$ is single bond are produced, first, a derivative of 3-fluorobromobenzene of the formula (15) is reacted with an alcohol in the presence of a base such as sodium hydroxide and potassium hydroxide at a temperature of 50 to 100° C. to obtain a compound of the formula (16) in which fluorine atom at position 3 is replaced by nucleophilic reaction. In the case where $Q_3$ is fluorine atom, a minor amount of 3,5-difluoro-substituted compound is produced. In this case, however, the object compound can be separated through the purification by silica gel chromatography. The compounds of the formula (16) thus obtained are subjected to a coupling reaction with a boric acid derivative of the formula (17) prepared by the method described in Org. Synth., IV, 68 (1963), in the presence of a palladium catalyst such as tetrakistriphenylphosphine palladium (0) to produce an object compound of the formula (1-a).

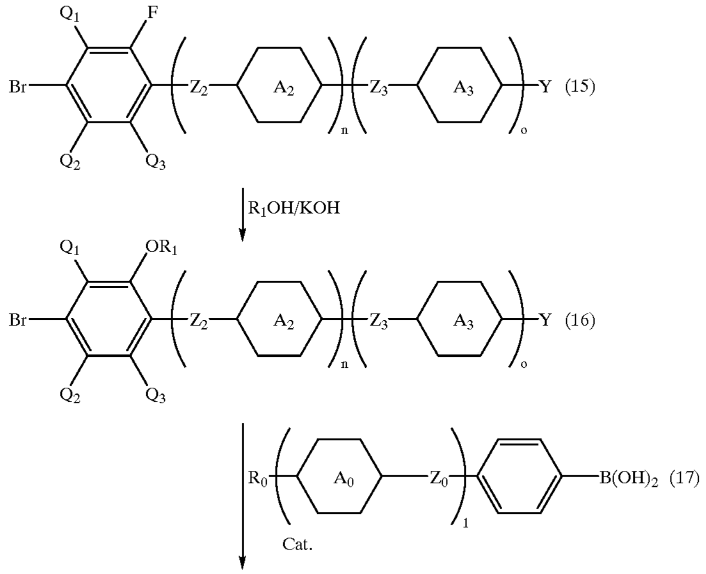

-continued

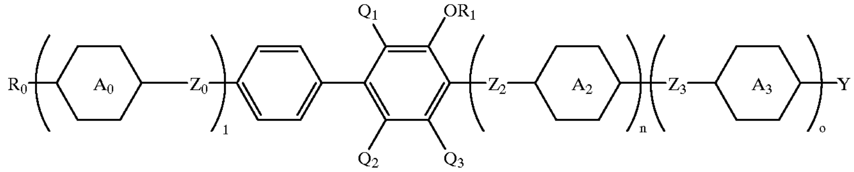

(1-a)

wherein $R_0$, $R_1$, ring $A_0$, ring $A_2$, ring $A_3$, $Z_0$, $Z_2$, $Z_3$, l, n, o, $Q_1$, $Q_2$, $Q_3$, and Y have the same meaning as described above.

Compounds of the formula (1-b) which are expressed by the general formula (1) wherein ring $A_1$ is 1,4-cyclohexylene group, and $Z_1$ is single bond can be produced by the following method. That is, the Grignard reagent prepared from the compound of the formula (16) described above is reacted with a derivative of cyclohexanone of the formula (18) to produce a derivative of cyclohexanol of the formula (19). When preparation of the Grignard reagent is difficult, a compound of the formula (16) is reacted with an alkyl lithium such as butyl lithium to lithiate, and then reacted with a compound of the formula (18) to produce a compound of the formula (19). Subsequently, the compound of the formula (19) is subjected to a dehydration reaction in the presence of an inorganic acid such as hydrochloric acid and sulfuric acid, an organic acid such as p-toluenesulfinic acid and p-toluenesulfonic acid, or an acid catalyst such as an acidic ion exchange resin to form a cyclohexene derivative, and then subjecting the derivative to a catalytic hydrogen reduction using palladium carbon or Raney nickel as catalyst to obtain an object compound of the formula (1-b).

wherein $R_0$, $R_1$, ring $A_0$, ring $A_2$, ring $A_3$, $Z_0$, $Z_2$, $Z_3$, l, n, o, $Q_1$, $Q_2$, $Q_3$, and y have the same meaning as described above, and R' represents an alkyl group or isoalkyl group.

While the compounds of the formula (1-c) expressed by the general formula (1) wherein $A_1$ is 1,4-phenylene group, and $Z_1$ is difluoromethylenoxy group (—$CF_2O$—) can be produced according to the method described in Laid-open Japanese Patent Publication No. Hei 2-289529 or Laid-open Japanese Patent Publication No. Hei 5-112778, they can readily be produced even by the following method. That is, according to the method of R. L. Kidwellt et al., (Org. Synth., V, 918 (1973)), a Grignard reagent prepared from a compound of the formula (16) is reacted with a trialkyl borate to prepare a derivative of boric acid ester of the formula (20). Subsequently, it is oxidized with peracetic acid to produce a phenol derivative of the formula (21). When preparation of the Grignard reagent is difficult, it is lithiated with an alkyl lithium and then reacted with a trialkyl borate to produce a compound of the formula (20). Subsequently, according to the method described in Chem. Ber., 98, 838 (1965), a phenol derivative of the formula (21) is reacted with a thioncarboxylic acid chloride of the formula (22)

(16)

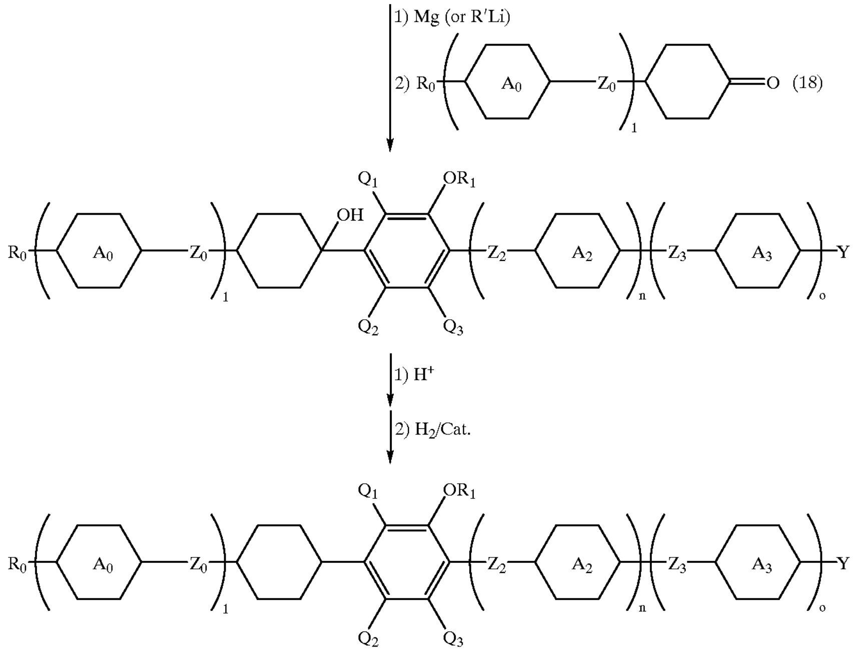

(18)

(19)

(1-b)

prepared by the method described in J. Am. Chem. Soc., 50, 3106 (1928) and Helv. Chim. Acta., 3, 824 (1920), in the presence of a base such as pyridine to produce a thion-O-ester derivative of the formula (23). The compound of the formula (23) is reacted with diethylaminosulfur trifluoride (hereinafter abbreviated as DAST), or reacted with quaternary ammonium dihydrogentrifluoride in the presence of n-bromosuccinimide according to the method described in Laid-open Japanese Patent Publication No. Hei 5-255165 to produce an object compound of the formula (1-c).

wherein $R_0$, $R_1$, ring $A_0$, ring $A_2$, ring $A_3$, $Z_0$, $Z_2$, $Z_3$, l, n, o, $Q_1$, $Q_2$, $Q_3$, and Y have the same meaning as described above, and R' and R" represent an alkyl group or isoalkyl group.

Compounds of the formula (1-d) which are expressed by the general formula (1) wherein $Z_1$ is methylenoxy group are produced by reacting a phenol derivative of the formula (21) with sodium hydride in a dipolar aprotic solvent such as dimethyl formamide (DMF) to convert into a phenolate and then reacting the phenolate with a bromide of the formula (24).

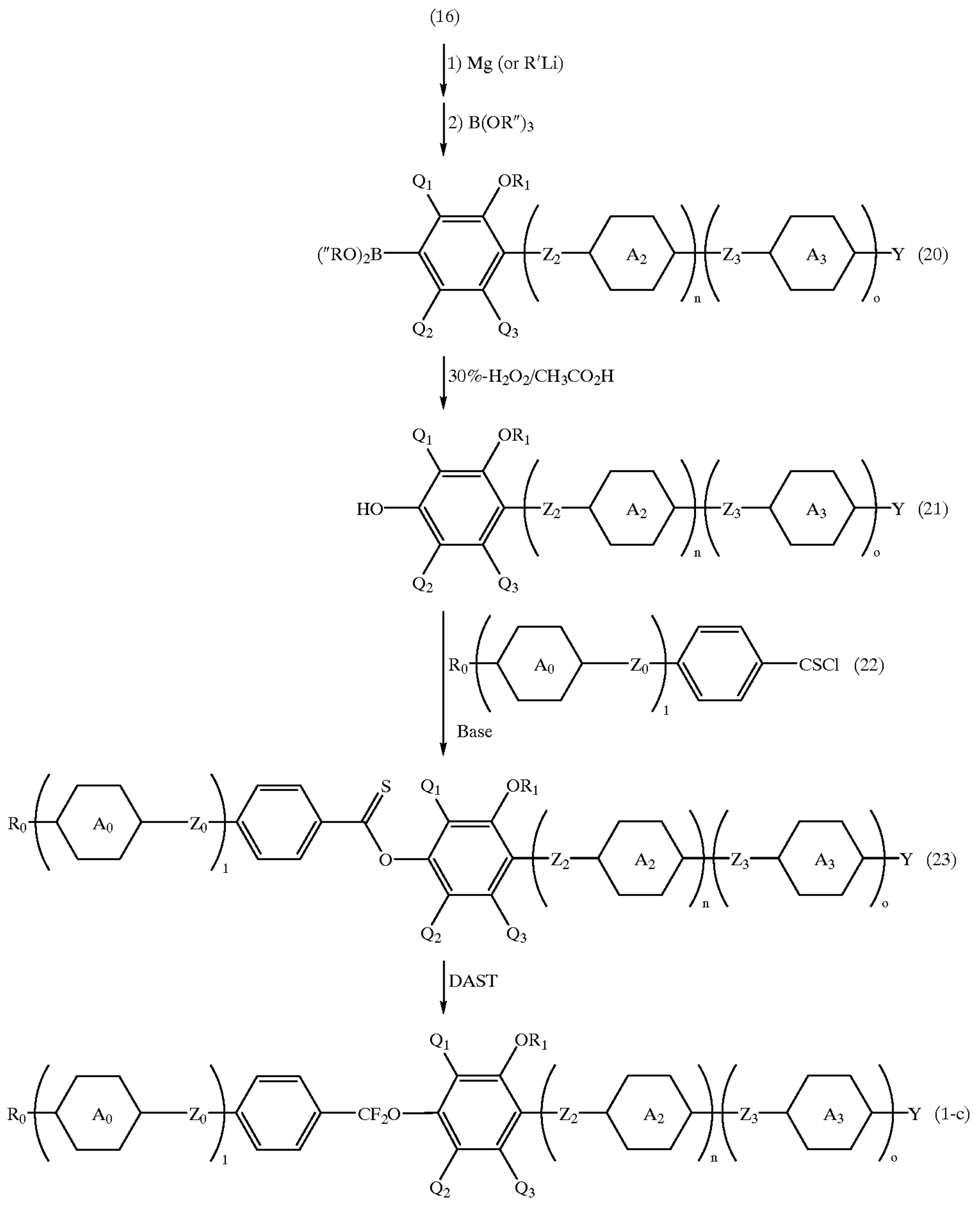

(21)

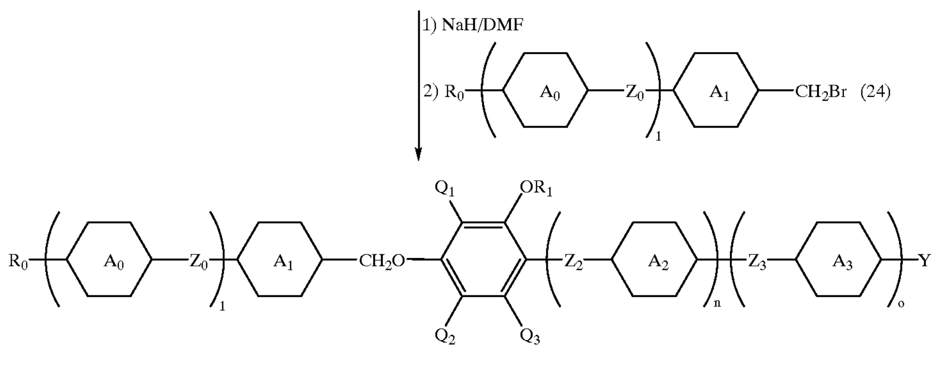

(24)

(1-d)

wherein $R_0$, $R_1$, ring $A_0$, ring $A_1$, ring $A_2$, ring $A_3$, $Z_0$, $Z_2$, $Z_3$, l, n, o, $Q_1$, $Q_2$, $Q_3$, and Y have the same meaning as described above.

Compounds of the formula (28) which are expressed by the general formula (1) wherein $Q_3$ is —$OR_1$ or —$OR_2$ are produced by the method as follows. That is, a 3,5-difluorobromobenzene derivative of the formula (25) is reacted with a sodium alkoxide prepared from an alcohol ($R_1OH$) in a dipolar aprotic solvent such as DMF at a temperature of 50 to 100° C. to produce a dialkoxy-substituted compound of the formula (26). At the time of this reaction, a small amount of a monoalkoxy-substituted compound is formed, but it can be removed by silica gel column chromatography.

Also, compounds of the formula (28) in which $Q_3$ is $OR_1$ group or $OR_2$ group can be produced by first preparing a compound having an alkoxy group of the formula (27) from a 3,5-difluorobromobenzene derivative of the formula (25) according to the procedures in which a compound of the formula (16) is derived from the 3-fluorobromobenzene derivative of the formula (15) described above, and then reacting the compound of the formula (27) with a sodium alkoxide ($R_2ONa$) in an aprotic solvent in the same manner as described above.

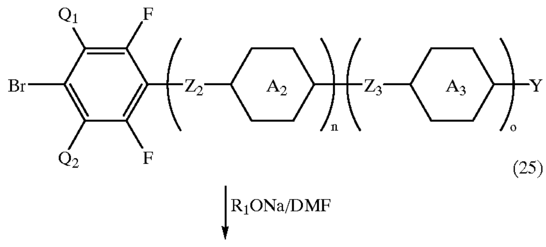

(25)

-continued

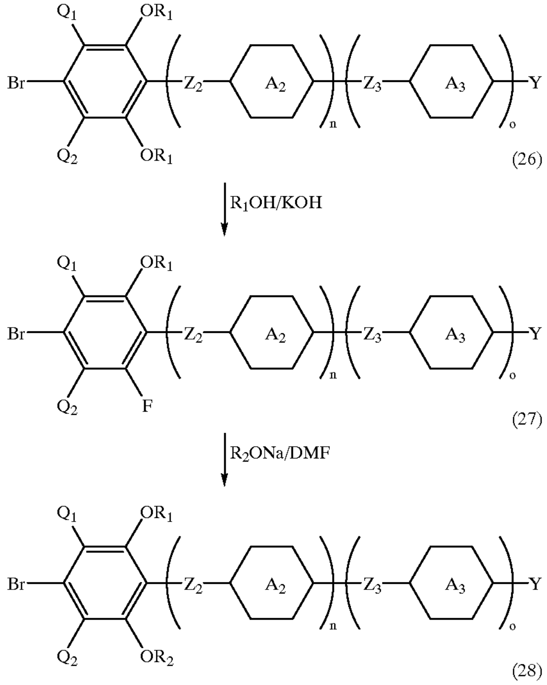

(26)

(27)

(28)

wherein $R_1$, $R_2$, ring $A_2$, ring $A_3$, $Z_2$, $Z_3$, n, o, $Q_1$, $Q_2$, and Y have the same meaning as described above.

Compounds of the formula (1-e), (1-f), (1-g), (1-h), (1-i), (1-j), (1-k) or (1-l) can be produced by using a compound of the formula (26) or (28) in place of a compound of the formula (16) and treating in the same way as described above.

(1-e)

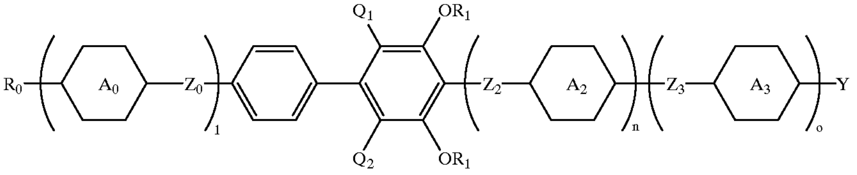

-continued (1-f)

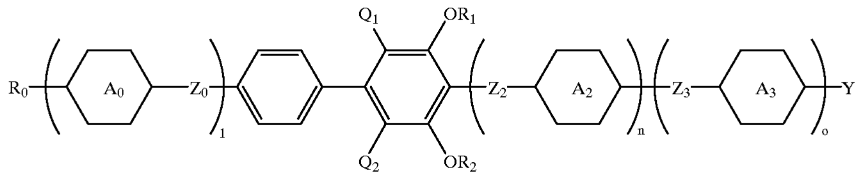

(1-g)

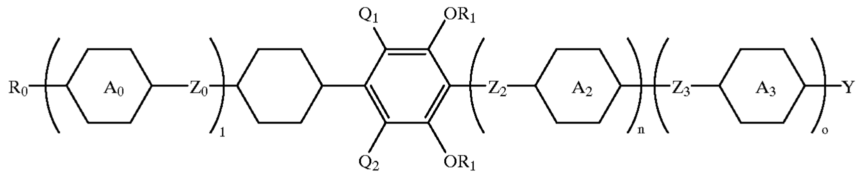

(1-h)

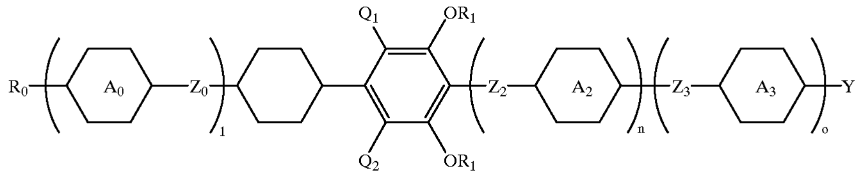

(1-i)

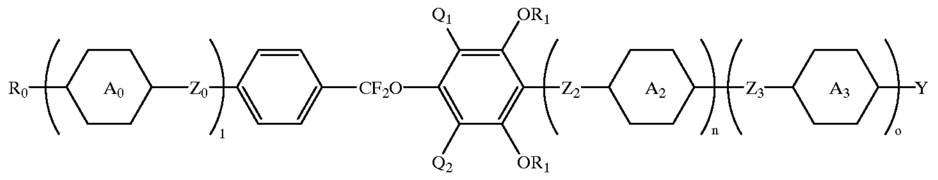

(1-j)

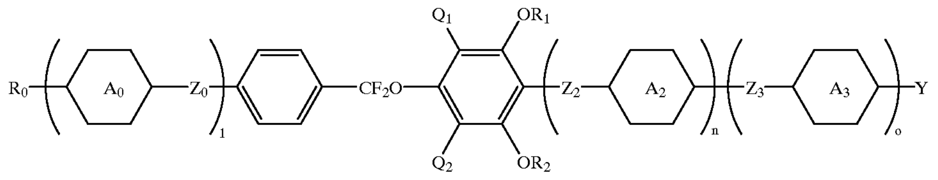

(1-k)

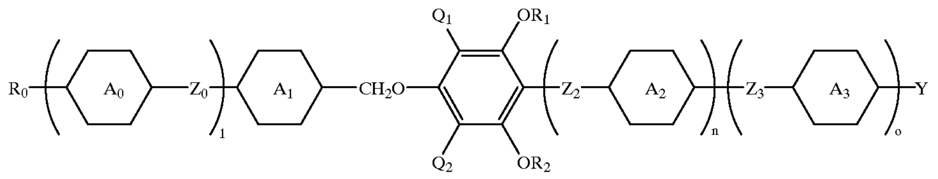

(1-l)

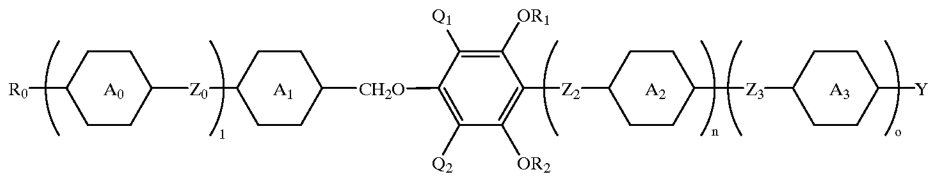

wherein $R_0$, $R_1$, $R_2$, ring $A_0$, ring $A_1$, ring $A_2$, ring $A_3$, $Z_0$, $Z_2$, $Z_3$, l, n, o, $Q_1$, $Q_2$, and Y have the same meaning as described above.

Compounds in which any one of bonding groups $Z_0$, $Z_1$, $Z_2$, and $Z_3$ is $—CH_2CH_2—$ are produced according to the method described in Japanese Patent Publication No. Hei 3-03643 or Laid-open Japanese Patent Publication No. Sho 59-25338. Compounds in which any one of the bonding groups is $—(CH_2)_4—$ are produced according to the method described in Laid-open Japanese Patent Publication No. Hei 3-66632, Laid-open Japanese Patent Publication No. Hei 4-501575, or Laid-open Japanese Patent Publication No. Hei 5-310605. Compounds in which any one of the bonding groups is —CH═CH— are produced according to the method described in Laid-open Japanese Patent Publication No. Sho 61-215336 or Laid-open Japanese Patent Publication No. Hei 3-127748. Compounds in which any one of the bonding groups is —C≡C— are produced according to the method described in Laid-open Japanese Patent Publication No. Sho 61-280441 or Laid-open Japanese Patent Publication No. Hei 1-502908.

BEST MODE FOR CARRYING OUT THE INVENTION

Now, the methods for producing and for using the compounds of present invention will be described in more detail with reference to Examples. However, it should be understood that the scope of the present invention is by no means restricted by such specific Examples. In the Examples, Cr indicates crystal, N: nematic phase, Sm: smectic phase, and Iso: isotropic liquid. Unit of all phase transition temperature is ° C.

EXAMPLE 1

Preparation of 3,4-difluoro-5-ethoxy-(trans-4-(trans-4-propylcyclohexyl)cyclohexyl)benzene (Compound No. 195; Compound expressed by the general formula (1) wherein l=m=1, n=o=0, ring $A_0$ and ring $A_1$ are 1,4-cyclohexylene group, $R_0$=n-$C_3H_7$, $R_1$=$C_2H_5$, $Z_0$ and $Z_1$ are covalent bond, $Q_1$ and $Q_2$ are hydrogen atom, and $Q_3$ and Y are fluorine atom) is described in detail with being divided into four steps.

First Step: Nucleophilic Substitution Reaction to 3,4,5-trifluorobromobenzene

To a 500 ml three neck flask provided with a stirrer, thermometer, and cooling tube were added 25.0 g (118.5 mmol) of 3,4,5-trifluorobromobenzene, 19.9 g (355.5 mmol) of potassium hydroxide, and 20 ml of ethanol, and heated to reflux while being stirred for 3 hours. After finishing of the reaction, unreacted ethanol was distilled off under a reduced pressure, 200 ml of water was added thereto, and it was extracted with 200 ml of diethyl ether. The extract was washed with water (150 ml) thrice and dried over anhydrous magnesium sulfate. The colorless oily product in an amount of 27.8 g which was obtained by distilling off the solvent was purified by silica gel column chromatography (eluent: heptane, Rf=0.36) to obtain 23.3 g of colorless oily 3,4-difluoro-5-ethoxybromobenzene.

Second Step: Preparation of 3,4-difluoro-5-ethoxy-(1hydroxy-4-(trans-4-propylcyclohexyl)cyclohexyl)benzene To a 500 ml three neck flask provided with a stirrer, thermometer, and nitrogen gas introducing tube were added 2.7 g (110.8 mmol) of magnesium turnings and 20 ml of tetrahydrofuran (hereinafter abbreviated as THF) under nitrogen gas atmosphere, and 60 ml of solution of 23.3 g (105.5 mmol) of the 3,4-difluoro-5-ethoxybromobenzene obtained in the first step in THF was added dropwise thereto in 50 minutes while being adjusted so that the reaction temperature did not exceed 50° C. After finishing of the dropping, it was further stirred for 2 hours while being heated at 50° C. Then, 60 ml of solution of 23.5 g (105.5 mmol) of 4-(trans-4-propylcyclohexyl)cyclohexanone in THF was added dropwise thereto in 30 minutes with the reaction temperature being adjusted at 45 to 50° C., and further stirred at 50° C. for 2 hours. After the reaction mixture was cooled down to a temperature lower than 5° C., 30 ml of 6N hydrochloric acid was added thereto. Subsequently, it was extracted with 200 ml of toluene, and the extract was washed with water (150 ml) twice, with 100 ml of saturated aqueous sodium carbonate solution once, and with water (150 ml) twice, and then dried over anhydrous magnesium sulfate. The solvent was distilled off under a reduced pressure to obtain 43.9 g of a brown solid.

Third Step: Preparation of 3,4-difluoro-5-ethoxy-(4-(trans-4-propylcyclohexyl)cyclohexene-1-yl)benzene To a 500 ml three neck flask provided with a stirrer, cooling tube, and Dean and Stark dehydrating tube were added 43.9 g of the brown solid obtained in the second step, 2.2 g of p-toluenesulfonic acid monohydrate, and 250 ml of toluene, and heated to reflux while being stirred for 2 hours. The reaction mixture was washed with water (200 ml) twice, with 100 ml of saturated aqueous sodium bicarbonate solution once, and with water (200 ml) twice, and dried over anhydrous magnesium sulfate. The solvent was distilled off under a reduced pressure to obtain 37.2 g of brown solid. This solid was purified by silica gel column chromatography (eluent: heptane/toluene=9/1, Rf=0.38), and then recrystallized from heptane to obtain 12.8 g of colorless crystal of 3,4-difluoro-5-(ethoxy-(trans-4-(4-propylcyclohexyl)cyclohexene-1-yl)benzene. Melting point 97.4° C.; 1H-NMR (δ ppm): 0.8–2.5 (27H, m), 4.12 (2H, q, J=6.8 Hz), 6.04 (1H, bs), 6.6–6.7 (2H, m).

Fourth Step: Preparation of 3,4-difluoro-5-ethoxy-(trans-4-(trans-4-propylcyclohexyl)cyclohexyl)benzene The 3,4-difluoro-5-ethoxy-(4-(trans-4-propylcyclohexyl)cyclohexene-1-yl)benzene obtained in the third step in an amount of 12.8 g (36.9 mmol) was dissolved in mixed solvent of 100 ml of toluene and 50 ml of ethanol. To this solution was added 13 g of Raney nickel as catalyst, and it was subjected to a catalytic hydrogenation reaction in a 300 ml autoclave at room temperature under a condition of hydrogen pressure of 3 to 4 kg/cm2 for 3 hours. From the reaction mixture, the catalyst was filtered off and then the mixture was concentrated under a reduced pressure co obtain 12.8 g of a solid. The solid thus obtained was recrystallized from heptane to obtain colorless crystals of 3,4-difluoro-5-ethoxy-(trans-4-(trans-4-propylcyclohexyl)cyclohexyl)benzene. Cr 81.8° C. Iso; 1H-NMR (δ ppm): 0.7–2.7 (30H, m), 4.11 (2H, q, J=7.1 Hz), 6.5–6.7 (2H, m); 19F-NMR (δ ppm, $CFCl_3$): −138.50.

EXAMPLE 2

Preparation of 4-fluoro-3,5-dimethoxy-(trans-4-(trans-4-propylcyclohexyl)cyclohexyl)benzene (Compound No. 199; Compound expressed by the general formula (1) wherein l=m=1, n=o=0, ring $A_0$ and ring $A_1$ are 1,4-cyclohexylene group, $R_0$=n-$C_3H_7$, $R_1$=$CH_3$, $Z_0$ and $Z_1$ are covalent bond, $Q_1$ and $Q_2$ are hydrogen atom, $Q_3$ is methoxy group, and Y is fluorine atom).

To a 500 ml three neck flask provided with a stirrer, thermometer, and cooling tube was added 50 ml of solution of 20.0 g (94.8 mmol) of 3,4,5-trifluorobromobenzene in N,N-dimethyl formamide and stirred, and then 12.8 g of sodium methoxide was added thereto in 15 minutes while the reaction temperature was adjusted at a temperature lower than 80° C. After finishing of the addition of the methoxide, it was further stirred at 60° C. for 2 hours. Water in an amount of 200 ml was added to the reaction mixture thus obtained and extracted with 200 ml of diethyl ether. The extract was washed with water (150 ml) thrice and then dried over anhydrous magnesium sulfate. A brown solid in an amount of 23.8 g which was obtained by distilling off the solvent was purified by silica gel column chromatography (eluent: heptane/toluene=8/2, Rf=0.26) to obtain 14.1 g of needle-like colorless crystals of 4-fluoro-3,5-dimethoxybromobenzene. 1H-NMR (δ ppm): 3.86 (6H, s), 6.74 (2H, d, J=7.3 Hz); 19F-NMR (δ ppm, $CFCl_3$): −160.86.

Using the 4-fluoro-3,5-dimethoxybromobenzene (14.1 g) obtained by the procedures described above as starting material, procedures were carried out according to the preparation method shown in the second to fourth steps in Example 1 to obtain 6.3 g of the object compound, 4-fluoro-3,5-dimethoxy-(trans-4-(trans-4-propylcyclohexyl)cyclohexyl)benzene. Cr 108.5 Iso; 1H-NMR (δ ppm): 0.7–2.1 (26H, m), 2.40 (1H, m), 3.87 (6H, s), 6.44 (2H, d, J=7.3 Hz); 19F-NMR (δ ppm, $CFCl_3$): −162.31.

EXAMPLE 3

Preparation of 4-propyl-α,α-difluorobenzyl(3-fluoro-4-trifluoromethyl-5-ethoxyphenyl)ether (Compound No. 30; Compound expressed by the general formula (1) wherein l=1, m=n=o=0, ring $A_0$ is 1,4-phenylene group, $R_0$=n-$C_3H_7$, $R_1$=$C_2H_5$, $Z_0$ is difluoromethyleneoxy group, $Q_1$ and $Q_2$ are hydrogen atom, $Q_3$ is fluorine atom, and Y is trifluoromethyl group) is described with being divided into five steps.

First Step: Nucleophilic Substitution Reaction to 2,6-difluoro-4-bromobenzotrifluoride To a 500 ml three neck flask provided with a stirrer, thermometer, and cooling tube were added 20.0 g (76.7 mmol) of 2,6-difluoro-4-bromobenzotrifluoride, 12.9 g (222.9 mmol) of potassium hydroxide, and 100 ml of ethanol, and heated to reflux while being stirred for 4 hours. After unreacted ethanol was distilled off under a reduced pressure from the reaction mixture, 200 ml of water was added thereto and extracted with 200 ml of diethyl ether. The extract was washed with water (150 ml) thrice and then dried over anhydrous magnesium sulfate. The colorless oily product in an amount of 20.5 g which was obtained by distilling off the solvent was purified by silica gel column chromatography (eluent: heptane) to obtain 18.7 g of colorless oily 2-fluoro-4-bromo-6-ethoxybenzotrifluoride.

Second Step: Preparation of 3-fluoro-4-trifluoromethyl-5-ethoxyphenol

To a 300 ml three neck flask provided with a stirrer, thermometer, and nitrogen gas introducing tube were added 1.7 g (68.4 mmol) of magnesium turnings and 15 ml of diethyl ether under nitrogen gas atmosphere, and then solution of 18.7 g (65.1 mmol) of the 2-fluoro-4-bromo-6-ethoxybenzotrifluoride obtained in the first step in 70 ml of diethyl ether was added dropwise while being stirred in 25 minutes. After finishing of the dropping, it was further heated while being stirred for 2 hours. Then, the reaction mixture was cooled down to a temperature lower than 5° C., 8.1 g (78.2 mmol) of trimethyl borate was added dropwise thereto while being maintained at that temperature, stirred at the same temperature for 20 minutes, and then 9.8 g (162.9 mmol) of acetic acid was added. Then, 18.4 g of 30% aqueous hydrogen peroxide solution was added dropwise thereto and further stirred at room temperature for 6 hours. The reaction mixture was put in 200 ml of 15% aqueous sodium thiosulfate solution to terminate the reaction, and then extracted with diethyl ether. The extract was washed with water (150 ml) thrice and dried over anhydrous magnesium sulfate, and then the solvent was distilled off to obtain 13.5 g of colorless oily product. This product was subjected to a distillation under a reduced pressure to obtain 8.5 g of colorless crystals of 3-fluoro-4-trifluoromethyl-5-ethoxyphenol. Melting point was 82.7° C.

Third Step: Preparation of 4-propylthiobenzoic acid chloride

To a 1000 ml three neck flask provided with a stirrer, thermometer, dropping funnel, and nitrogen gas introducing tube were added 9.4 g (386.8 mmol) of magnesium turnings and 20 ml of THF under nitrogen gas atmosphere, and 200 ml solution of 70.0 g (351.6 mmol) of 4-propylbromobenzene in THF was added dropwise while being stirred in 1 hour while the reaction temperature being adjusted at 45 to 55° C. After finishing of the dropping, it was stirred at 55° C. for 2 hours. The reaction mixture thus obtained was cooled down to a temperature lower than 10° C., 133.8 g (1.75 mol) of carbon disulfide was added dropwise thereto in 50 minutes. After finishing of the dropping, it was further stirred at room temperature for 14 hours. The reaction mixture was cooled down to a temperature lower than 5° C., and then 100 ml of 6N hydrochloric acid was added dropwise thereto to terminate the reaction. It was extracted with 300 ml of diethyl ether, and the extract was washed with water (200 ml) thrice, dried over anhydrous magnesium sulfate, and the solvent was distilled off under a reduced pressure to obtain 64.2 g of purplish red oily 4-propyldithiobenzoic acid. 1H-NMR (δ ppm): 0.95 (3H, t, J=7.4 Hz), 1.65 (2H, m), 2.63 (2H, t, J=7.8 Hz), 6.0–6.5 (1H, bs), 7.18 (2H, d, J=8.3 Hz), 7.99 (2H, d, J=8.6 Hz).

To a 300 ml three neck flask provided with a stirrer, thermometer, cooling tube, and dropping funnel were added 11.1 g (56.7 mmol) of the 4-propyldithiobenzoic acid obtained by the procedures described above and 60 ml of diethyl ether, and 13.5 g (113.4 mmol) of thionyl chloride was added dropwise thereto while being stirred at room temperature in 5 minutes, and further heated to reflux for 8 hours. From the reaction mixture, diethyl ether was distilled off, and unreacted thionyl chloride was distilled off under a reduced pressure to obtain 11.5 g of dark purplish red oily 4-propylthiobenzoic acid chloride.

Fourth Step: Preparation of thion-O-ester derivative (29)

To a 300 ml three neck flask provided with a stirrer, thermometer, cooling tube, and dropping funnel were added 8.5 g (37.8 mmol) of the 3-fluoro-4-trifluoromethyl-5-ethoxyphenol obtained in the second step described above, 4.5 g (56.7 mmol) of pyridine, and 20 ml of toluene, and a solution of 11.5 g of the 4-propylthiobenzoic acid chloride obtained in the third step in 25 ml of toluene was added dropwise thereto while being stirred at room temperature in 15 minutes and further stirred at 65° C. for 6 hours. Water in an amount of 100 ml was added to the reaction mixture and extracted with toluene (150 ml) twice. The extract was washed with 50 ml of 3N hydrochloric acid once, with water (150 ml) twice, with 100 ml of saturated aqueous sodium carbonate solution once, and further with water (150 ml) twice, and then dried over anhydrous magnesium sulfate. The solvent was distilled off under a reduced pressure to obtain 16.9 g of a reddish brown solid. The solid was subjected to silica gel column chromatography (eluent: mixed solvent of heptane/toluene=1/1) and further recrystallized from heptane to obtain 11.8 g of yellow needle like crystals of thion-O-ester derivative (29). Melting point was 81.2° C. 1H-NMR (δ ppm): 0.96 (3H, t, J=7.0 Hz), 1.2–2.0 (5H, m), 2.4–2.9 (2H, m), 4.1 (2H, q, J=6.8 Hz), 6.5–6.7 (2H, m), 7.1–7.3 (2H, m), 8.2–8.4 (2H, m).

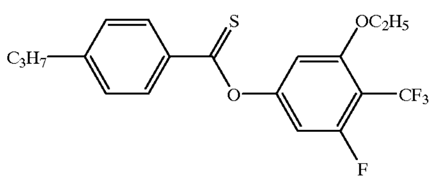

(29)

Fifth Step: Preparation of 4-propyl-α,α-difluorobenzyl(3-fluoro-4-trifluoromethyl-5-ethoxyphenyl)ether To a 200 ml eggplant type flask provided with a cooling tube, dropping funnel, and nitrogen gas introducing tube was added a solution of 11.8 g (30.6 mmol) of the thion-O-ester derivative (29) obtained by the fourth step described above in 80 ml of dichloromethane, and 12.3 g (76.5 mmol) of diethylaminosulfur trifluoride (DAST) was added thereto at room temperature while being stirred with a magnetic stirrer, and further stirred for 20 hours. After the reaction mixture was put in saturated aqueous sodium carbonate solution, the dichloromethane layer was separated, and the water layer was extracted with 200 ml of dichloromethane. The dichloromethane layers were combined and washed with water (150 ml) thrice and then dried over anhydrous magnesium sulfate. The solvent was distilled off under a reduced pressure to obtain 11.1 g of a colorless solid. This solid was subjected to silica gel column chromatography (eluent: mixed solvent of heptane/toluene=1/1) to obtain 3.4 g of oily 4-propyl-α,α-difluorobenzyl(3-fluoro-4-trifluoromethyl-5-ethoxyphenyl)ether. 1H-Nmr (δ ppm): 0.94 (3H, t, J=7.0 Hz), 1.3–1.9 (5H, m), 2.64 (2H, t, J=7.0 Hz), 4.1 (2H, q, J=7.0 Hz), 6.5–6.8(2H, m), 7.2–7.4 (2H, m), 7.5–7.8 (2H, m); 19F-NMR (δ ppm: $CFCl_3$): −56.69 (d, —$CF_3$), −66.07 (s, —$CF_2O$—), −109.22~110.99 (m); GC-MS (EI): M+392.

EXAMPLE 4

Compounds (Compound Nos. 1 to 440) shown below are prepared according to the preparation methods described in Examples 1 to 3 described above, or by selecting various reactions described in patent publications or reference books of organic synthesis and using them in combination.

| No. | 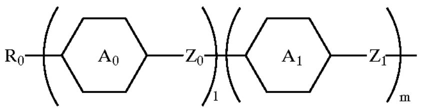 | 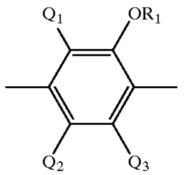 | 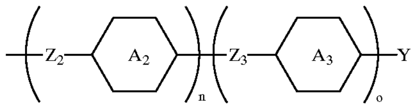 |
| --- | --- | --- | --- |
| 1 | 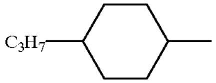 | 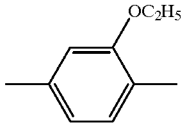 | —F |
| 2 | 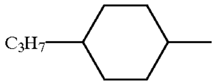 | 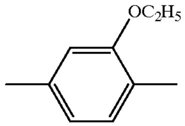 | —$CF_3$ |
| 3 | 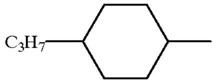 | 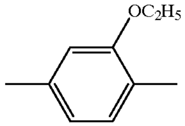 | —$CF_2H$ |
| 4 | 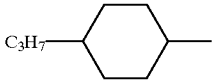 | 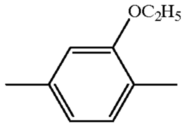 | —$OCF_3$ |
| 5 | 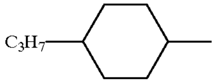 | 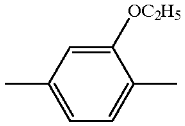 | —$OCHF_2$ |

-continued
| No. | 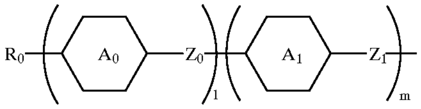 | 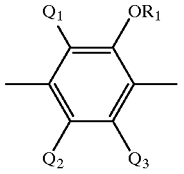 | 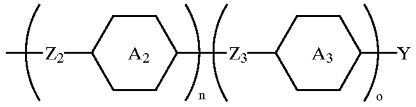 |
|---|---|---|---|
| 6 | 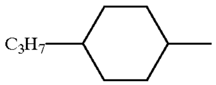 | 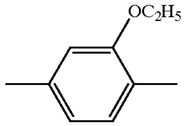 | —CN |
| 7 | 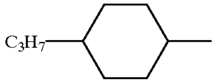 | 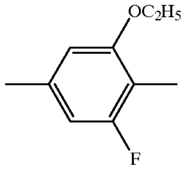 | —F |
| 8 | 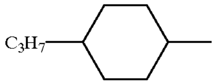 | 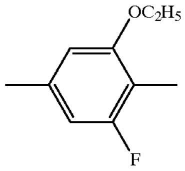 | $—CF_3$ |
| 9 | 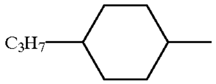 | 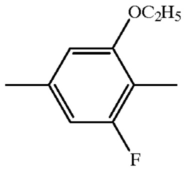 | $—OCF_3$ |

-continued
| No. | | | |
|---|---|---|---|
| | 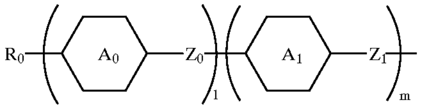 | 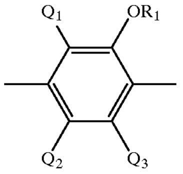 | 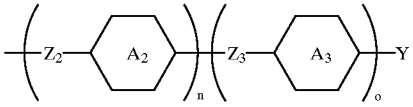 |
| 10 | 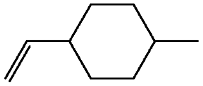 | 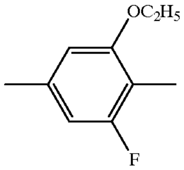 | —CN |
| 11 | 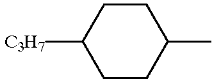 | 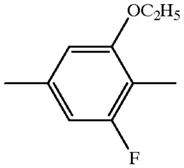 | $—C_2H_5$ |
| 12 | 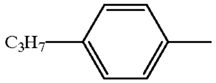 | 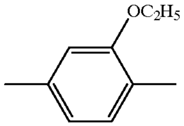 | —F |
| 13 | 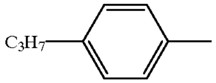 | 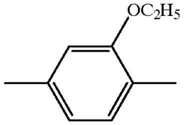 | $—CF_3$ |
| 14 | 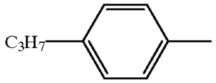 | 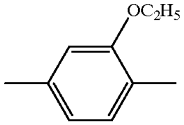 | $—CF_2H$ |

-continued
| No. | 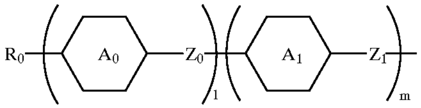 | 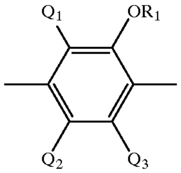 | 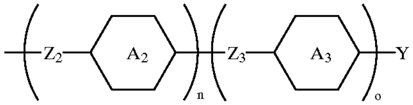 |
| --- | --- | --- | --- |
| 15 | 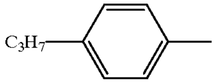 | 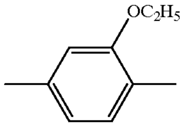 | $-OCF_3$ |
| 16 | 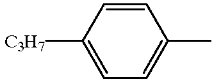 | 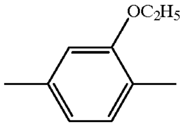 | $-OCHF_2$ |
| 17 | 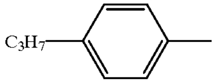 | 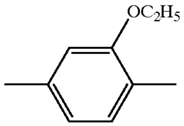 | $-CN$ |
| 18 | 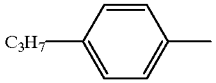 | 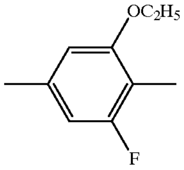 | $-F$ |
| 19 | 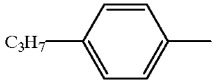 | 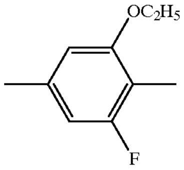 | $-CF_3$ |

-continued
| No. | 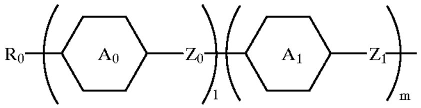 | 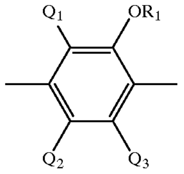 | 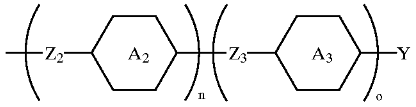 |
|---|---|---|---|
| 20 | 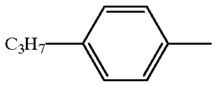 | 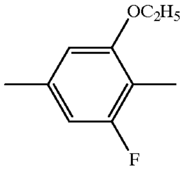 | $-OCF_3$ |
| 21 | 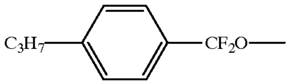 | 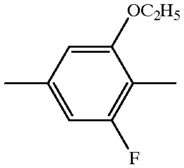 | $-CN$ |
| 22 | 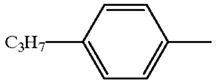 | 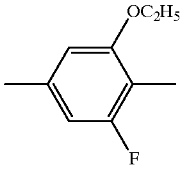 | $-C_2H_5$ |
| 23 | 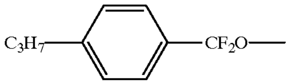 | 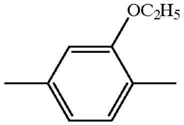 | $-F$ |
| 24 | 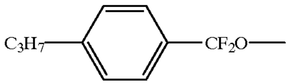 | 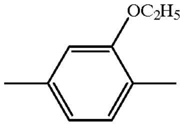 | $-CF_3$ |

-continued
| No. | | | |
|---|---|---|---|
| | 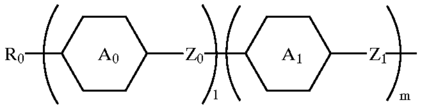 | 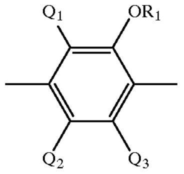 | 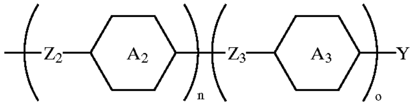 |
| 25 | 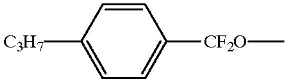 | 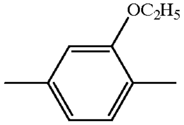 | $—CF_2H$ |
| 26 | 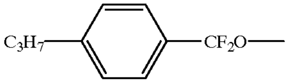 | 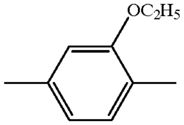 | $—OCF_3$ |
| 27 | 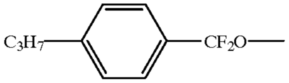 | 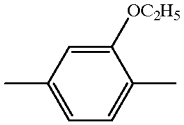 | $—OCHF_2$ |
| 28 | 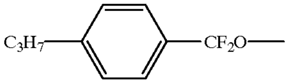 | 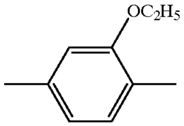 | —CN |
| 29 | 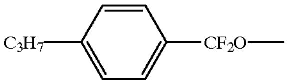 | 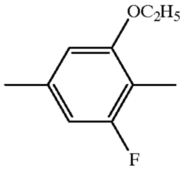 | —F |

-continued
| No. | 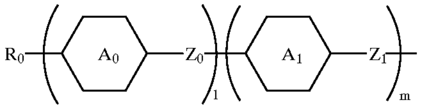 | 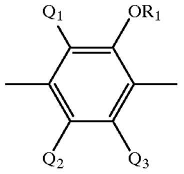 | 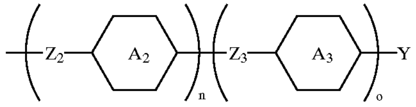 |
|---|---|---|---|
| 30 | 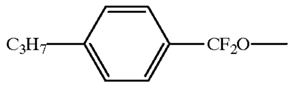 | 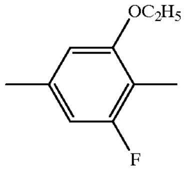 | $—CF_3$ |
| 31 | 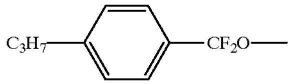 | 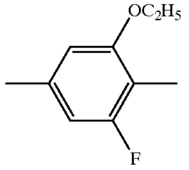 | $—OCF_3$ |
| 32 | 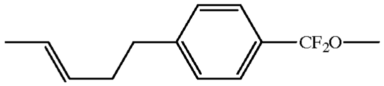 | 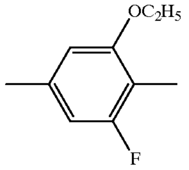 | —CN |
| 33 | 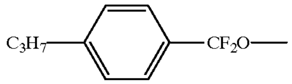 | 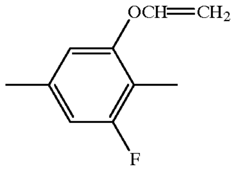 | $—C_2H_5$ |

-continued
| No. | 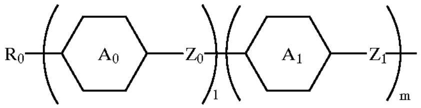 | 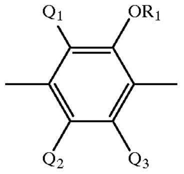 | 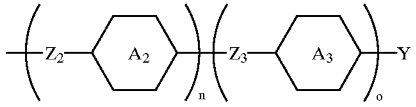 |
|---|---|---|---|
| 34 | 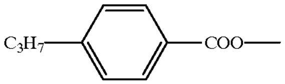 | 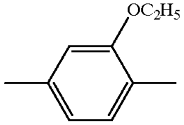 | —F |
| 35 | 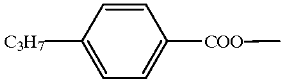 | 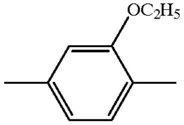 | $—CF_3$ |
| 36 | 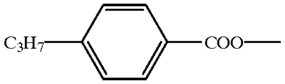 | 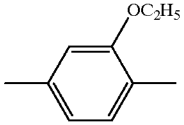 | $—CF_2H$ |
| 37 | 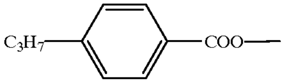 | 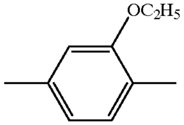 | $—OCF_3$ |
| 38 | 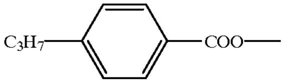 | 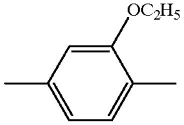 | $—OCHF_2$ |

-continued
| No. | 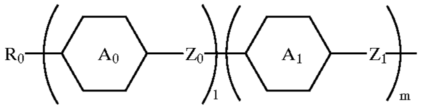 | 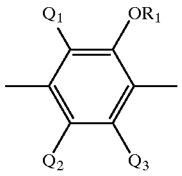 | 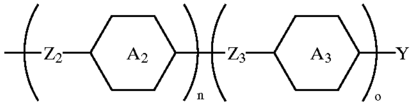 |
|---|---|---|---|
| 39 | 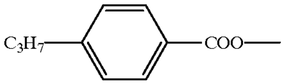 | 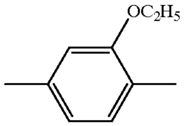 | —CN |
| 40 | 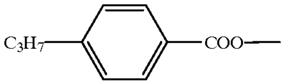 | 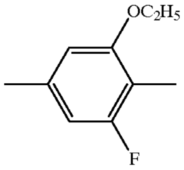 | —F |
| 41 | 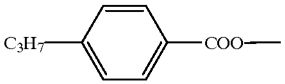 | 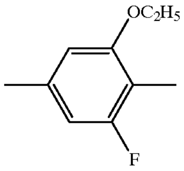 | $—CF_3$ |
| 42 | 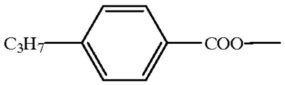 | 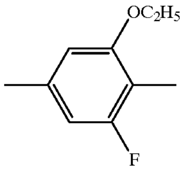 | $—OCF_3$ |

-continued
| No. | 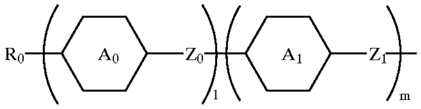 | 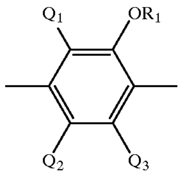 | 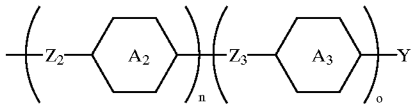 |
|---|---|---|---|
| 43 | 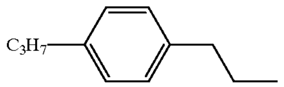 | 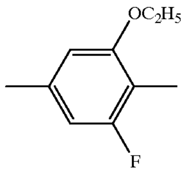 | $—CN$ |
| 44 | 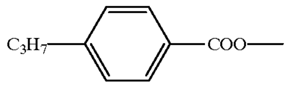 | 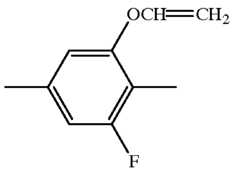 | $—C_2H_5$ |
| 45 | 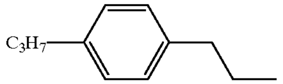 | 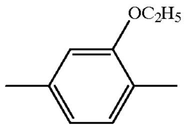 | $—F$ |
| 46 | 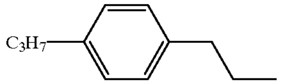 | 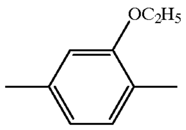 | $—CF_3$ |
| 47 | 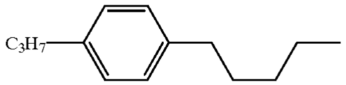 | 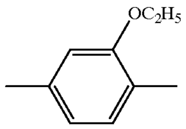 | $—CF_2H$ |

-continued
| No. | | | |
|---|---|---|---|
| | 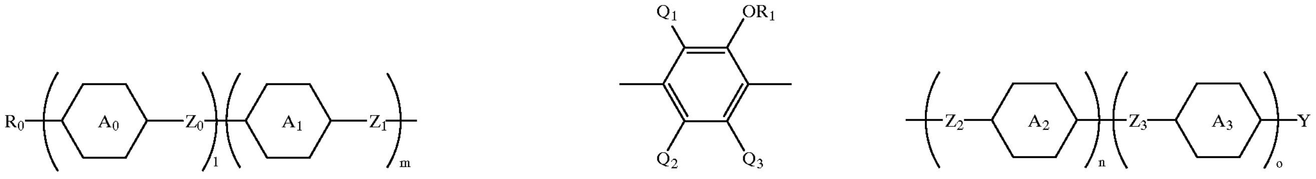 | | |
| 48 | 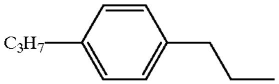 | 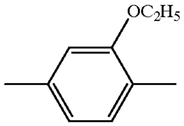 | —$OCF_3$ |
| 49 | 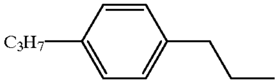 | 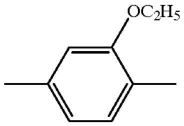 | —$OCHF_2$ |
| 50 | 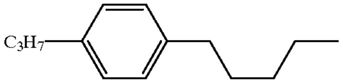 | 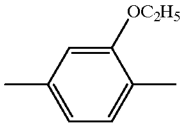 | —CN |
| 51 | 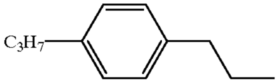 | 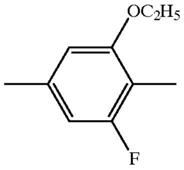 | —F |
| 52 | 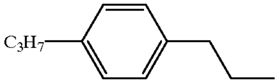 | 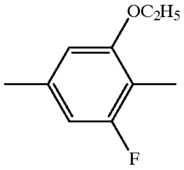 | —$CF_3$ |

-continued
| No. | 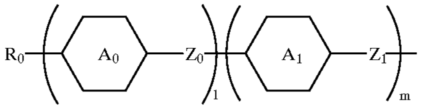 | 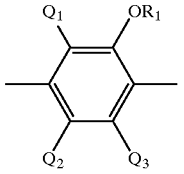 | 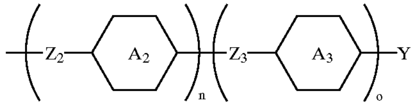 |
|---|---|---|---|
| 53 | 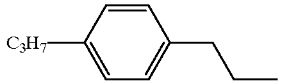 | 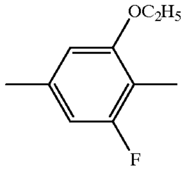 | $—OCF_3$ |
| 54 | 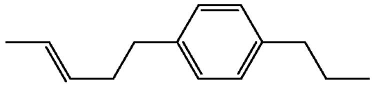 | 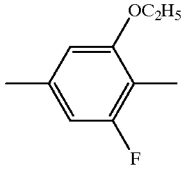 | —CN |
| 55 | 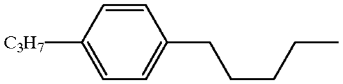 | 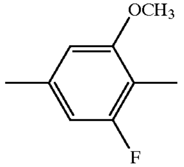 | $—C_2H_5$ |
| 56 | 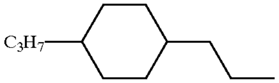 | 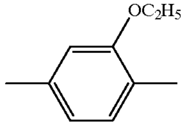 | —F |
| 57 | 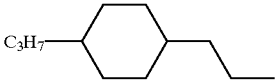 | 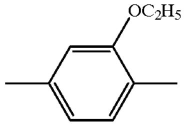 | $—CF_3$ |

-continued
| No. | 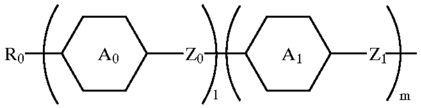 | 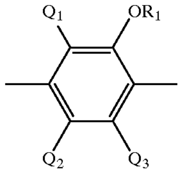 | 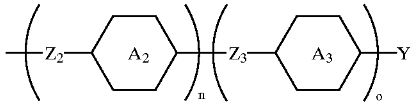 |
|---|---|---|---|
| 58 | 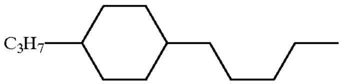 | 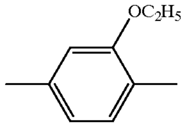 | $—CF_2H$ |
| 59 | 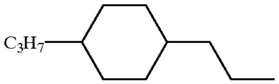 | 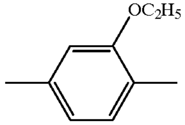 | $—OCF_3$ |
| 60 | 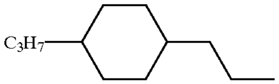 | 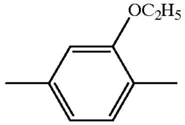 | $—OCHF_2$ |
| 61 | 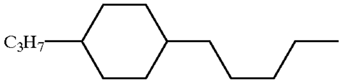 | 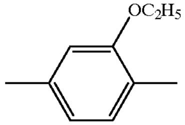 | —CN |
| 62 | 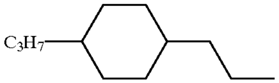 | 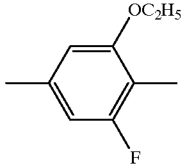 | —F |

-continued
| No. | | | |
|---|---|---|---|
| | 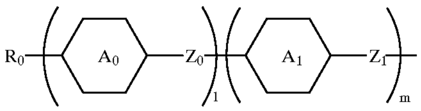 | 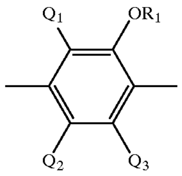 | 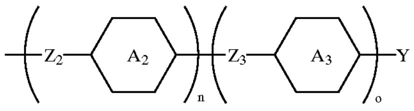 |
| 63 | 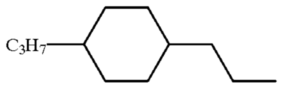 | 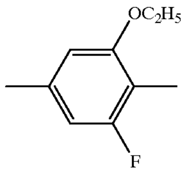 | —$CF_3$ |
| 64 | 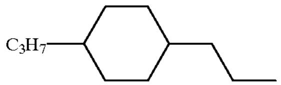 | 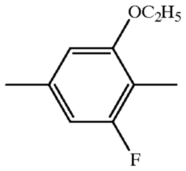 | —$OCF_3$ |
| 65 | 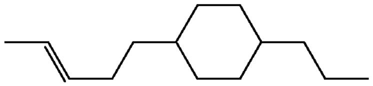 | 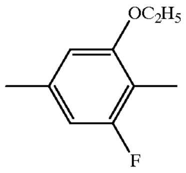 | —CN |
| 66 | 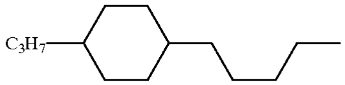 | 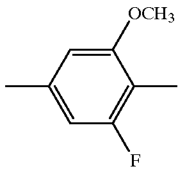 | —$C_2H_5$ |
| 67 | 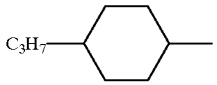 | 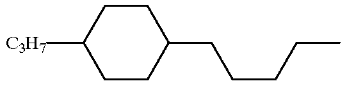 | —F |

-continued
| No. | 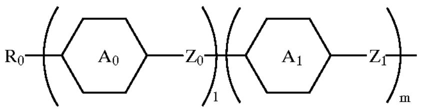 | 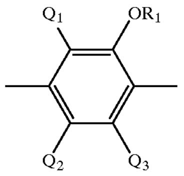 | 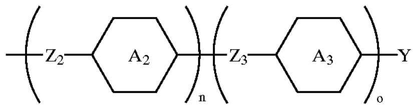 |
|---|---|---|---|
| 68 | 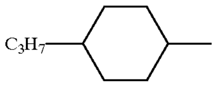 | 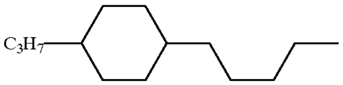 | $—CF_3$ |
| 69 | 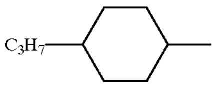 | 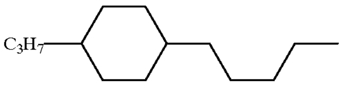 | $—OCF_3$ |
| 70 | 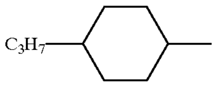 | 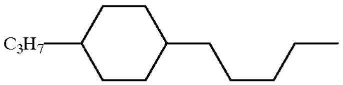 | $—OCHF_2$ |
| 71 | 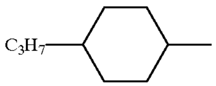 | 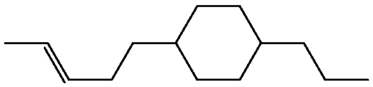 | —CN |
| 72 | 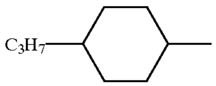 | 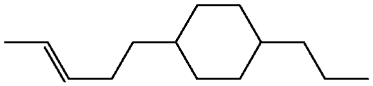 | —F |
| 73 | 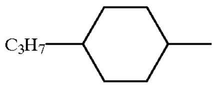 | 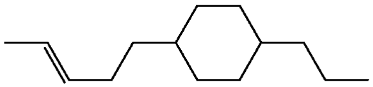 | $—CF_3$ |
| 74 | 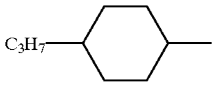 | 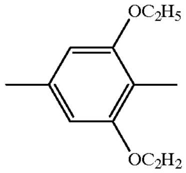 | $—OCF_3$ |

-continued
| No. | | | |
|---|---|---|---|
| | 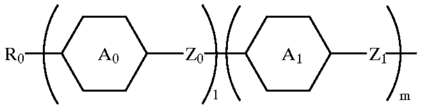 | 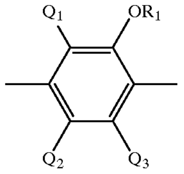 | 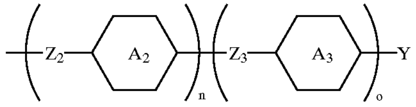 |
| 75 | 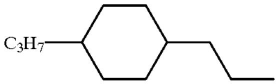 | 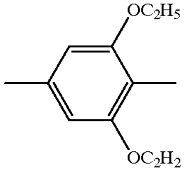 | $—CN$ |
| 76 | 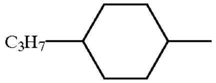 | 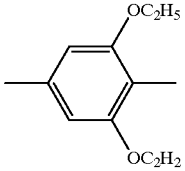 | $—C_2H_5$ |
| 77 | 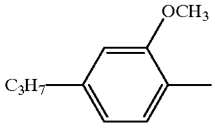 | 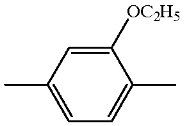 | $—F$ |
| 78 | 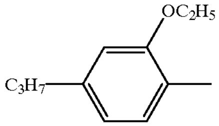 | 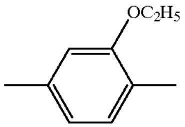 | $—CF_3$ |
| 79 | 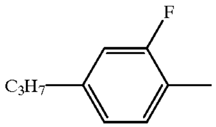 | 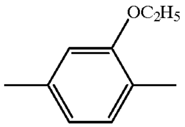 | $—CF_2H$ |

-continued
| No. | 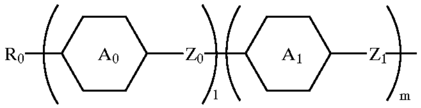 | 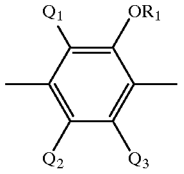 | 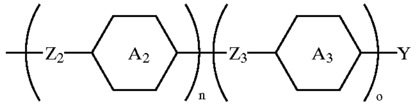 |
|---|---|---|---|
| 80 | 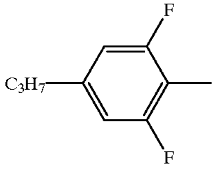 | 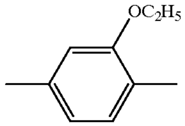 | $—OCF_3$ |
| 81 | 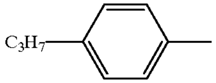 | 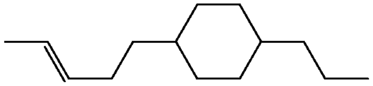 | $—OCHF_2$ |
| 82 | 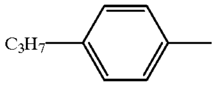 | 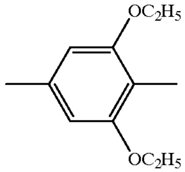 | —CN |
| 83 | 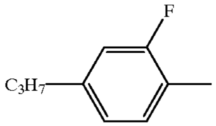 | 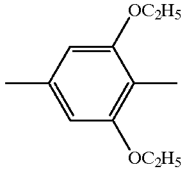 | —F |
| 84 | 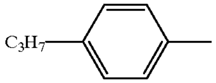 | 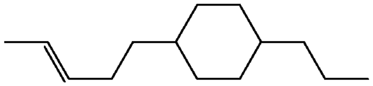 | $—CF_3$ |

-continued
| No. | 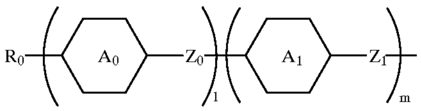 | 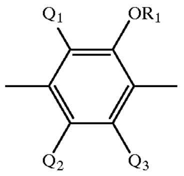 | 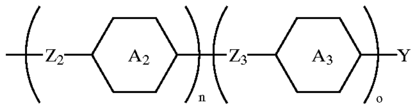 |
|---|---|---|---|
| 85 | 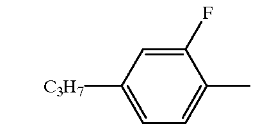 | 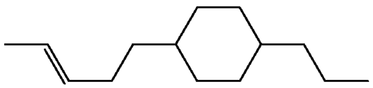 | $—OCF_3$ |
| 86 | 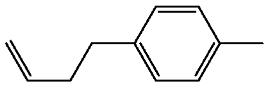 | 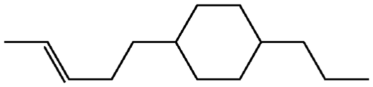 | —CN |
| 87 | 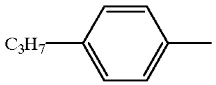 | 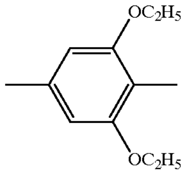 | $—C_2H_5$ |
| 88 | 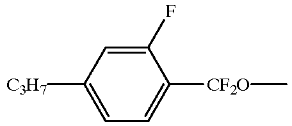 | 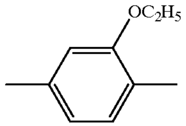 | —F |
| 89 | 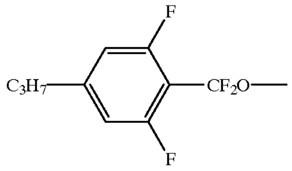 | 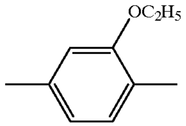 | $—CF_3$ |

-continued
| No. | 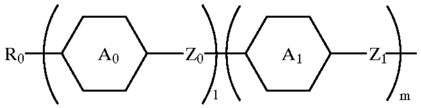 | 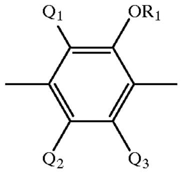 | 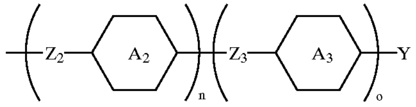 |
|---|---|---|---|
| 90 | 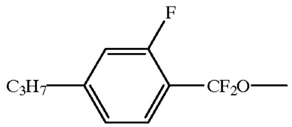 | 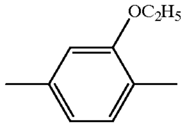 | $-CF_2H$ |
| 91 | 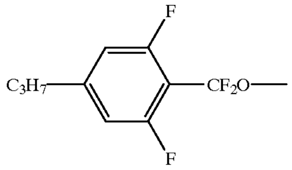 | 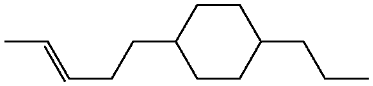 | $-OCF_3$ |
| 92 | 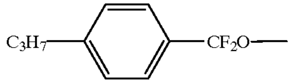 | 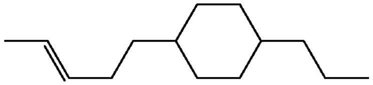 | $-OCHF_2$ |
| 93 | 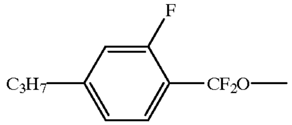 | 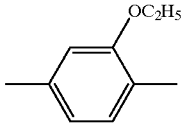 | —CN |
| 94 | 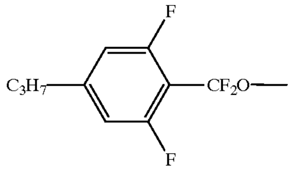 | 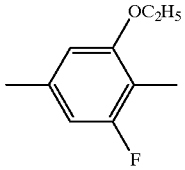 | —F |

-continued
| No. | 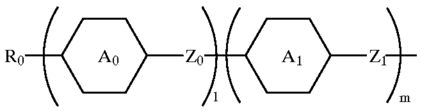 | 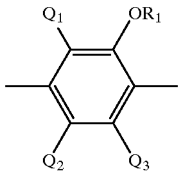 | 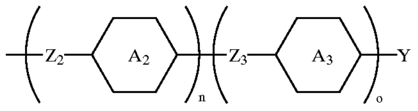 |
|---|---|---|---|
| 95 | 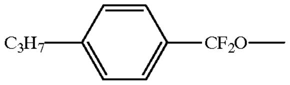 | 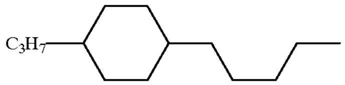 | $—CF_3$ |
| 96 | 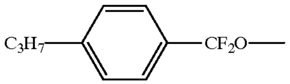 | 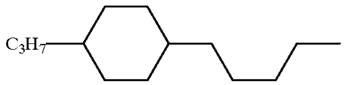 | $—OCF_3$ |
| 97 | 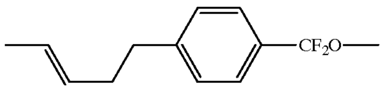 | 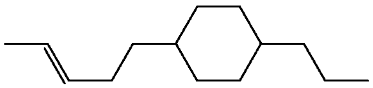 | —CN |
| 98 | 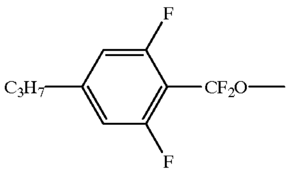 | 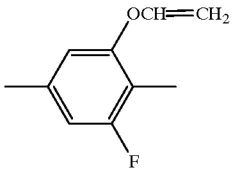 | $—C_2H_5$ |
| 99 | 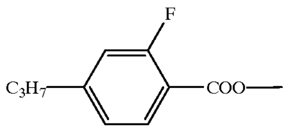 | 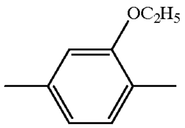 | —F |
| 100 | 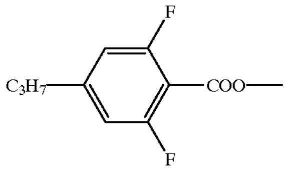 | 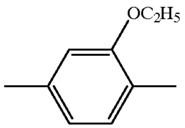 | $—CF_3$ |

-continued
| No. | 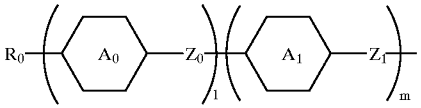 | 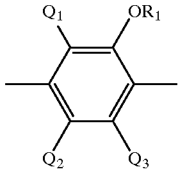 | 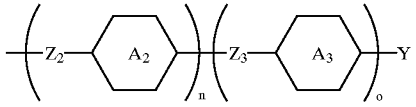 |
|---|---|---|---|
| 101 | 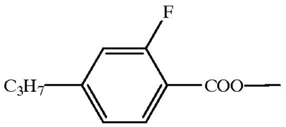 | 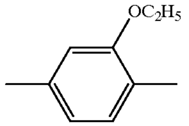 | $—CF_2H$ |
| 102 | 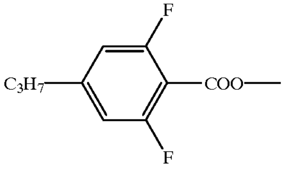 | 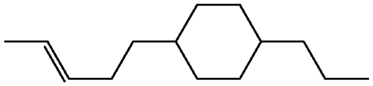 | $—OCF_3$ |
| 103 | 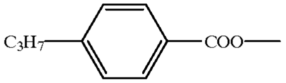 | 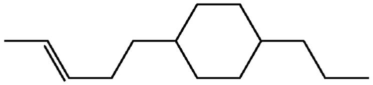 | $—OCHF_2$ |
| 104 | 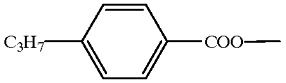 | 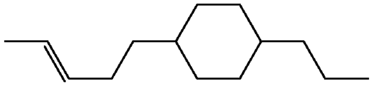 | —CN |
| 105 | 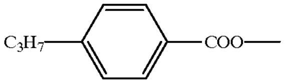 | 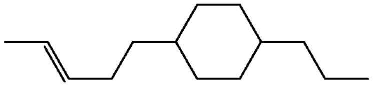 | —F |
| 106 | 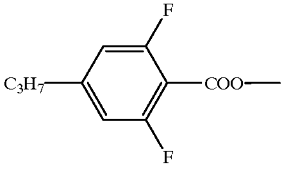 | 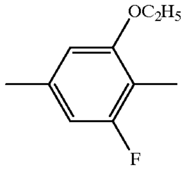 | $—CF_3$ |

-continued
| No. | 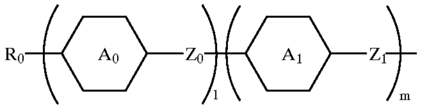 | 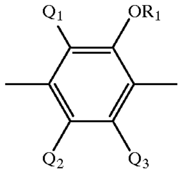 | 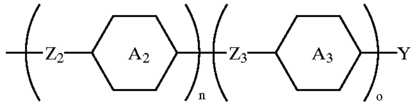 |
|---|---|---|---|
| 107 | 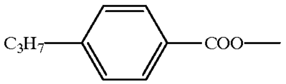 | 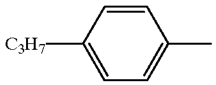 | $—OCF_3$ |
| 108 | 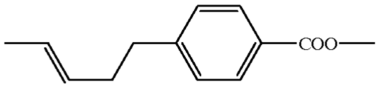 | 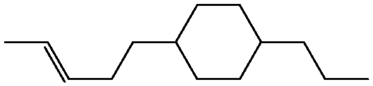 | —CN |
| 109 | 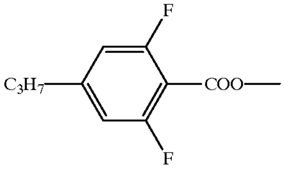 | 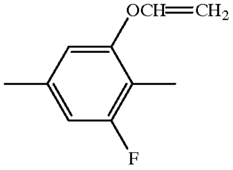 | $—C_2H_5$ |
| 110 | 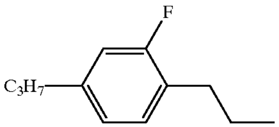 | 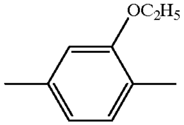 | —F |
| 111 | 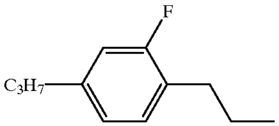 | 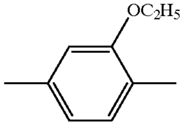 | $—CF_3$ |

-continued
| No. | 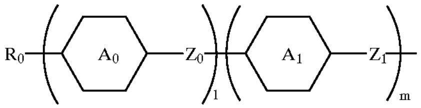 | 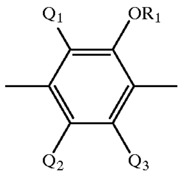 | 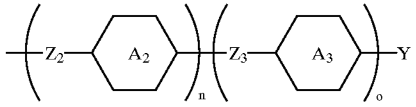 |
|---|---|---|---|
| 112 | 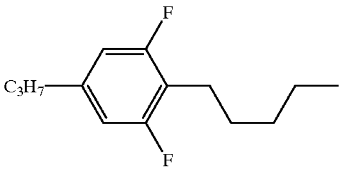 | 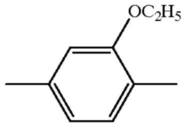 | —$CF_2H$ |
| 113 | 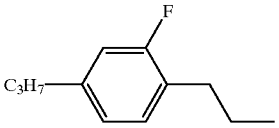 | 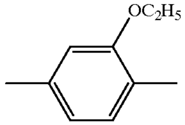 | —$OCF_3$ |
| 114 | 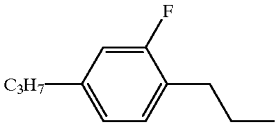 | 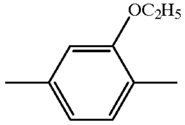 | —$OCHF_2$ |
| 115 | 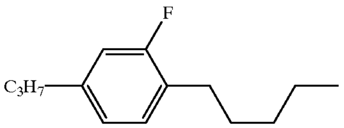 | 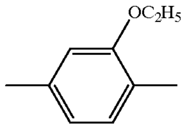 | —CN |
| 116 | 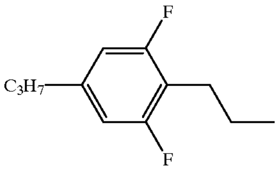 | 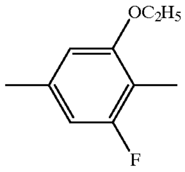 | —F |

-continued
| No. | 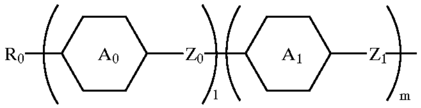 | 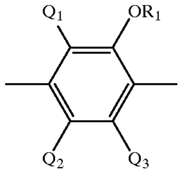 | 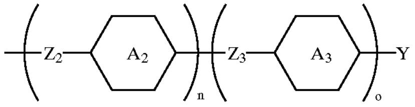 |
|---|---|---|---|
| 117 | 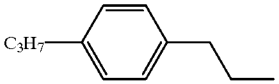 | 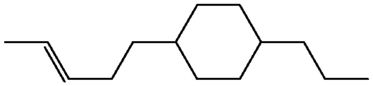 | —$CF_3$ |
| 118 | 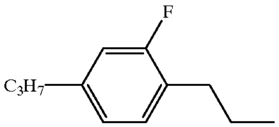 | 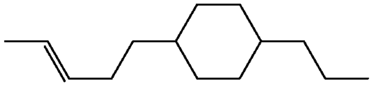 | —$OCF_3$ |
| 119 | 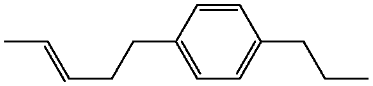 | 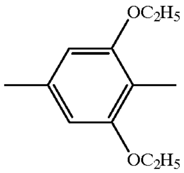 | —CN |
| 120 | 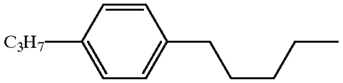 | 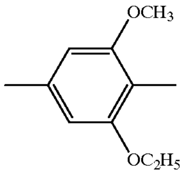 | —$C_2H_5$ |
| 121 | 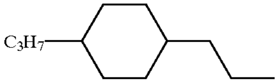 | 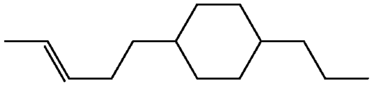 | —F |
| 122 | 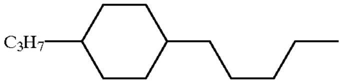 | 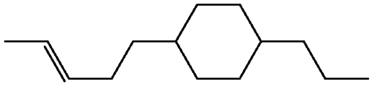 | —$CF_3$ |

-continued
| No. | 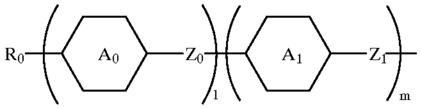 | 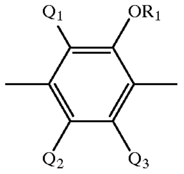 | 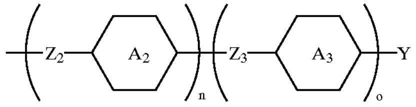 |
|---|---|---|---|
| 123 | 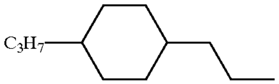 | 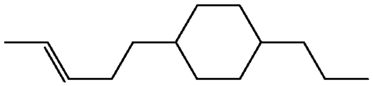 | $—OCF_3$ |
| 124 | 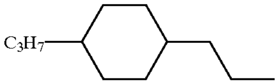 | 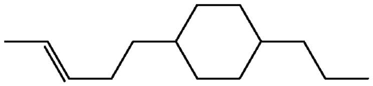 | $—OCHF_2$ |
| 125 | 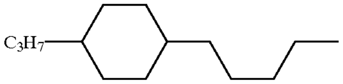 | 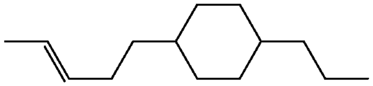 | —CN |
| 126 | 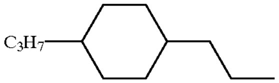 | 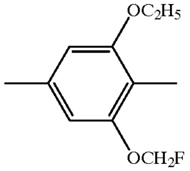 | —F |
| 127 | 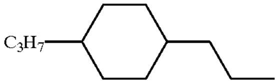 | 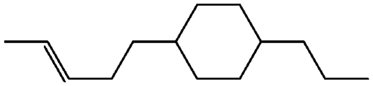 | $—CF_3$ |
| 128 | 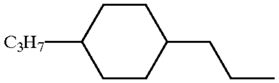 | 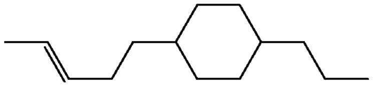 | $—OCF_3$ |
| 129 | 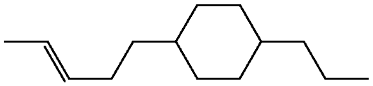 | 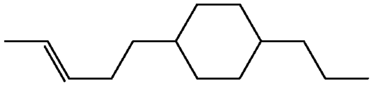 | —CN |

-continued
| No. | 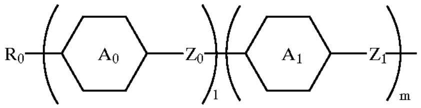 | 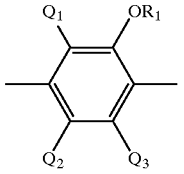 | 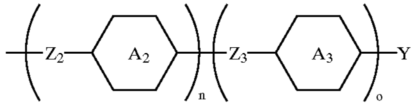 |
|---|---|---|---|
| 130 | 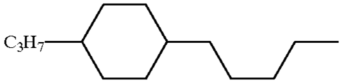 | 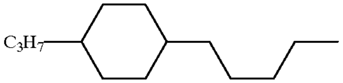 | —$C_2H_5$ |
| 131 | $C_3H_7$— | 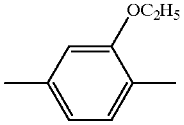 | 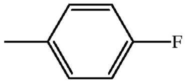 |
| 132 | $C_3H_7$— | 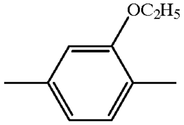 | 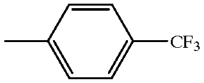 |
| 133 | $C_3H_7$— | 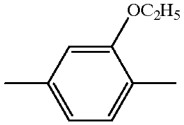 | 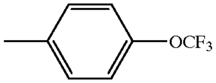 |
| 134 | $C_3H_7$— | 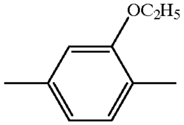 | 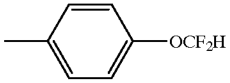 |
| 135 | $C_3H_7$— | 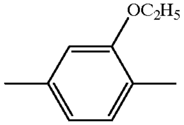 | 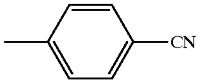 |

-continued
| No. | 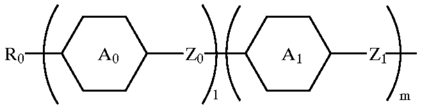 | 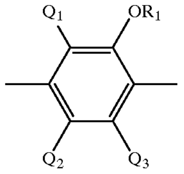 | 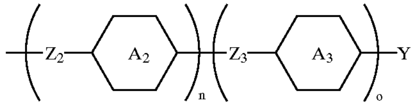 |
|---|---|---|---|
| 136 | $C_3H_7$— | 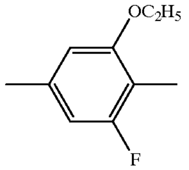 | 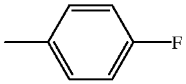 |
| 137 | $C_3H_7$— | 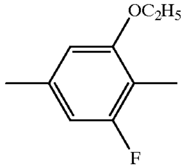 | 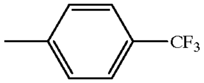 |
| 138 | $C_3H_7$— | 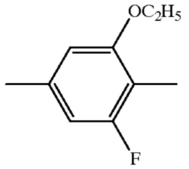 | 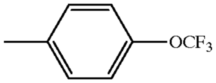 |
| 139 | 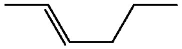 | 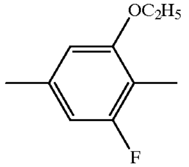 | 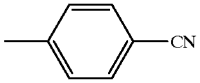 |

-continued
| No. | 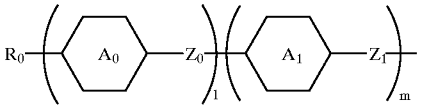 | 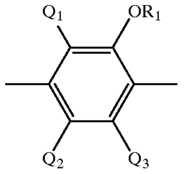 | 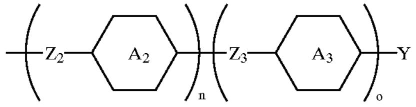 |
|---|---|---|---|
| 140 | $C_3H_7$— | 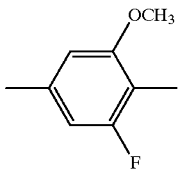 | 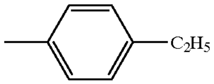 |
| 141 | $C_3H_7$— | 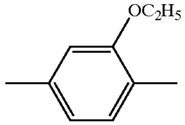 | 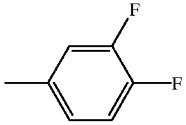 |
| 142 | $C_3H_7$— | 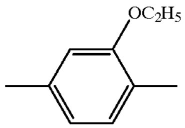 | 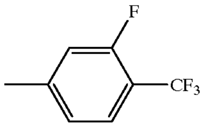 |
| 143 | $C_3H_7$— | 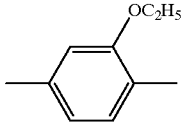 | 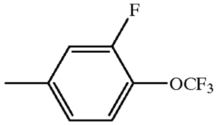 |
| 144 | $C_3H_7$— | 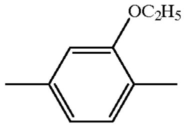 | 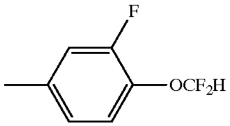 |

-continued
| No. | 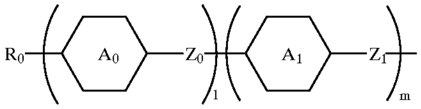 | 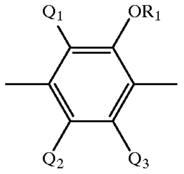 | 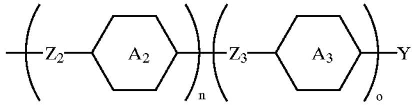 |
|---|---|---|---|
| 145 | $C_3H_7$— | 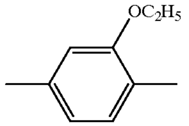 | 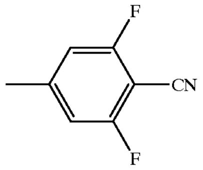 |
| 146 | $C_3H_7$— | 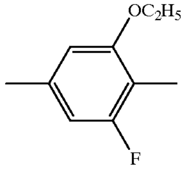 | 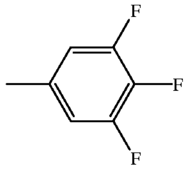 |
| 147 | $C_3H_7$— | 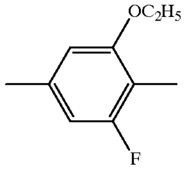 | 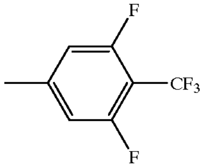 |
| 148 | $C_3H_7$— | 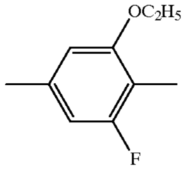 | 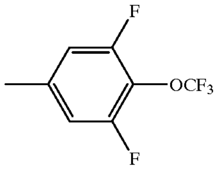 |

-continued
| No. | 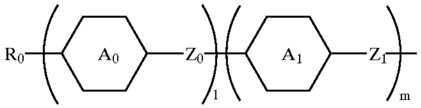 | 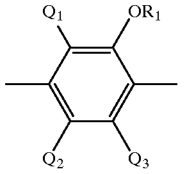 | 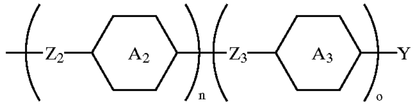 |
|---|---|---|---|
| 149 | 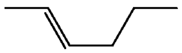 | 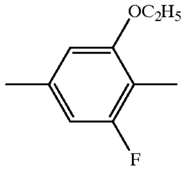 | 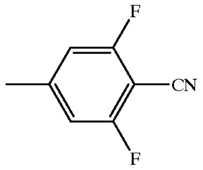 |
| 150 | $C_3H_7$— | 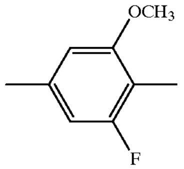 | 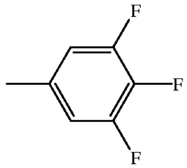 |
| 151 | $C_3H_7$— | 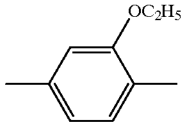 | 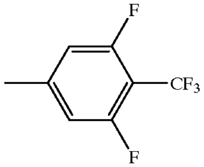 |
| 152 | $C_3H_7$— | 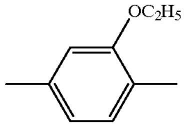 | 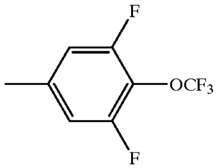 |

-continued
| No. | 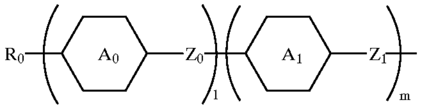 | 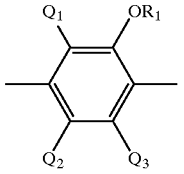 | 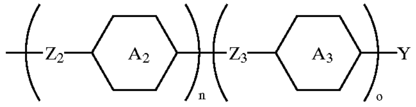 |
|---|---|---|---|
| 153 | $C_3H_7$— | 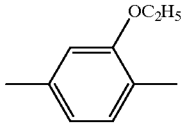 | 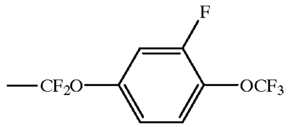 |
| 154 | $C_3H_7$— | 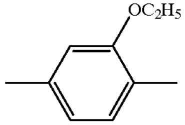 | 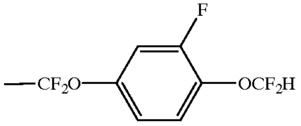 |
| 155 | $C_3H_7$— | 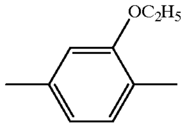 | 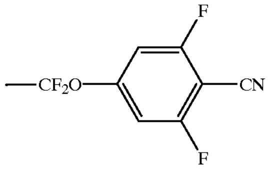 |
| 156 | $C_3H_7$— | 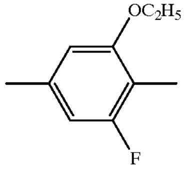 | 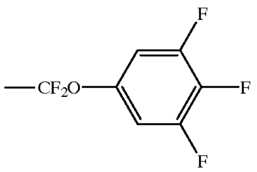 |
| 157 | $C_3H_7$— | 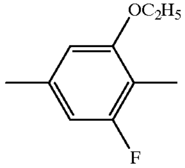 | 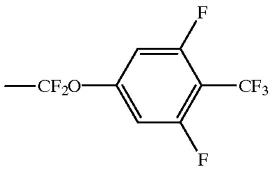 |

-continued
| No. | 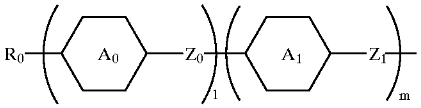 | 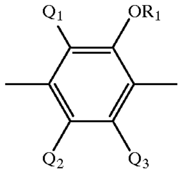 | 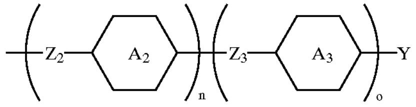 |
| --- | --- | --- | --- |
| 158 | $C_3H_7$— | 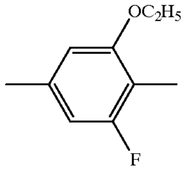 | 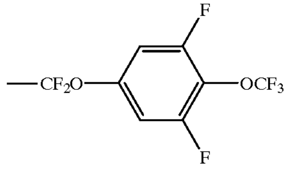 |
| 159 | 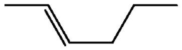 | 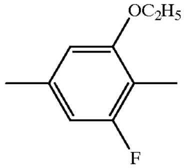 | 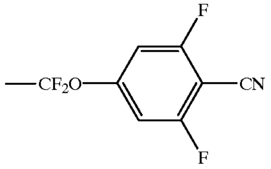 |
| 160 | $C_3H_7$— | 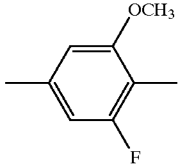 | 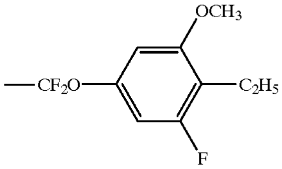 |
| 161 | $C_3H_7$— | 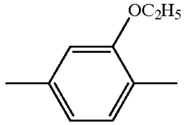 | 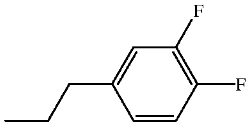 |
| 162 | $C_3H_7$— | 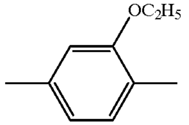 | 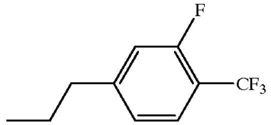 |

-continued
| No. | 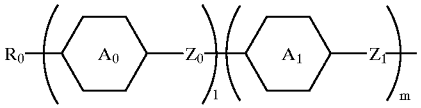 | 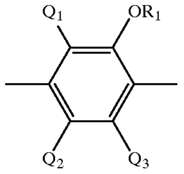 | 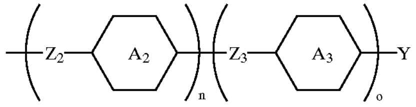 |
|---|---|---|---|
| 163 | $C_3H_7$— | 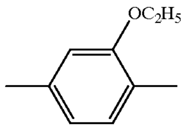 | 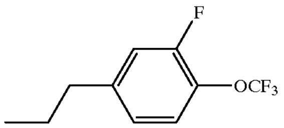 |
| 164 | $C_3H_7$— | 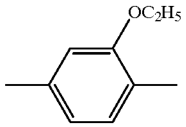 | 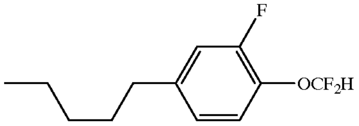 |
| 165 | $C_3H_7$— | 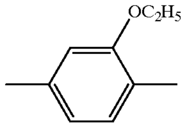 | 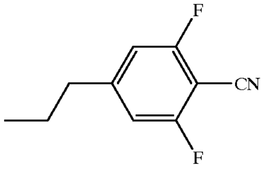 |
| 166 | $C_3H_7$— | 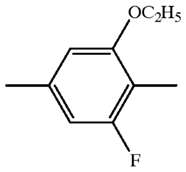 | 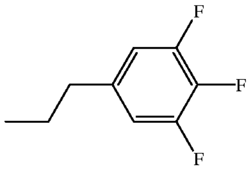 |
| 167 | $C_3H_7$— | 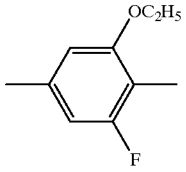 | 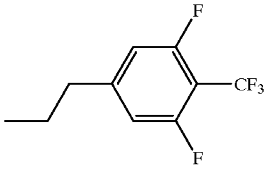 |

-continued
| No. | 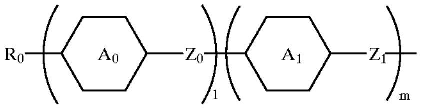 | 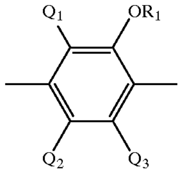 | 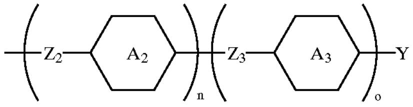 |
|---|---|---|---|
| 168 | $C_3H_7$— | 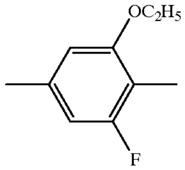 | 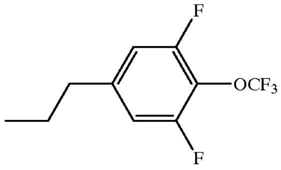 |
| 169 | 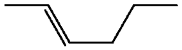 | 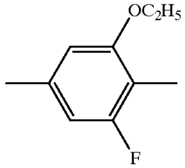 | 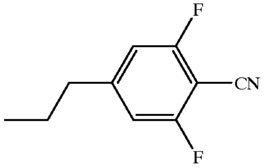 |
| 170 | $C_3H_7$— | 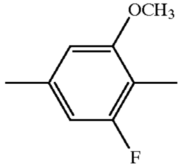 | 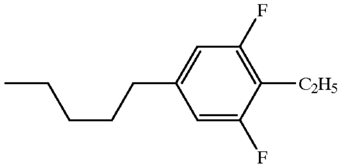 |
| 171 | $C_3H_7$— | 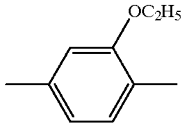 | 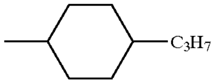 |
| 172 | $C_3H_7$— | 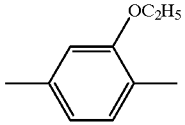 | 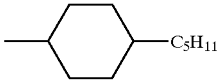 |

-continued
| No. | 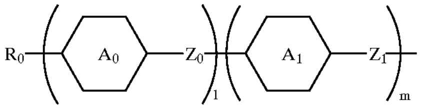 | 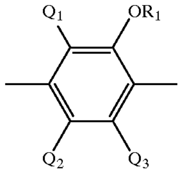 | 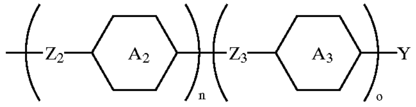 |
|---|---|---|---|
| 173 | $C_3H_7$— | 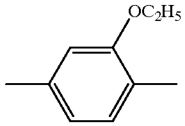 | 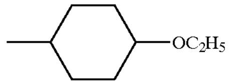 |
| 174 | $C_3H_7$— | 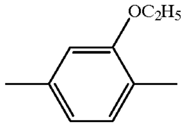 | 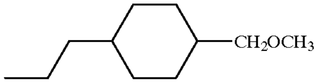 |
| 175 | $C_3H_7$— | 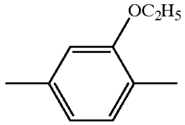 | 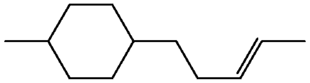 |
| 176 | $C_3H_7$— | 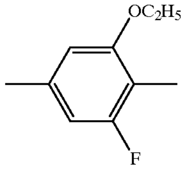 | 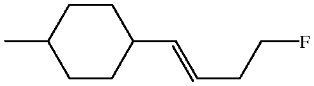 |
| 177 | $C_3H_7$— | 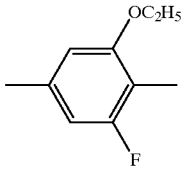 | 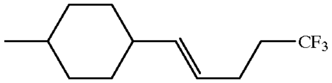 |

-continued
| No. | 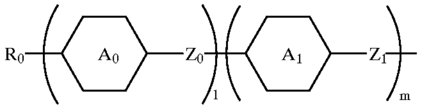 | 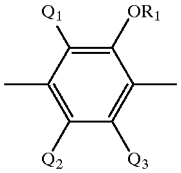 | 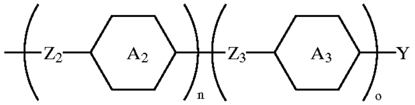 |
|---|---|---|---|
| 178 | $C_3H_7$— | 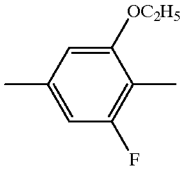 | 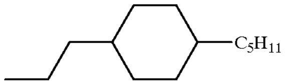 |
| 179 | 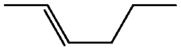 | 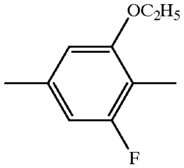 | 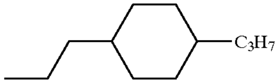 |
| 180 | $C_3H_7$— | 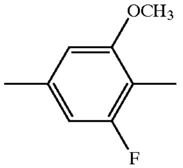 | 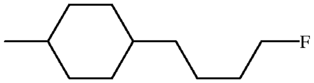 |
| 181 | 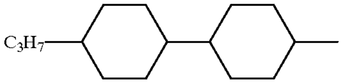 | 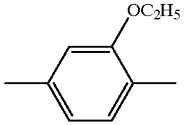 | —$C_3H_7$ |
| 182 | 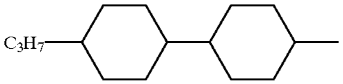 | 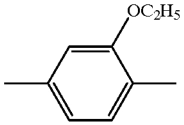 | —$C_5H_{11}$ |

-continued
| No. | 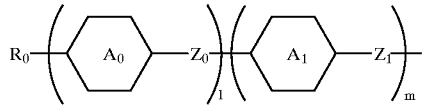 | 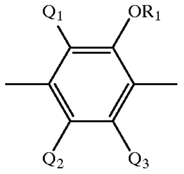 | 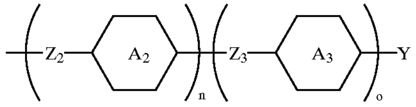 |
|---|---|---|---|
| 183 | 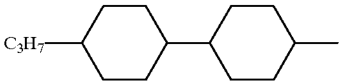 | 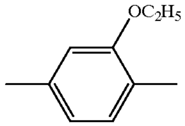 | $—OC_2H_5$ |
| 184 | 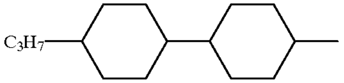 | 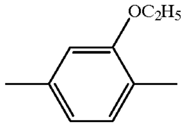 | $—CH_2OCH_3$ |
| 185 | 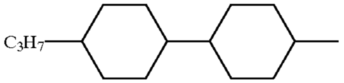 | 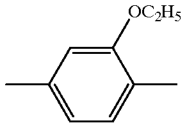 | 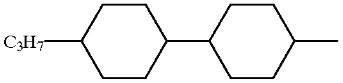 |
| 186 | 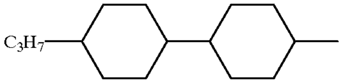 | 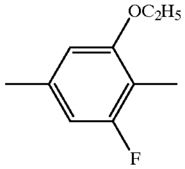 | 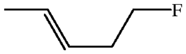 |
| 187 | 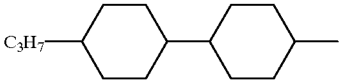 | 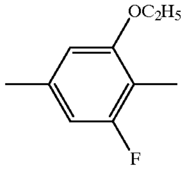 | 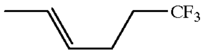 |

-continued
| No. | 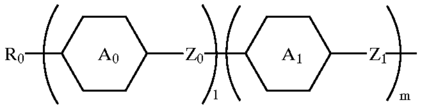 | 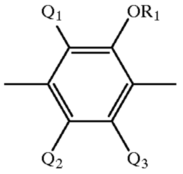 | 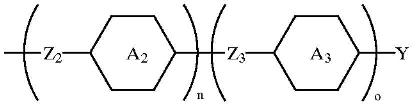 |
|---|---|---|---|
| 188 | 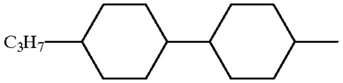 | 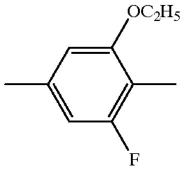 | $—C_5H_{11}$ |
| 189 | 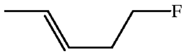 | 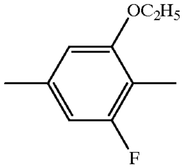 | $—C_3H_7$ |
| 190 | 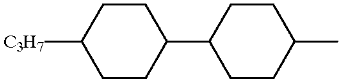 | 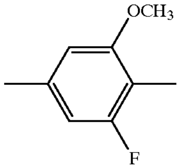 | 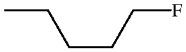 |
| 191 | 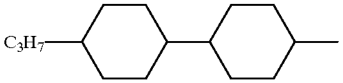 | 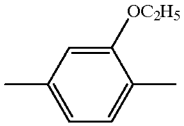 | —F |
| 192 | 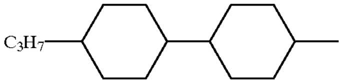 | 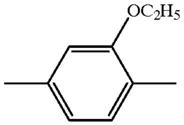 | $—CF_3$ |

-continued
| No. | 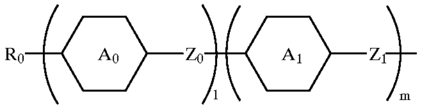 | 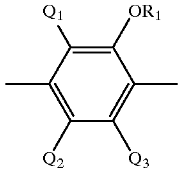 | 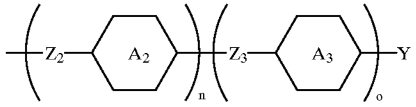 |
| --- | --- | --- | --- |
| 193 | 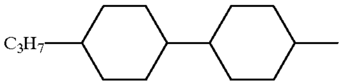 | 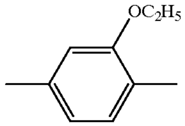 | $—OCF_3$ |
| 194 | 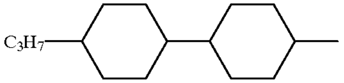 | 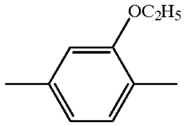 | —CN |
| 195 | 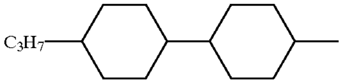 | 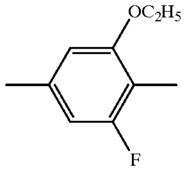 | —F |
| 196 | 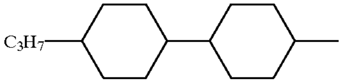 | 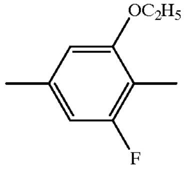 | $—CF_3$ |
| 197 | 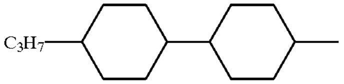 | 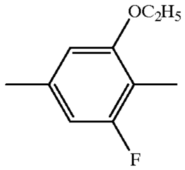 | $—OCF_3$ |

-continued
| No. | | | |
|---|---|---|---|
| | 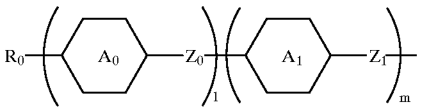 | 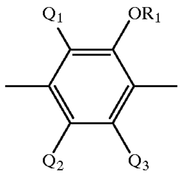 | 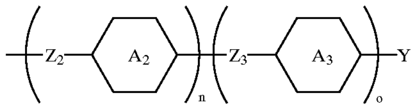 |
| 198 | 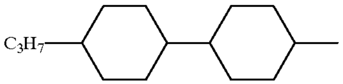 | 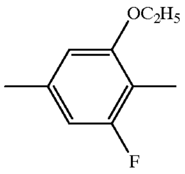 | —CN |
| 199 | 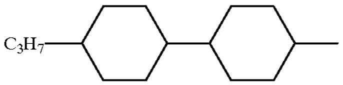 | 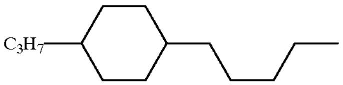 | —F |
| 200 | 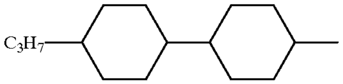 | 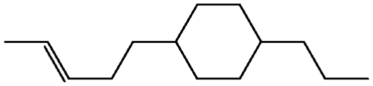 | —$OCF_3$ |
| 201 | 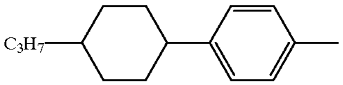 | 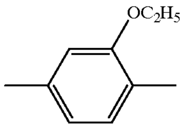 | —F |
| 202 | 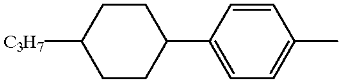 | 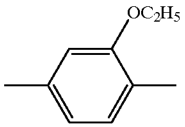 | —$CF_3$ |
| 203 | 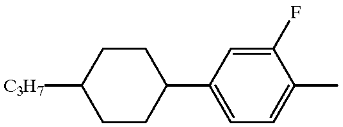 | 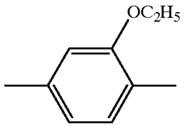 | —$OCF_3$ |

-continued
| No. | | | |
|---|---|---|---|
| | 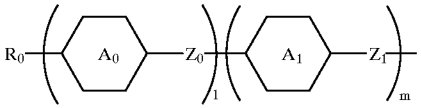 | 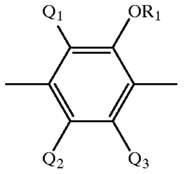 | 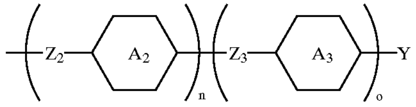 |
| 204 | 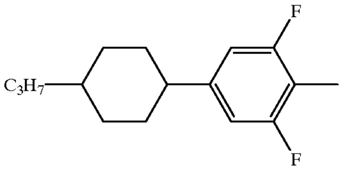 | 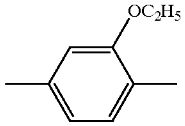 | —CN |
| 205 | 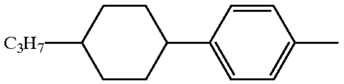 | 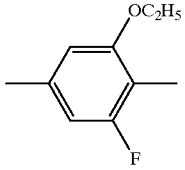 | —F |
| 206 | 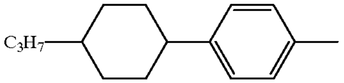 | 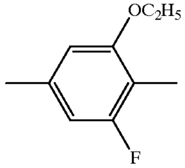 | $—CF_3$ |
| 207 | 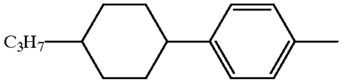 | 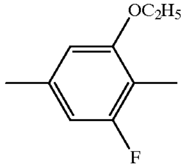 | $—OCF_3$ |

-continued
| No. | 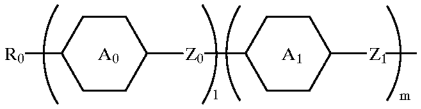 | 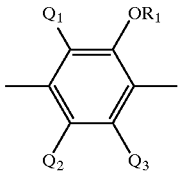 | 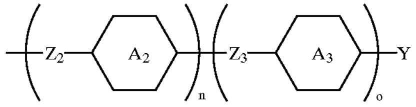 |
|---|---|---|---|
| 208 | 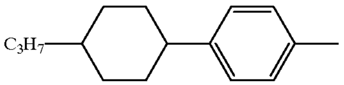 | 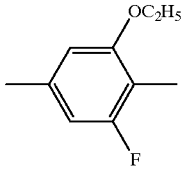 | —CN |
| 209 | 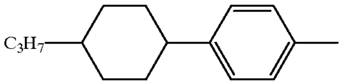 | 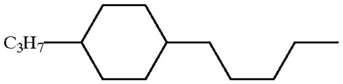 | —F |
| 210 | 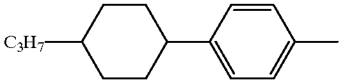 | 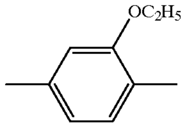 | —F |
| 211 | 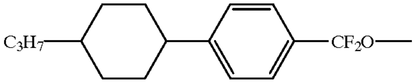 | 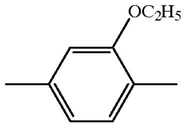 | —F |
| 212 | 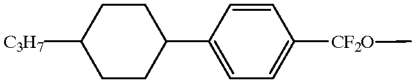 | 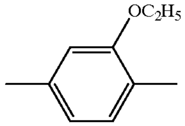 | $—CF_3$ |

-continued
| No. | 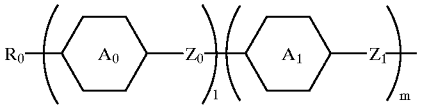 | 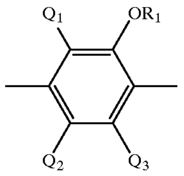 | 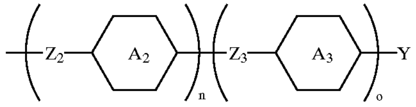 |
|---|---|---|---|
| 213 | 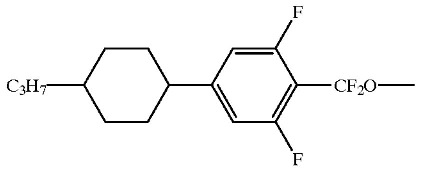 | 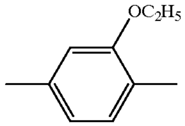 | $-OCF_3$ |
| 214 | 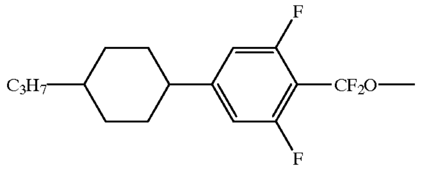 | 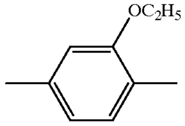 | $-CN$ |
| 215 | 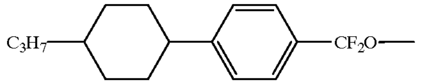 | 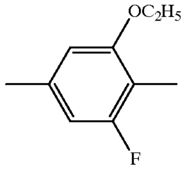 | $-F$ |
| 216 | 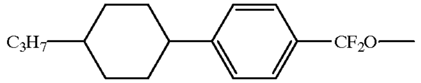 | 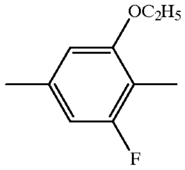 | $-CF_3$ |

-continued
| No. | | | |
|---|---|---|---|
| | 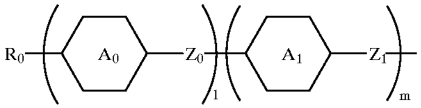 | 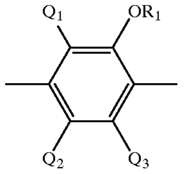 | 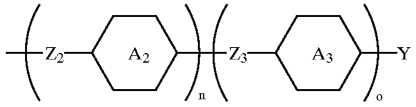 |
| 217 | 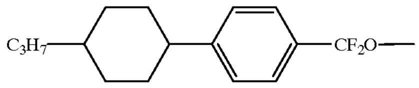 | 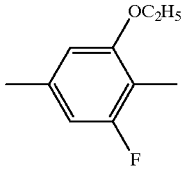 | —$OCF_3$ |
| 218 | 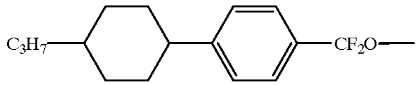 | 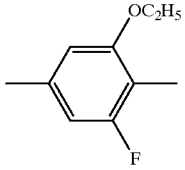 | —CN |
| 219 | 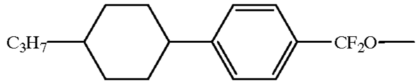 | 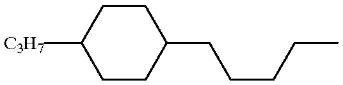 | —F |
| 220 | 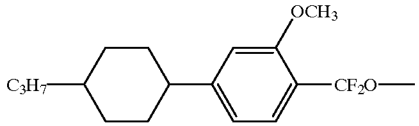 | 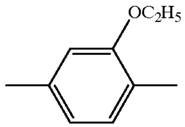 | —F |
| 221 | 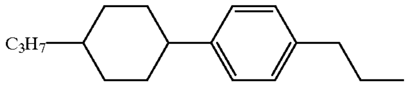 | 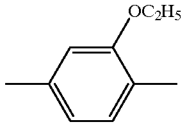 | —F |

-continued
| No. | | | |
|---|---|---|---|
| | 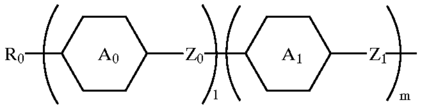 | 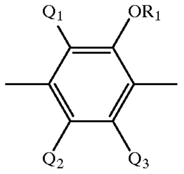 | 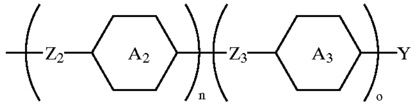 |
| 222 | 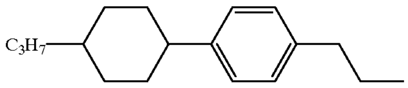 | 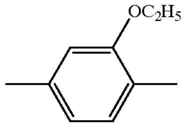 | $—CF_3$ |
| 223 | 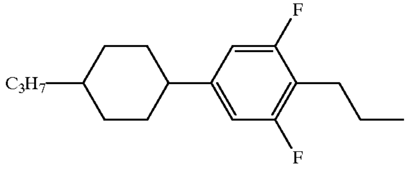 | 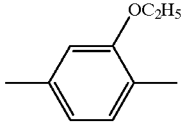 | $—OCF_3$ |
| 224 | 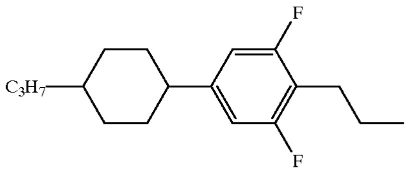 | 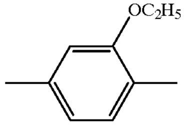 | —CN |
| 225 | 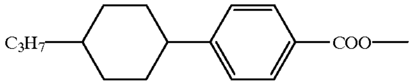 | 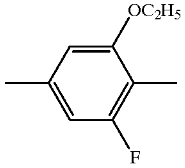 | —F |

-continued
| No. | 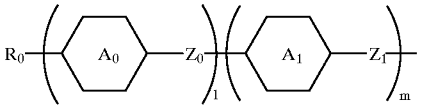 | 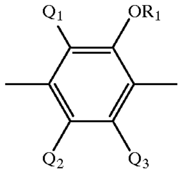 | 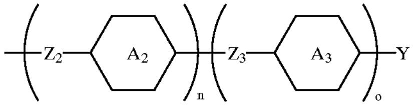 |
| --- | --- | --- | --- |
| 226 | 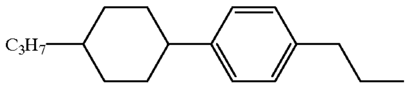 | 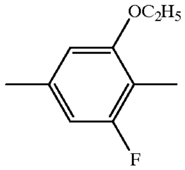 | —$CF_3$ |
| 227 | 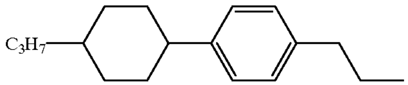 | 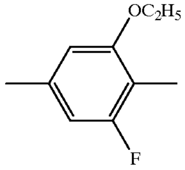 | —$OCF_3$ |
| 228 | 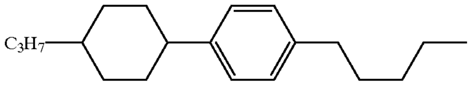 | 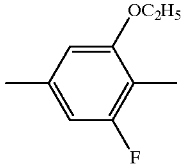 | —CN |
| 229 | 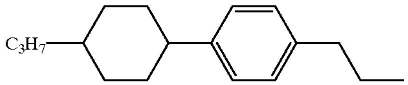 | 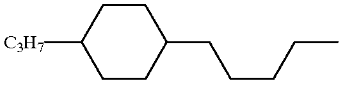 | —F |
| 230 | 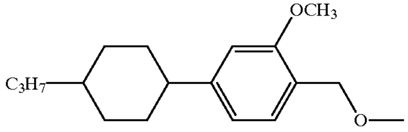 | 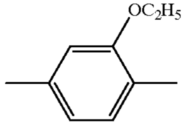 | —F |

-continued
| No. | 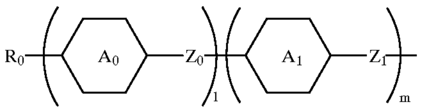 | 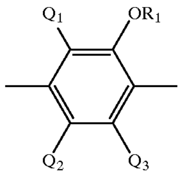 | 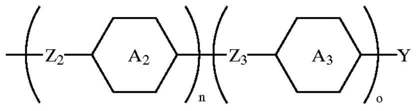 |
|---|---|---|---|
| 231 | 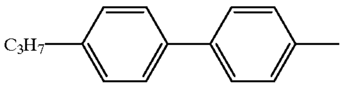 | 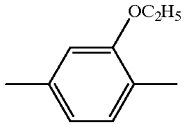 | —F |
| 232 | 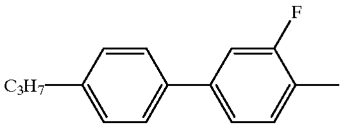 | 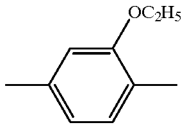 | —$CF_3$ |
| 233 | 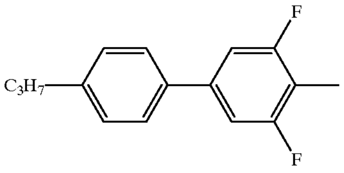 | 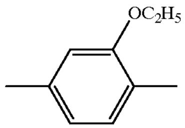 | —$OCF_3$ |
| 234 | 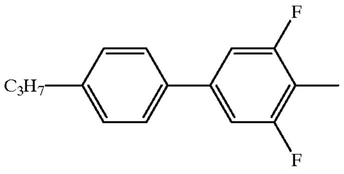 | 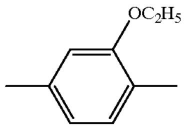 | —CN |
| 235 | 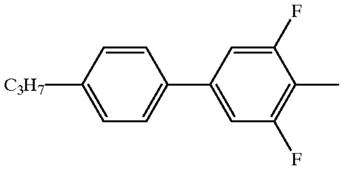 | 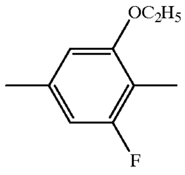 | —F |

-continued
| No. | 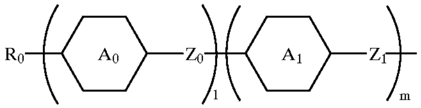 | 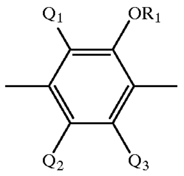 | 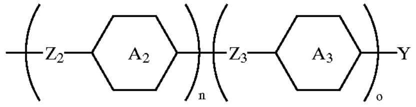 |
|---|---|---|---|
| 236 | 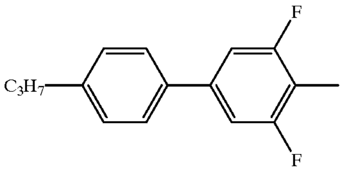 | 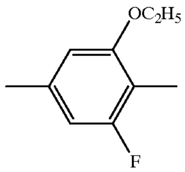 | $-CF_3$ |
| 237 | 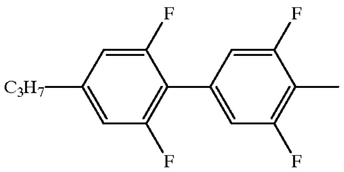 | 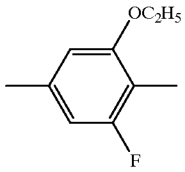 | $-OCF_3$ |
| 238 | 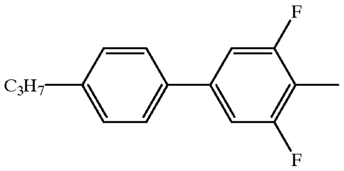 | 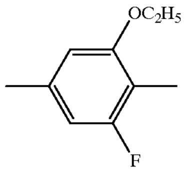 | $-CN$ |
| 239 | 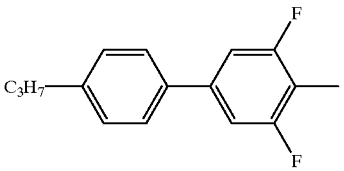 | 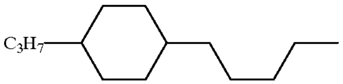 | $-F$ |

-continued
| No. | | | |
|---|---|---|---|
| | 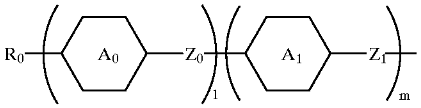 | 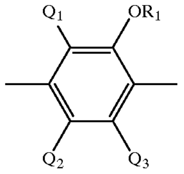 | 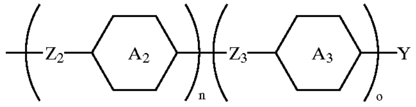 |
| 240 | 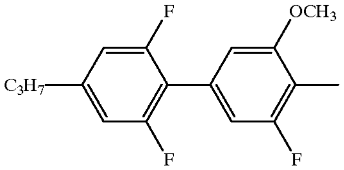 | 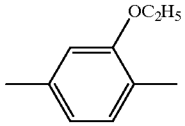 | —F |
| 241 | 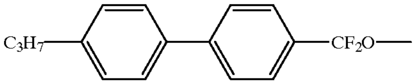 | 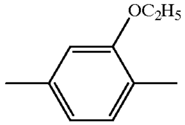 | —F |
| 242 | 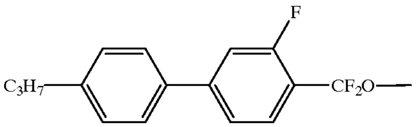 | 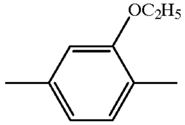 | —$CF_3$ |
| 243 | 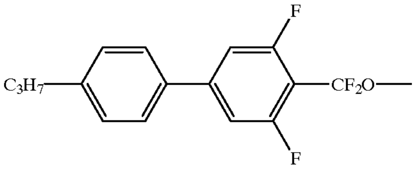 | 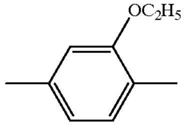 | —$OCF_3$ |
| 244 | 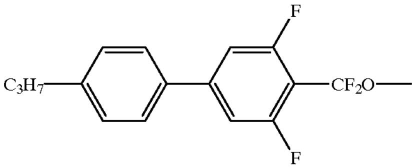 | 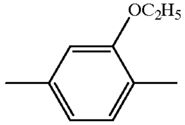 | —CN |

-continued
| No. | | | |
|---|---|---|---|
| | 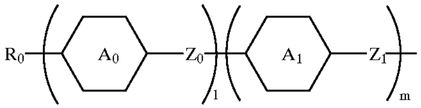 | 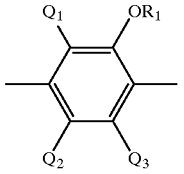 | 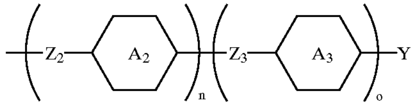 |
| 245 | 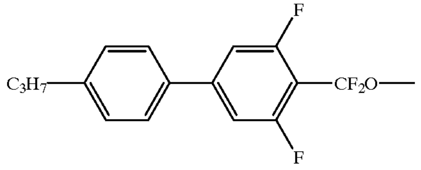 | 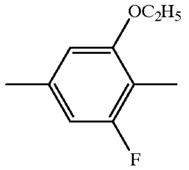 | —F |
| 246 | 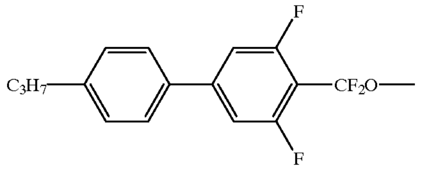 | 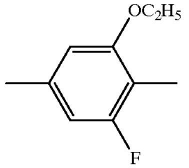 | $—CF_3$ |
| 247 | 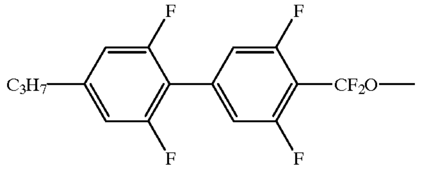 | 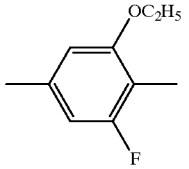 | $—OCF_3$ |
| 248 | 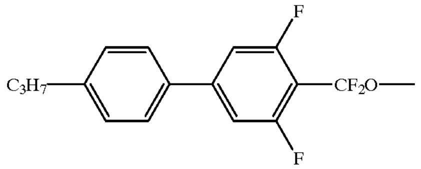 | 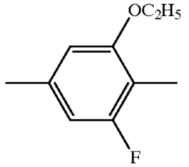 | —CN |

-continued
| No. | 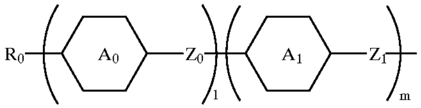 | 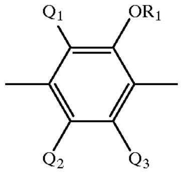 | 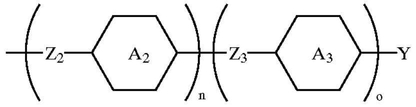 |
|---|---|---|---|
| 249 | 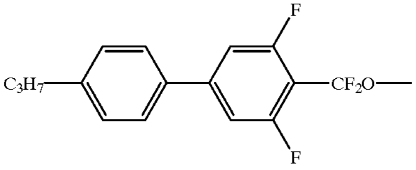 | 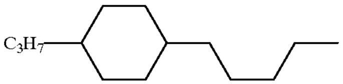 | —F |
| 250 | 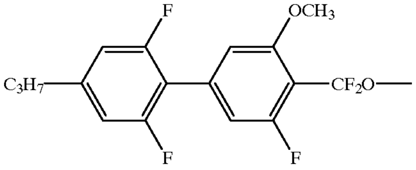 | 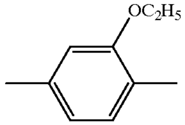 | —F |
| 251 | 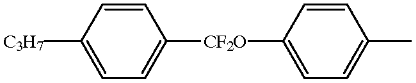 | 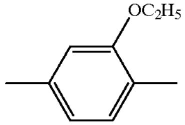 | —F |
| 252 | 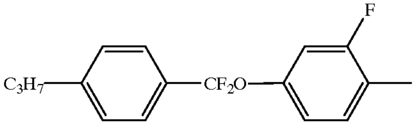 | 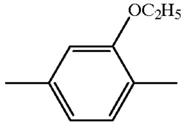 | $—CF_3$ |
| 253 | 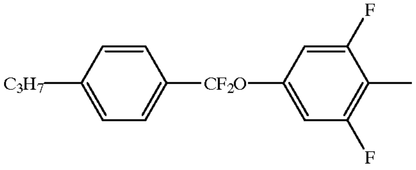 | 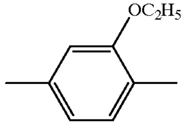 | $—OCF_3$ |

-continued
| No. | | | |
|---|---|---|---|
| | 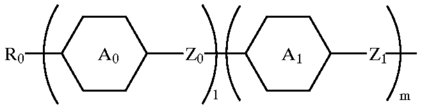 | 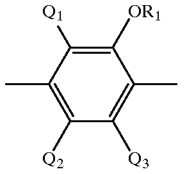 | 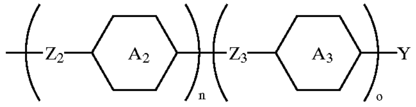 |
| 254 | 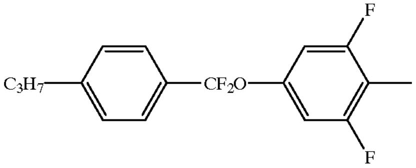 | 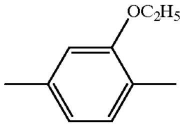 | —CN |
| 255 | 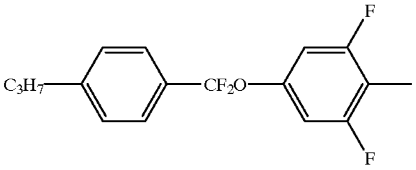 | 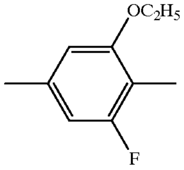 | —F |
| 256 | 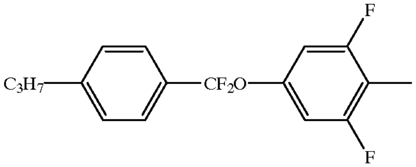 | 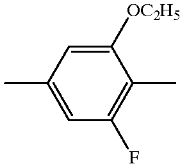 | —$CF_3$ |
| 257 | 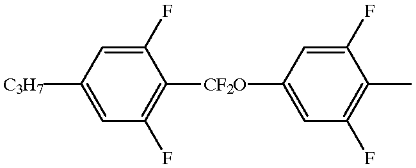 | 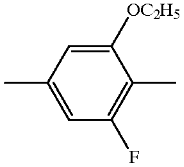 | —$OCF_3$ |

-continued
| No. | 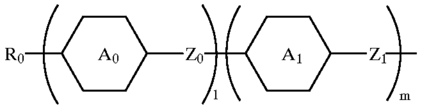 | 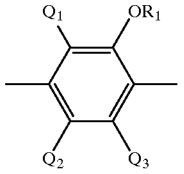 | 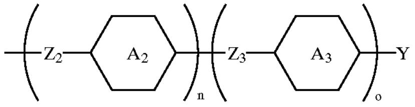 |
|---|---|---|---|
| 258 | 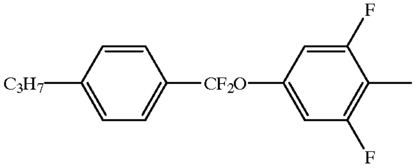 | 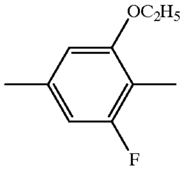 | —CN |
| 259 | 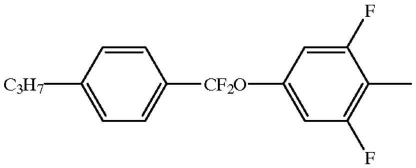 | 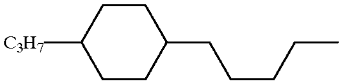 | —F |
| 260 | 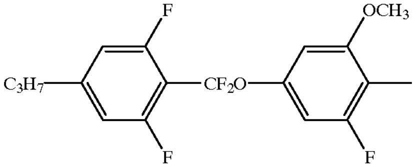 | 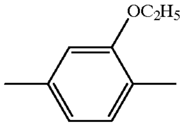 | —F |
| 261 | 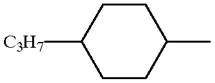 | 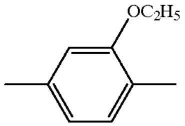 | 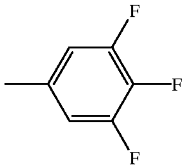 |

-continued
| No. | 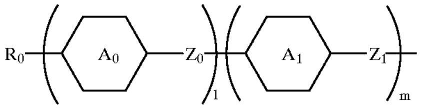 | 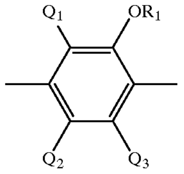 | 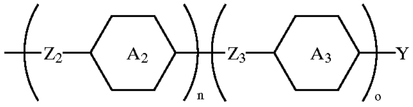 |
|---|---|---|---|
| 262 | 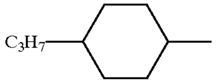 | 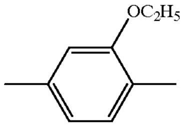 | 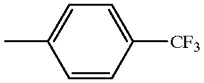 |
| 263 | 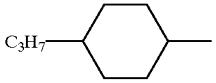 | 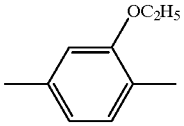 | 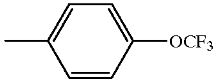 |
| 264 | 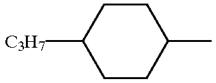 | 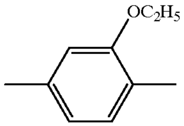 | 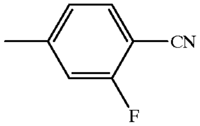 |
| 265 | 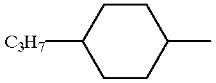 | 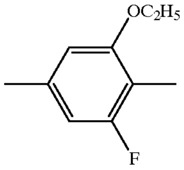 | 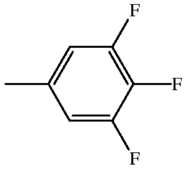 |
| 266 | 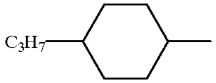 | 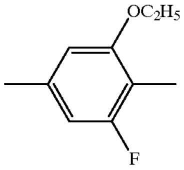 | 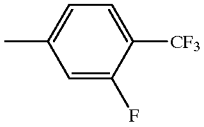 |

-continued
| No. | | | |
|---|---|---|---|
| | 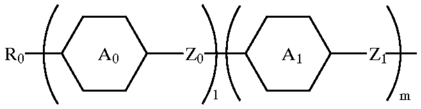 | 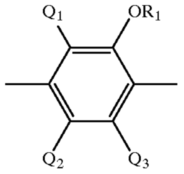 | 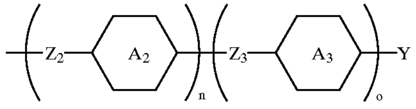 |
| 267 | 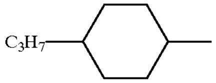 | 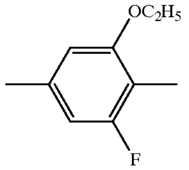 | 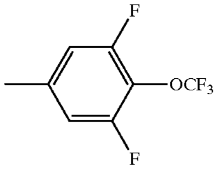 |
| 268 | 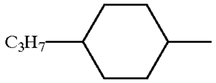 | 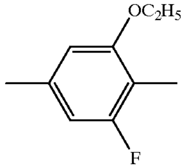 | 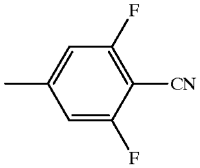 |
| 269 | 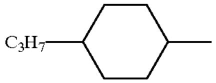 | 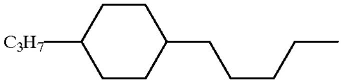 | 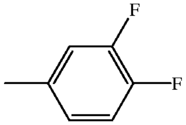 |
| 270 | 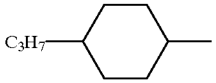 | 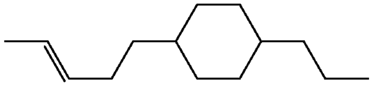 | 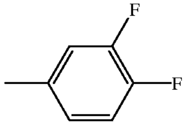 |
| 271 | 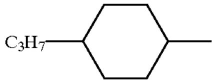 | 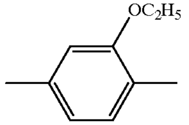 | 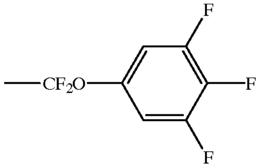 |

-continued
| No. | 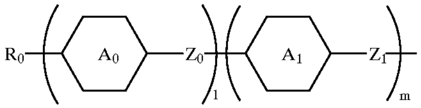 | 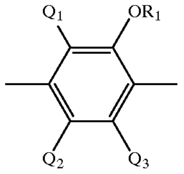 | 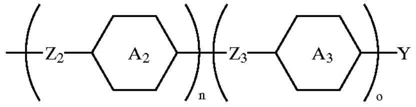 |
|---|---|---|---|
| 272 | 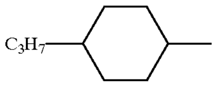 | 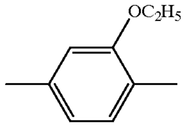 | 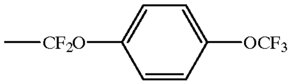 |
| 273 | 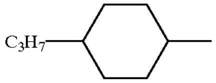 | 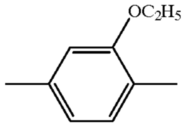 | 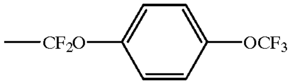 |
| 274 | 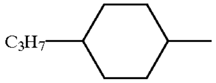 | 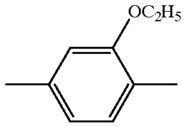 | 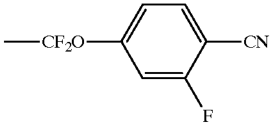 |
| 275 | 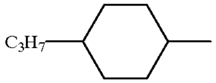 | 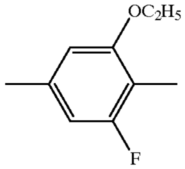 | 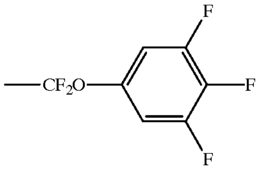 |
| 276 | 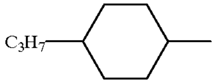 | 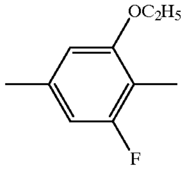 | 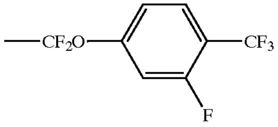 |

-continued
| No. | | | |
|---|---|---|---|
| No. | 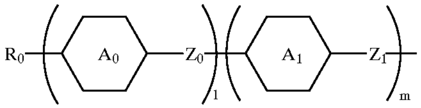 | 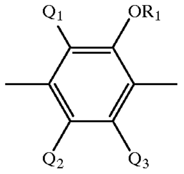 | 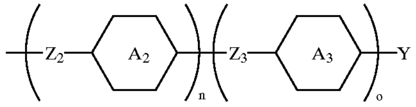 |
| 277 | 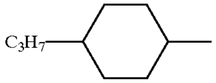 | 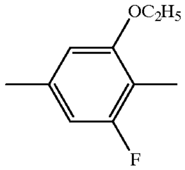 | 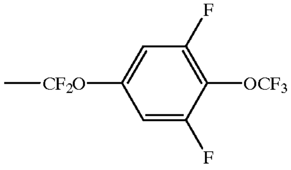 |
| 278 | 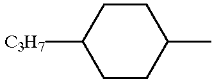 | 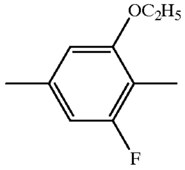 | 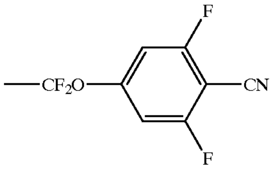 |
| 279 | 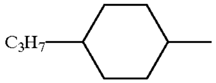 | 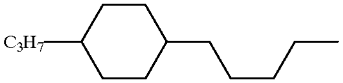 | 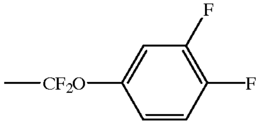 |
| 280 | 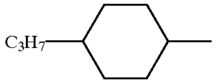 | 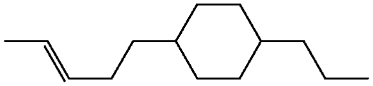 | 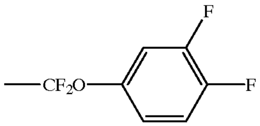 |
| 281 | 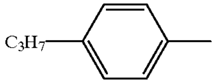 | 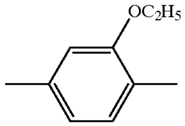 | 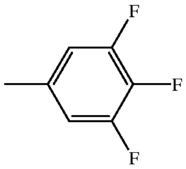 |

-continued
| No. | | | |
|---|---|---|---|
| | 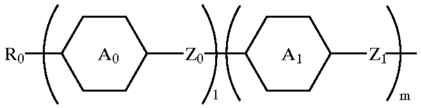 | 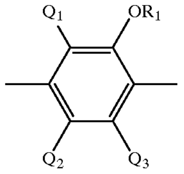 | 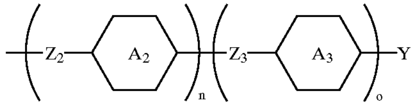 |
| 282 | 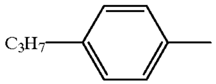 | 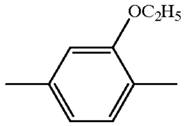 | 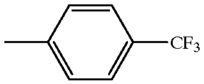 |
| 283 | 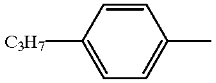 | 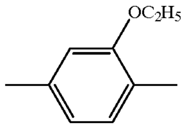 | 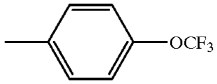 |
| 284 | 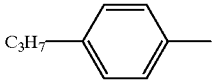 | 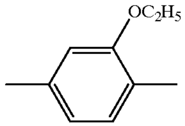 | 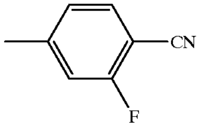 |
| 285 | 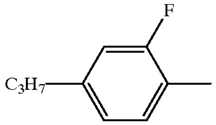 | 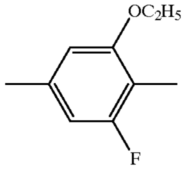 | 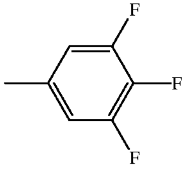 |
| 286 | 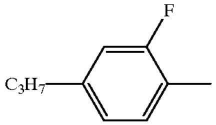 | 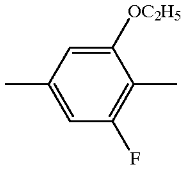 | 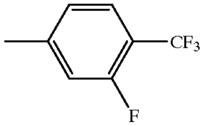 |

-continued
| No. | | | |
| --- | --- | --- | --- |
| | 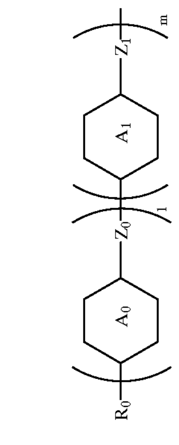 | 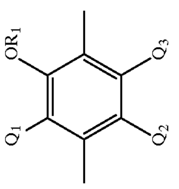 | 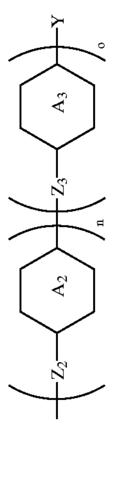 |
| 287 | 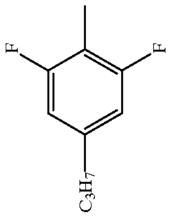 | 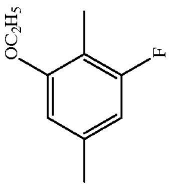 | 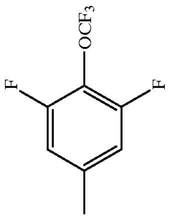 |
| 288 | 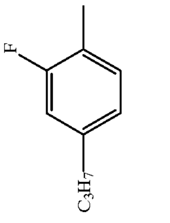 | 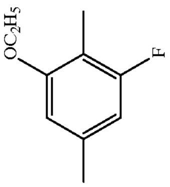 | 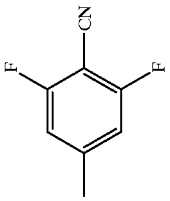 |
| 289 | 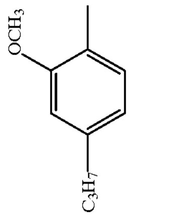 | 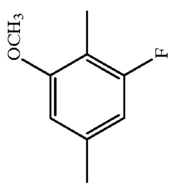 | 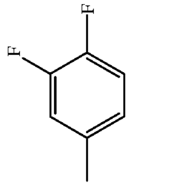 |
| 290 | 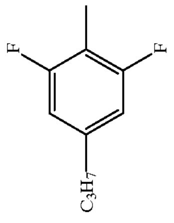 | 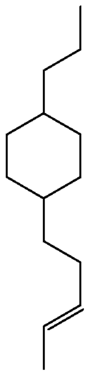 | 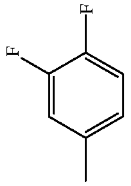 |

-continued
| No. | | | |
|---|---|---|---|
| | 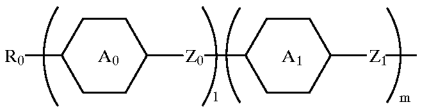 | 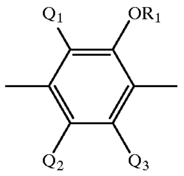 | 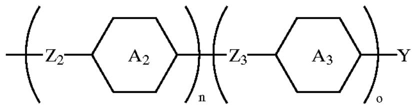 |
| 291 | 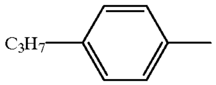 | 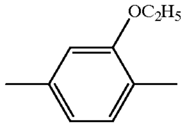 | 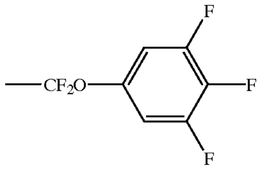 |
| 292 | 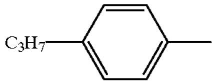 | 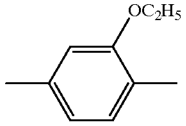 | 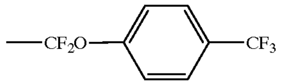 |
| 293 | 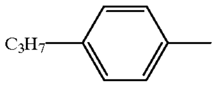 | 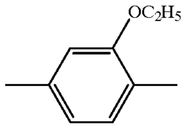 | 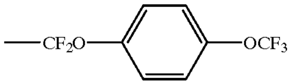 |
| 294 | 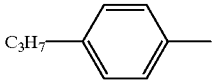 | 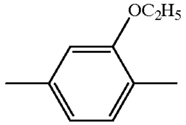 | 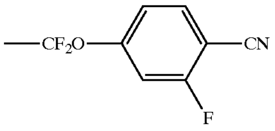 |
| 295 | 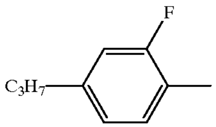 | 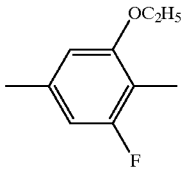 | 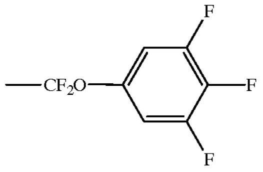 |

-continued
| No. | | | |
|---|---|---|---|
| | 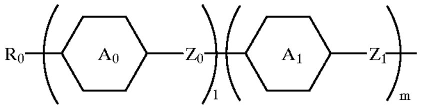 | 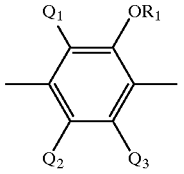 | 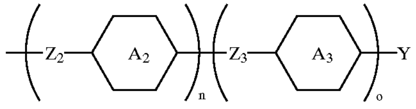 |
| 296 | 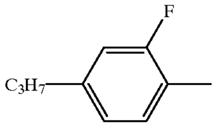 | 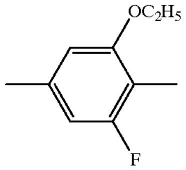 | 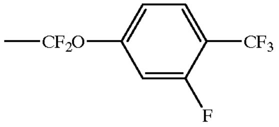 |
| 297 | 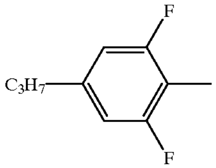 | 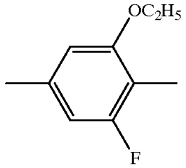 | 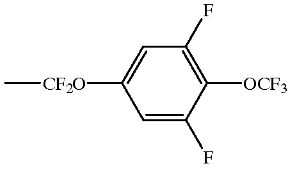 |
| 298 | 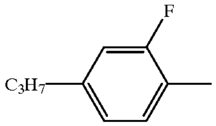 | 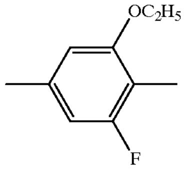 | 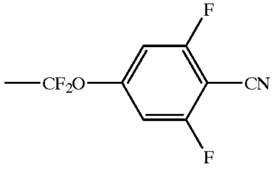 |
| 299 | 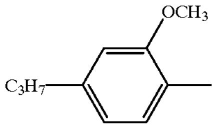 | 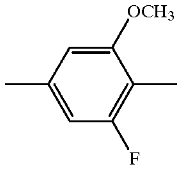 | 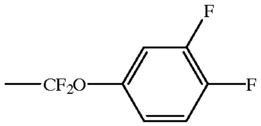 |

-continued
| No. | 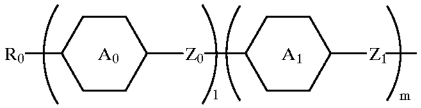 | 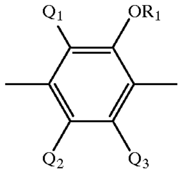 | 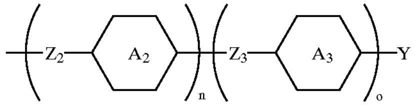 |
|---|---|---|---|
| 300 | 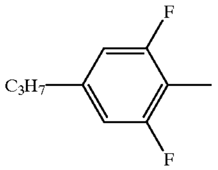 | 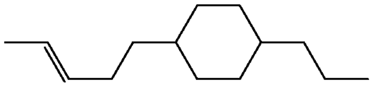 | 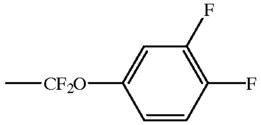 |
| 301 | 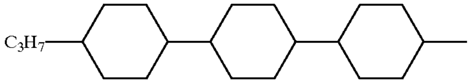 | 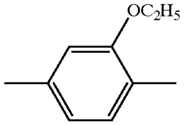 | $-F$ |
| 302 | 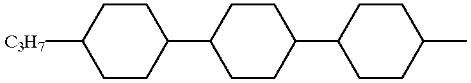 | 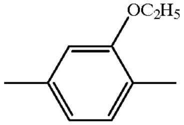 | $-CF_3$ |
| 303 | 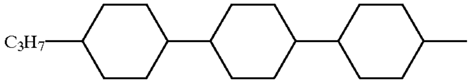 | 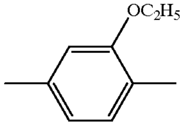 | $-OCF_3$ |
| 304 | 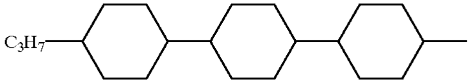 | 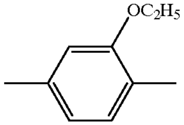 | $-CN$ |

-continued
| No. | | | |
|---|---|---|---|
| | 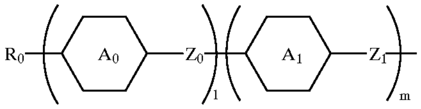 | 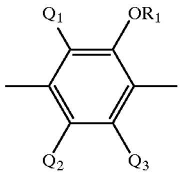 | 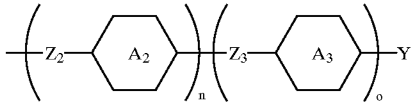 |
| 305 | 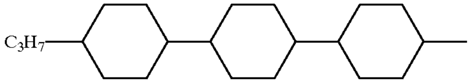 | 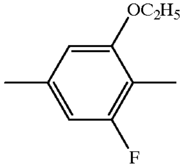 | —F |
| 306 | 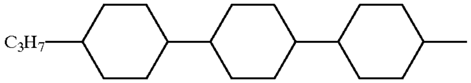 | 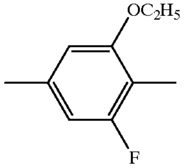 | $—CF_3$ |
| 307 | 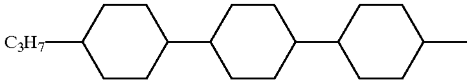 | 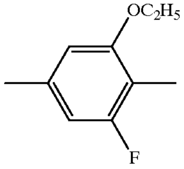 | $—OCF_3$ |
| 308 | 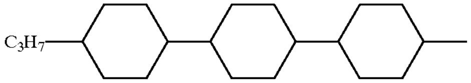 | 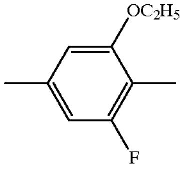 | —CN |

-continued
| No. | 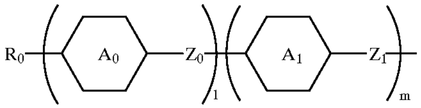 | 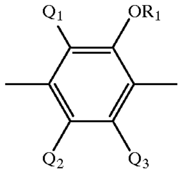 | 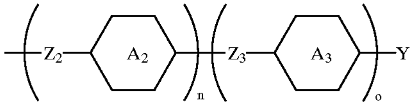 |
|---|---|---|---|
| 309 | 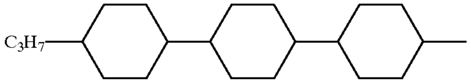 | 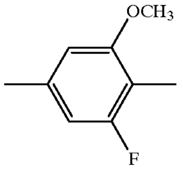 | —$C_5H_{11}$ |
| 310 | 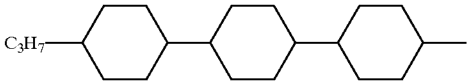 | 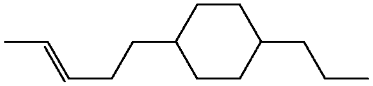 | —F |
| 311 | 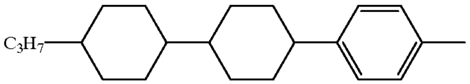 | 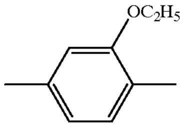 | —F |
| 312 | 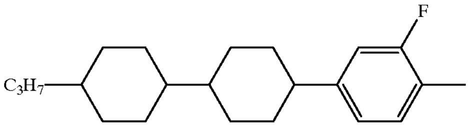 | 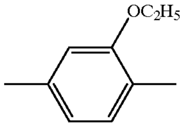 | —$CF_3$ |
| 313 | 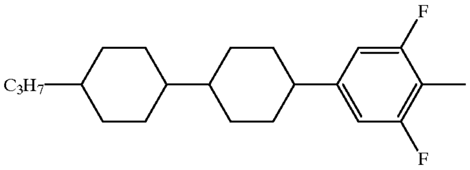 | 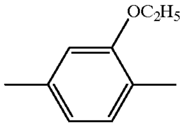 | —$OCF_3$ |

-continued
| No. | | | |
|---|---|---|---|
| | 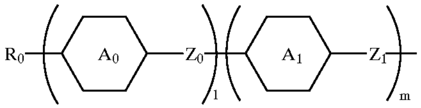 | 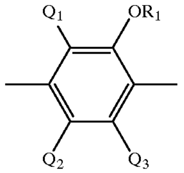 | 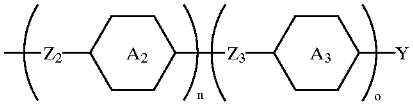 |
| 314 | 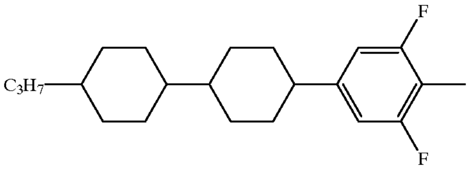 | 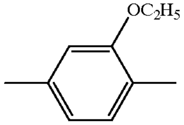 | —CN |
| 315 | 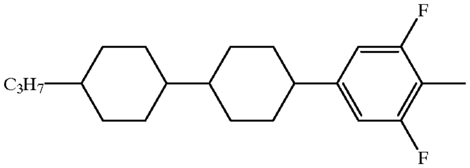 | 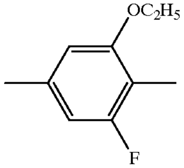 | —F |
| 316 | 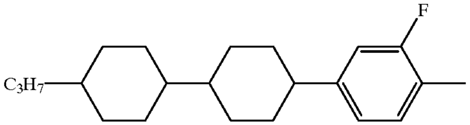 | 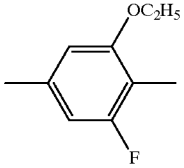 | —$CF_3$ |
| 317 | 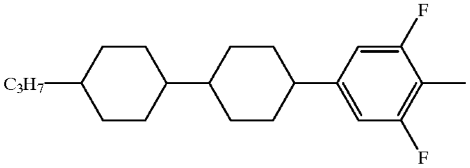 | 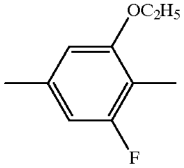 | —$OCF_3$ |

-continued
| No. | | | |
|---|---|---|---|
| | 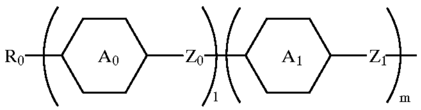 | 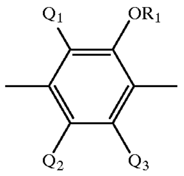 | 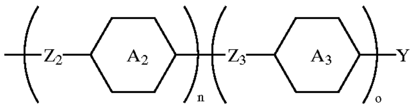 |
| 318 | 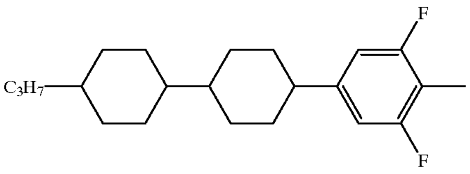 | 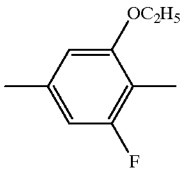 | $—CN$ |
| 319 | 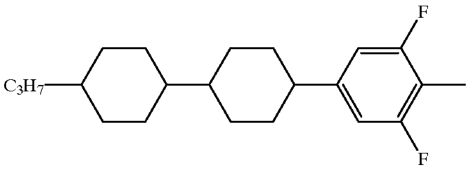 | 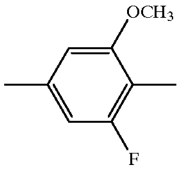 | $—C_5H_{11}$ |
| 320 | 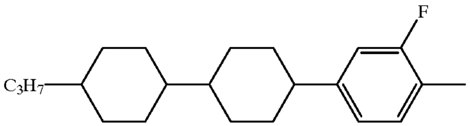 | 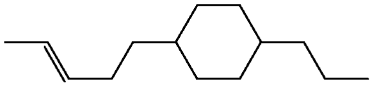 | —F |
| 321 | 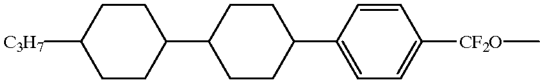 | 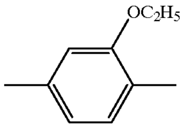 | —F |
| 322 | 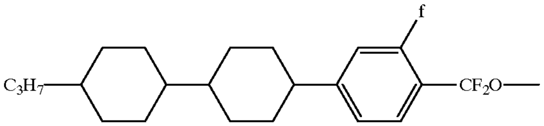 | 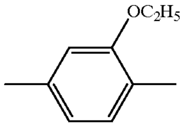 | $—CF_3$ |

-continued
| No. | | | |
|---|---|---|---|
| | 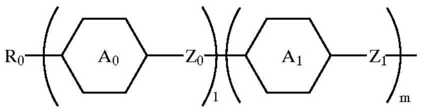 | 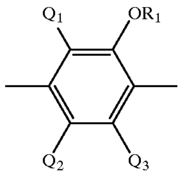 | 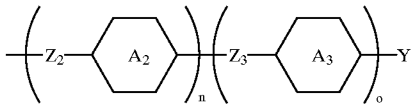 |
| 323 | 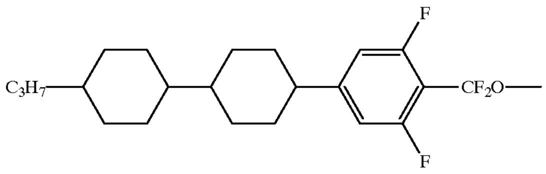 | 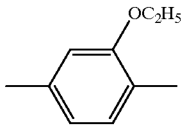 | $—OCF_3$ |
| 324 | 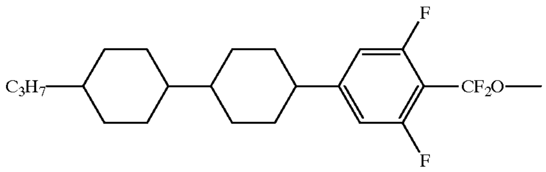 | 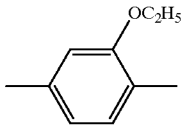 | —CN |
| 325 | 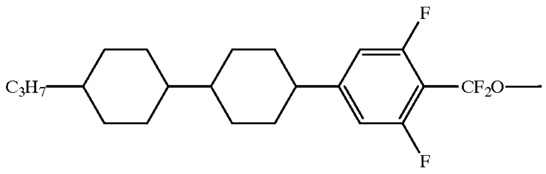 | 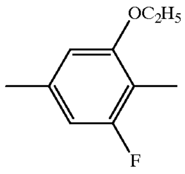 | —F |
| 326 | 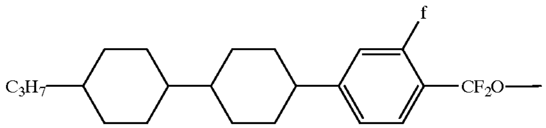 | 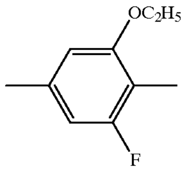 | $—CF_3$ |

-continued
| No. | 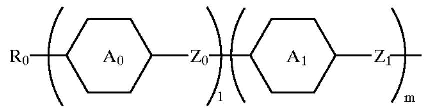 | 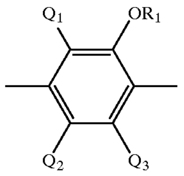 | 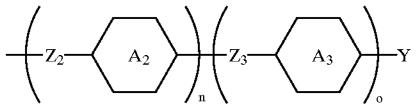 |
|---|---|---|---|
| 327 | 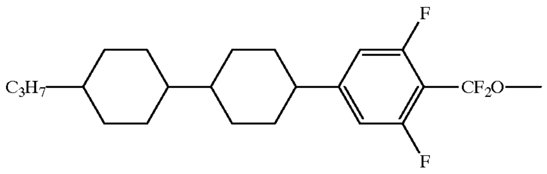 | 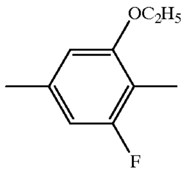 | $—OCF_3$ |
| 328 | 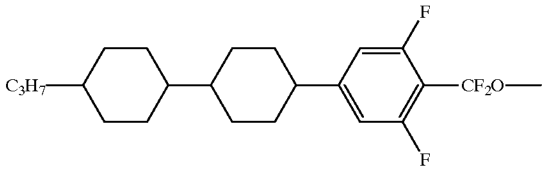 | 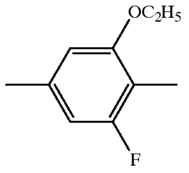 | —CN |
| 329 | 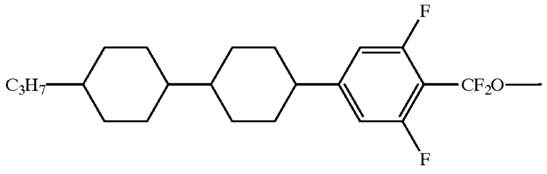 | 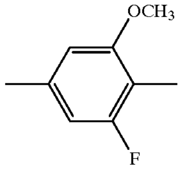 | $—C_5H_{11}$ |
| 330 | 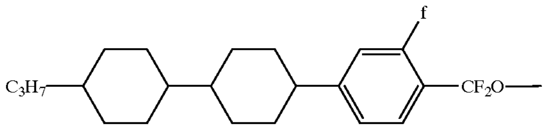 | 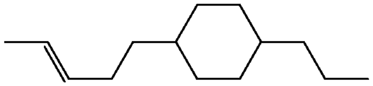 | —F |
| 331 | 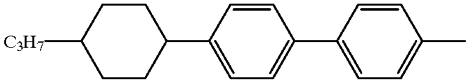 | 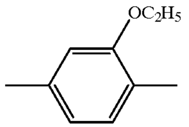 | —F |

-continued
| No. | 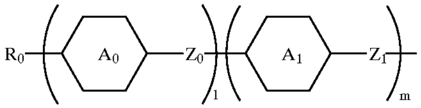 | 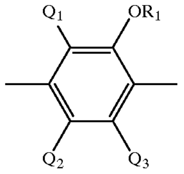 | 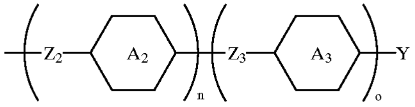 |
|---|---|---|---|
| 332 | 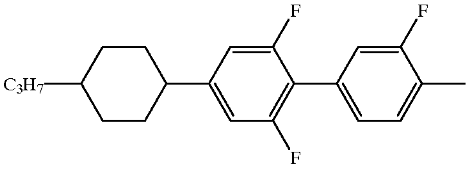 | 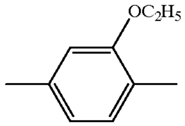 | $—CF_3$ |
| 333 | 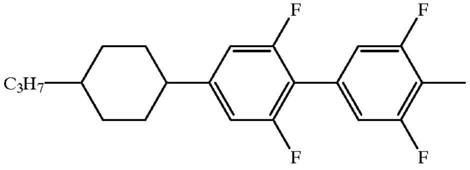 | 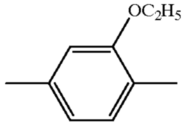 | $—OCF_3$ |
| 334 | 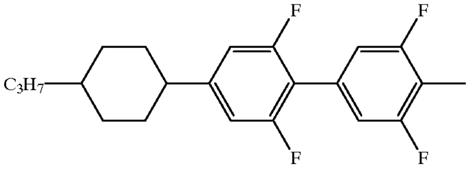 | 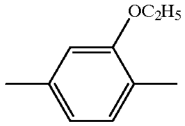 | —CN |
| 335 | 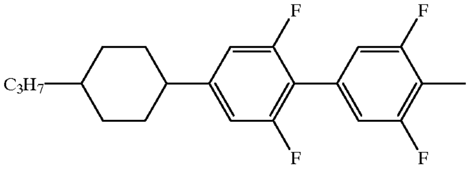 | 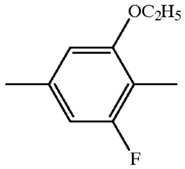 | —F |

-continued
| No. | 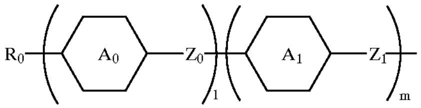 | 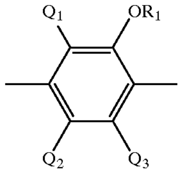 | 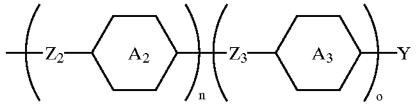 |
|---|---|---|---|
| 336 | 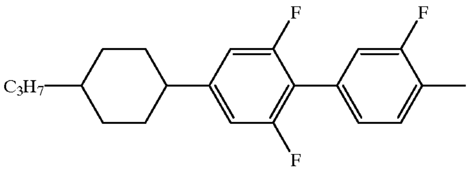 | 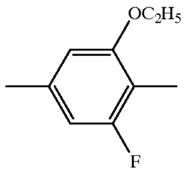 | $—CF_3$ |
| 337 | 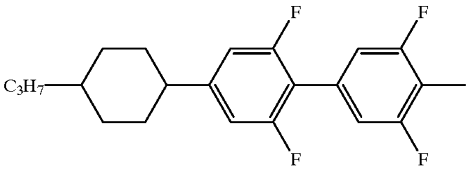 | 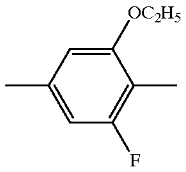 | $—OCF_3$ |
| 338 | 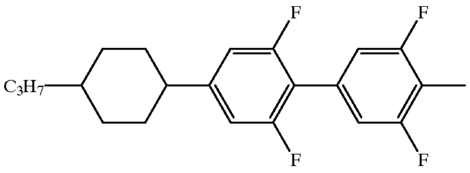 | 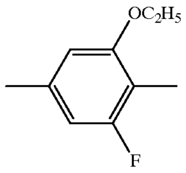 | —CN |
| 339 | 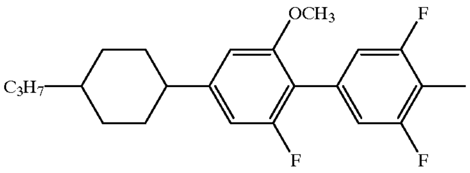 | 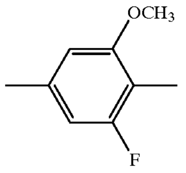 | $—C_5H_{11}$ |

-continued
| No. | 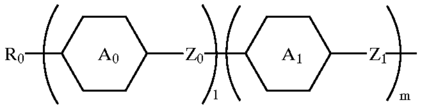 | 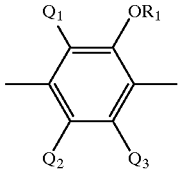 | 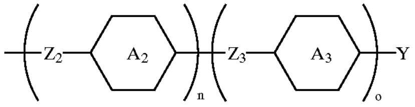 |
|---|---|---|---|
| 340 | 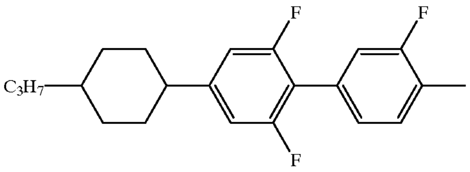 | 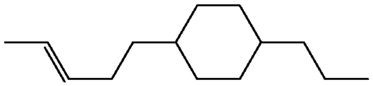 | —F |
| 341 | 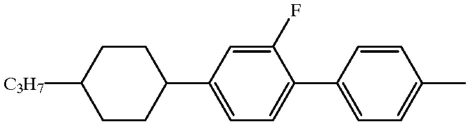 | 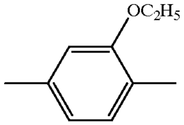 | —F |
| 342 | 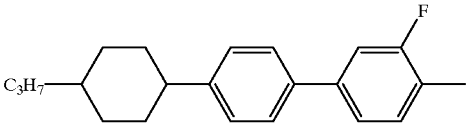 | 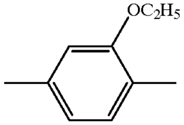 | $—CF_3$ |
| 343 | 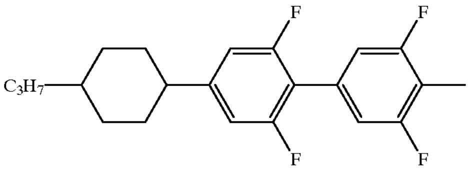 | 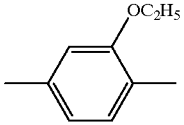 | $—OCF_3$ |
| 344 | 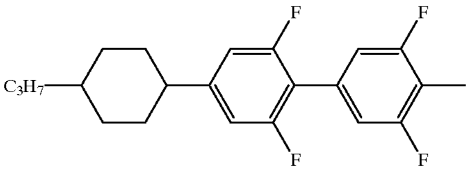 | 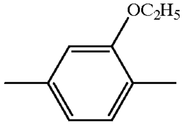 | —CN |

-continued
| No. | 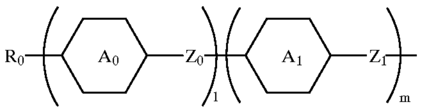 | 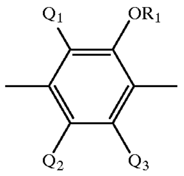 | 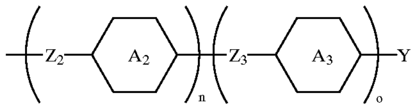 |
| --- | --- | --- | --- |
| 345 | 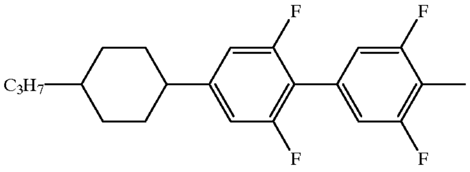 | 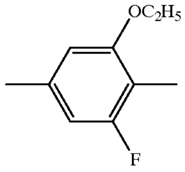 | —F |
| 346 | 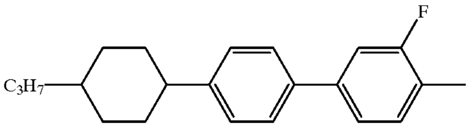 | 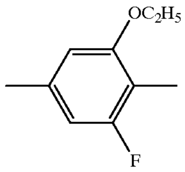 | —$CF_3$ |
| 347 | 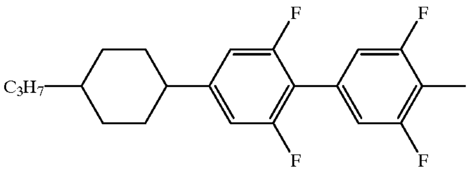 | 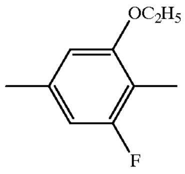 | —$OCF_3$ |
| 348 | 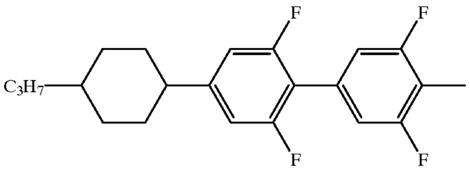 | 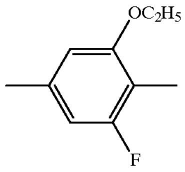 | —CN |

-continued
| No. | 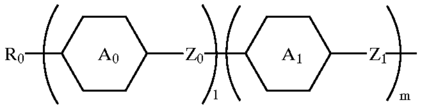 | 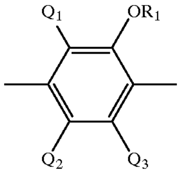 | 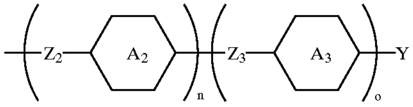 |
|---|---|---|---|
| 349 | 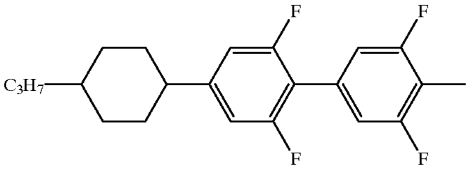 | 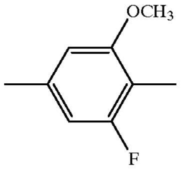 | $—C_5H_{11}$ |
| 350 | 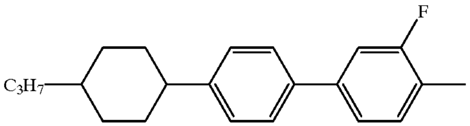 | 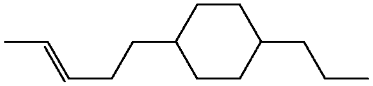 | —F |
| 351 | 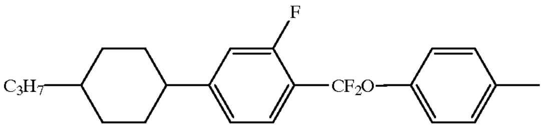 | 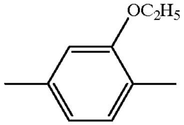 | —F |
| 352 | 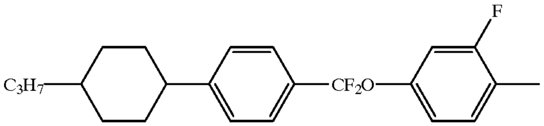 | 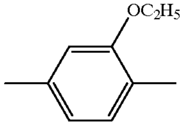 | $—CF_3$ |
| 353 | 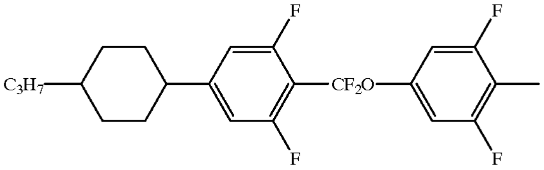 | 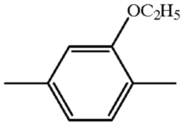 | $—OCF_3$ |

-continued
| No. | 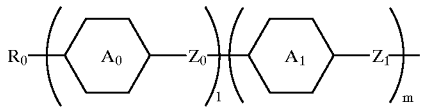 | 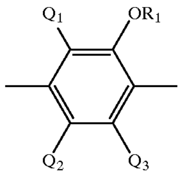 | 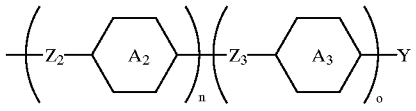 |
| --- | --- | --- | --- |
| 354 | 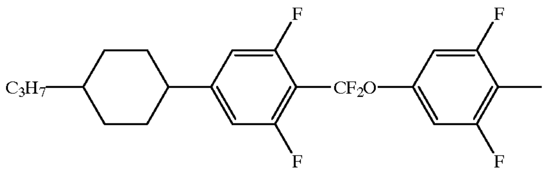 | 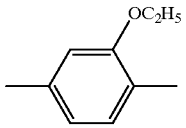 | $—CN$ |
| 355 | 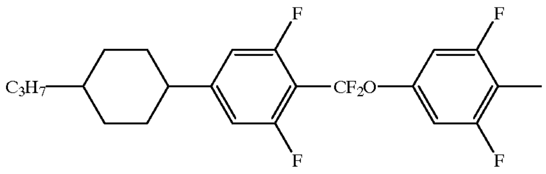 | 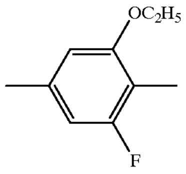 | $—F$ |
| 356 | 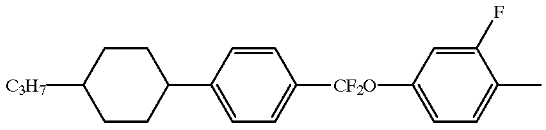 | 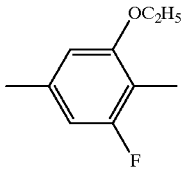 | $—CF_3$ |
| 357 | 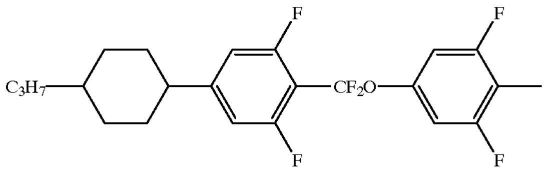 | 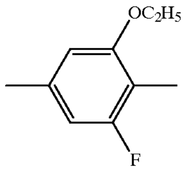 | $—OCF_3$ |

-continued
| No. | 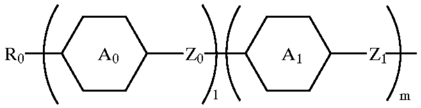 | 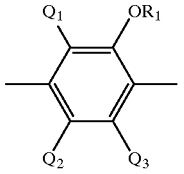 | 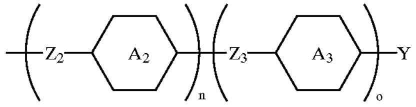 |
|---|---|---|---|
| 358 | 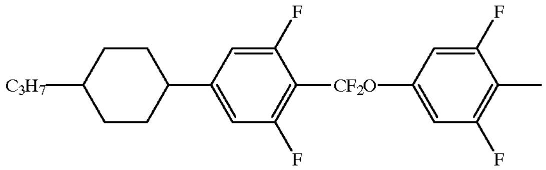 | 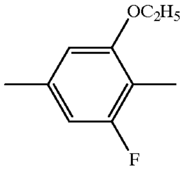 | —CN |
| 359 | 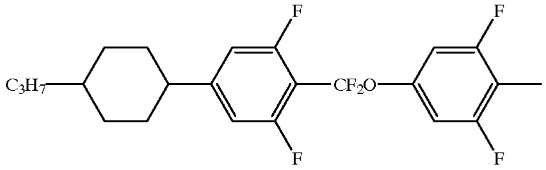 | 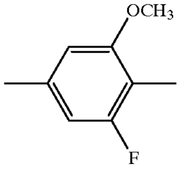 | —$C_5H_{11}$ |
| 360 | 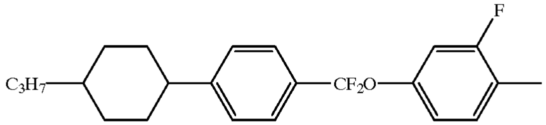 | 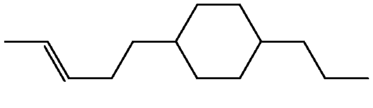 | —F |
| 361 | 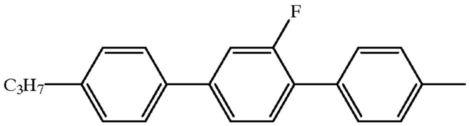 | 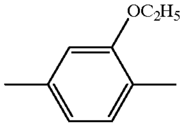 | —F |
| 362 | 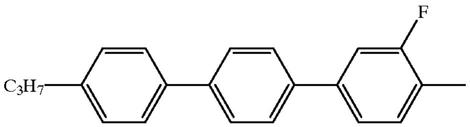 | 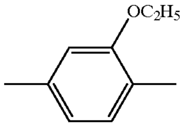 | —$CF_3$ |

-continued
| No. | | | |
|---|---|---|---|
| | 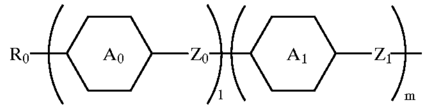 | 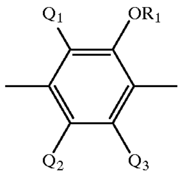 | 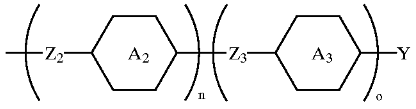 |
| 363 | 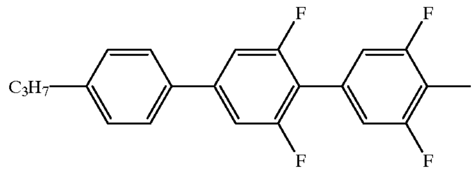 | 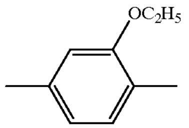 | $—OCF_3$ |
| 364 | 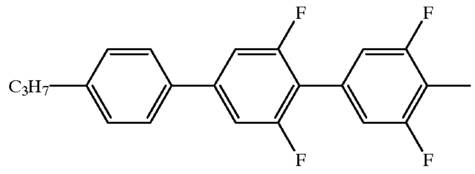 | 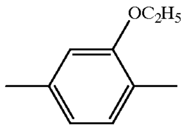 | —CN |
| 365 | 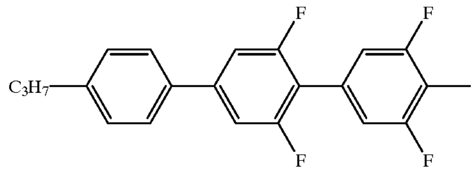 | 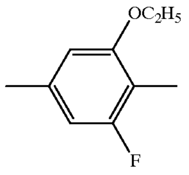 | —F |
| 366 | 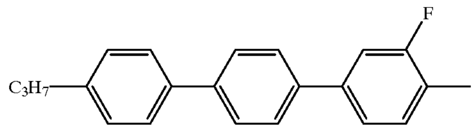 | 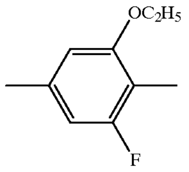 | $—CF_3$ |

-continued
| No. | | | |
|---|---|---|---|
| | 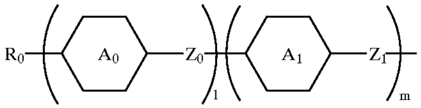 | 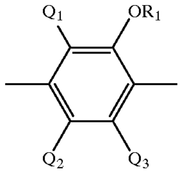 | 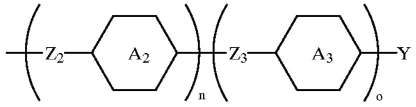 |
| 367 | 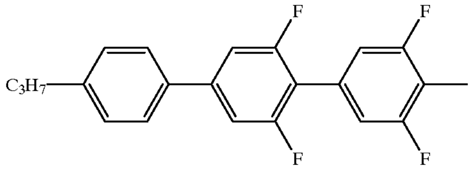 | 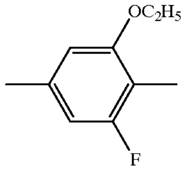 | $—OCF_3$ |
| 368 | 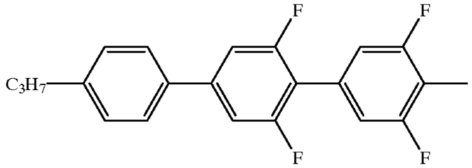 | 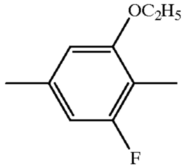 | —CN |
| 369 | 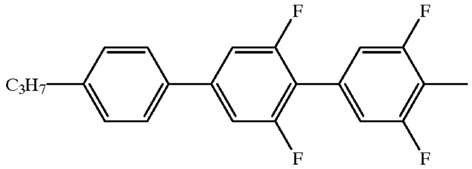 | 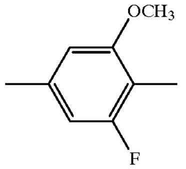 | $—C_5H_{11}$ |
| 370 | 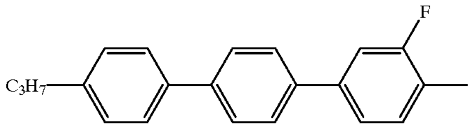 | 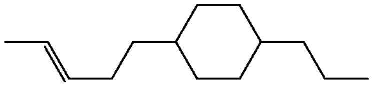 | —F |
| 371 | 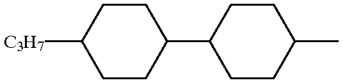 | 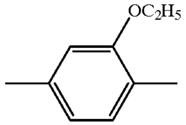 | 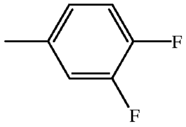 |

-continued
| No. | | | |
|---|---|---|---|
| | 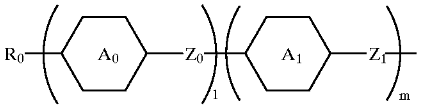 | 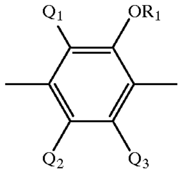 | 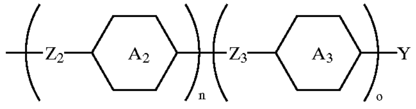 |
| 372 | 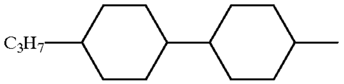 | 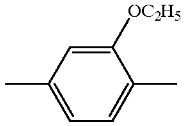 | 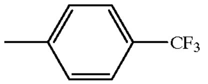 |
| 373 | 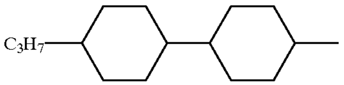 | 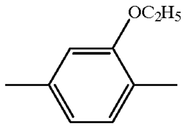 | 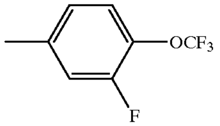 |
| 374 | 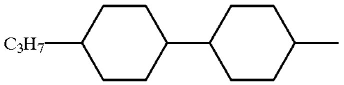 | 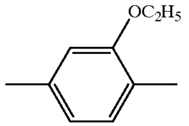 | 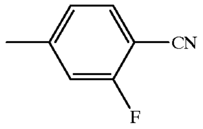 |
| 375 | 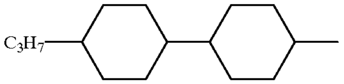 | 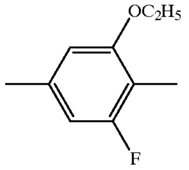 | 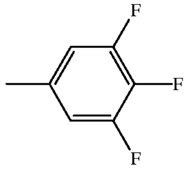 |
| 376 | 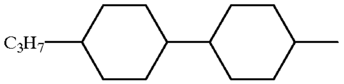 | 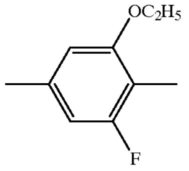 | 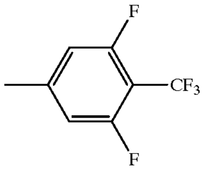 |

-continued
| No. | 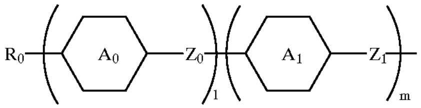 | 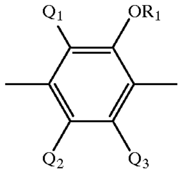 | 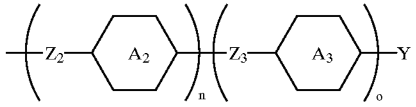 |
|---|---|---|---|
| 377 | 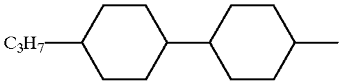 | 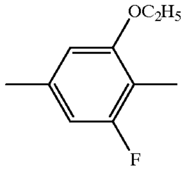 | 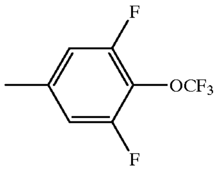 |
| 378 | 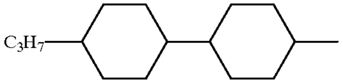 | 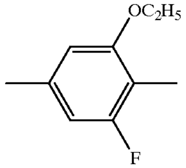 | 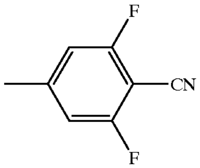 |
| 379 | 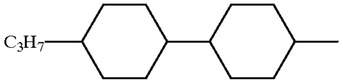 | 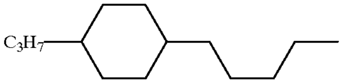 | 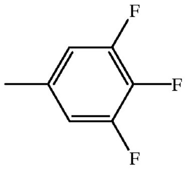 |
| 380 | 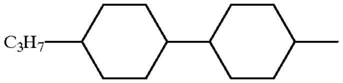 | 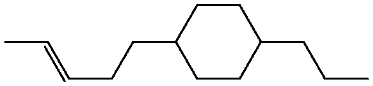 | 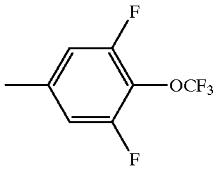 |

-continued
| No. | 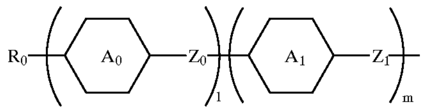 | 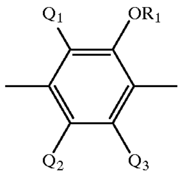 | 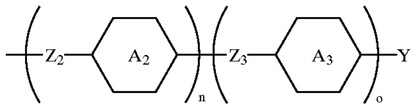 |
|---|---|---|---|
| 381 | 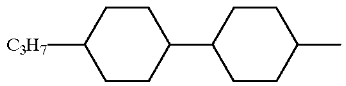 | 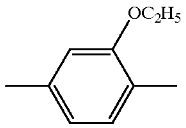 | 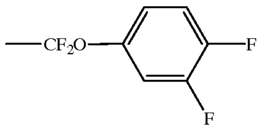 |
| 382 | 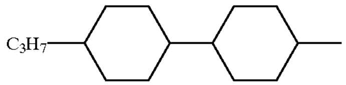 | 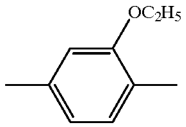 | 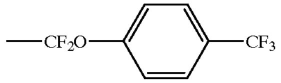 |
| 383 | 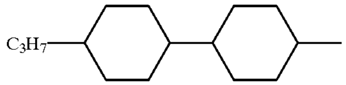 | 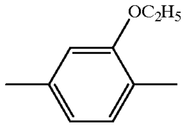 | 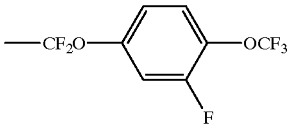 |
| 384 | 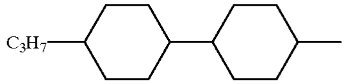 | 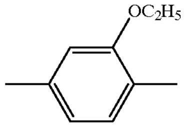 | 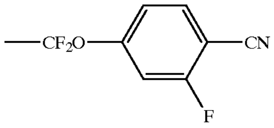 |
| 385 | 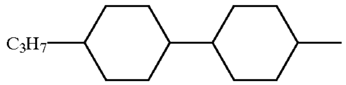 | 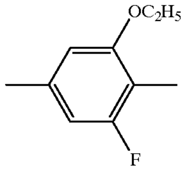 | 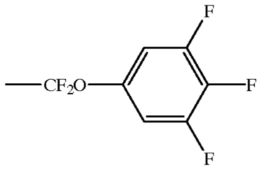 |

-continued
| No. | 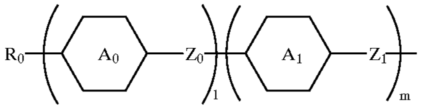 | 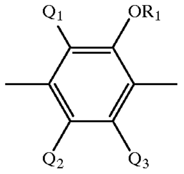 | 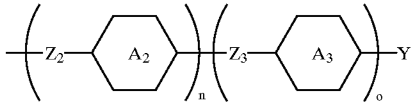 |
|---|---|---|---|
| 386 | 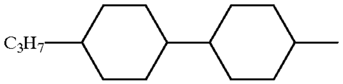 | 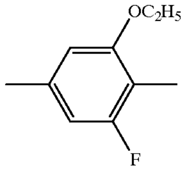 | 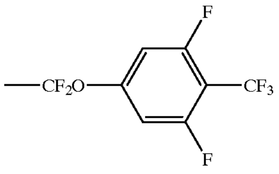 |
| 387 | 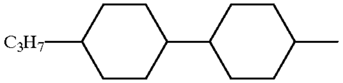 | 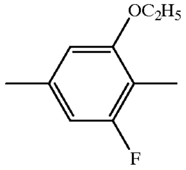 | 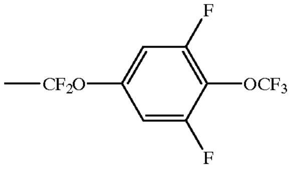 |
| 388 | 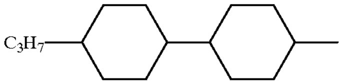 | 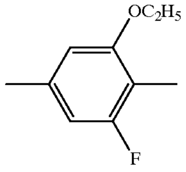 | 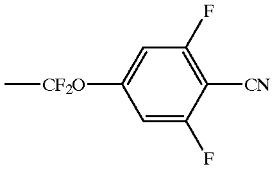 |
| 389 | 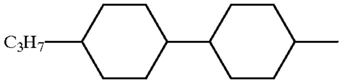 | 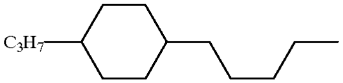 | 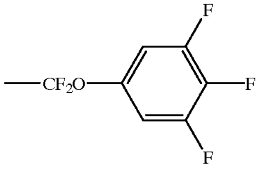 |

-continued
| No. | | | |
|---|---|---|---|
| | 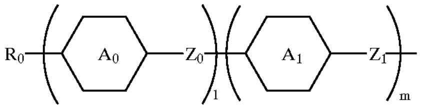 | 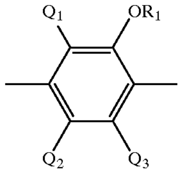 | 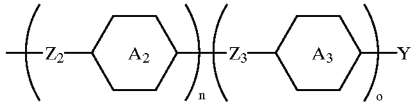 |
| 390 | 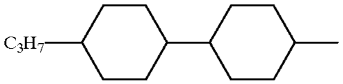 | 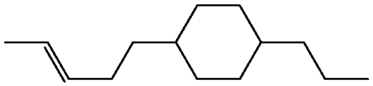 | 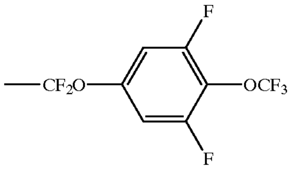 |
| 391 | 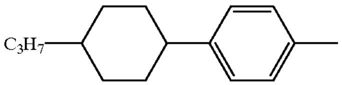 | 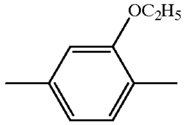 | 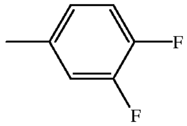 |
| 392 | 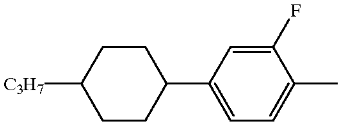 | 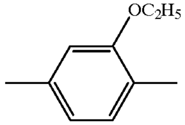 | 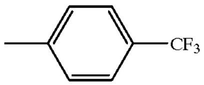 |
| 393 | 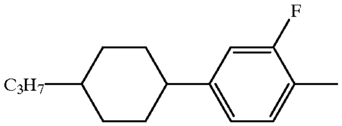 | 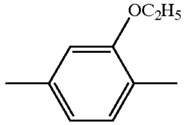 | 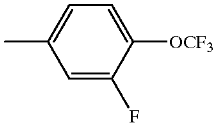 |
| 394 | 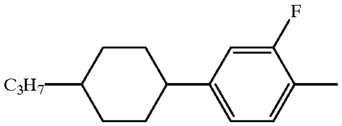 | 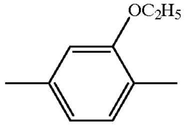 | 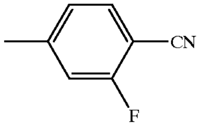 |

-continued
| No. | 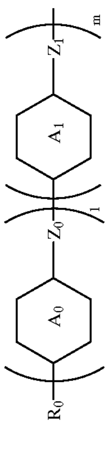 | 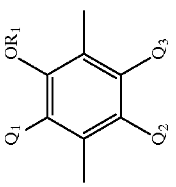 | 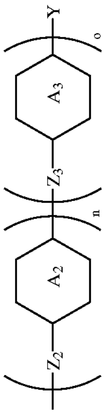 |
|---|---|---|---|
| 395 | 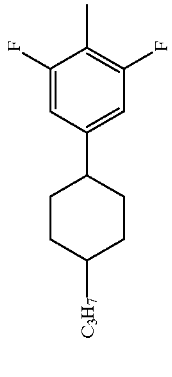 | 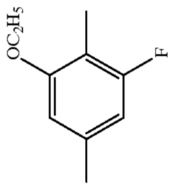 | 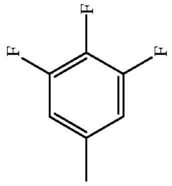 |
| 396 | 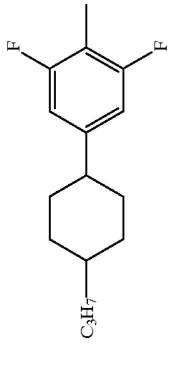 | 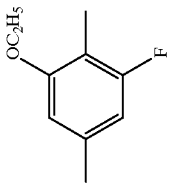 | 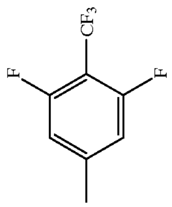 |
| 397 | 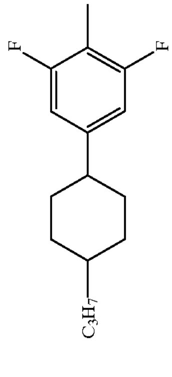 | 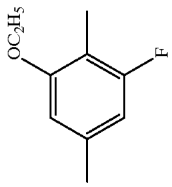 | 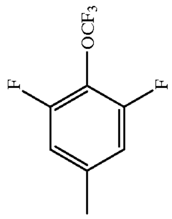 |
| 398 | 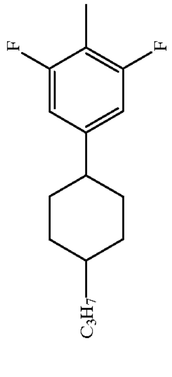 | 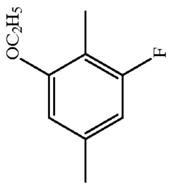 | 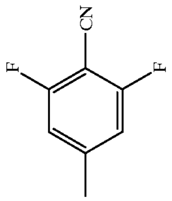 |

-continued
| No. | 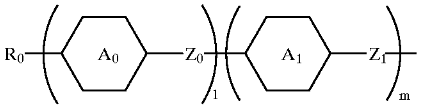 | 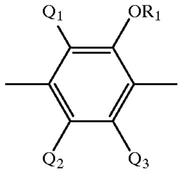 | 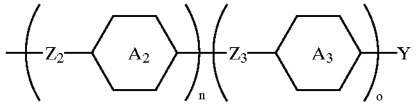 |
|---|---|---|---|
| 399 | 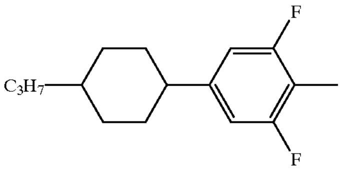 | 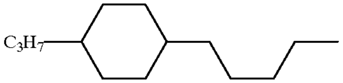 | 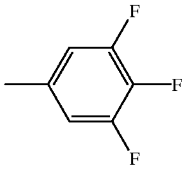 |
| 400 | 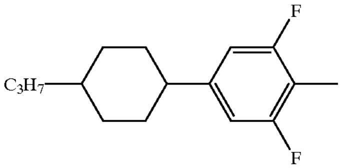 | 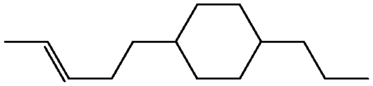 | 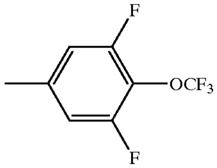 |
| 401 | 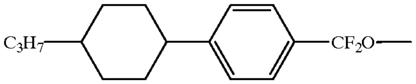 | 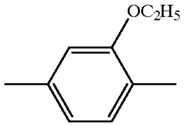 | 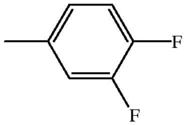 |
| 402 | 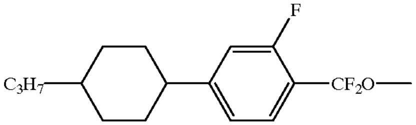 | 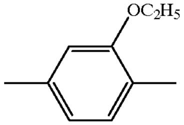 | 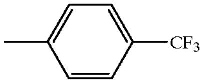 |
| 403 | 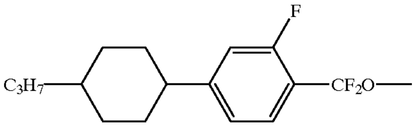 | 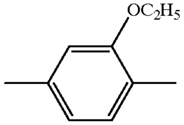 | 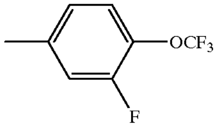 |

-continued
| No. | 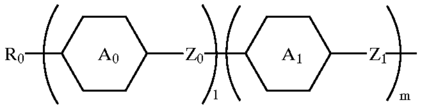 | 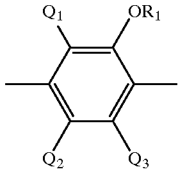 | 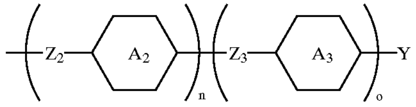 |
|---|---|---|---|
| 404 | 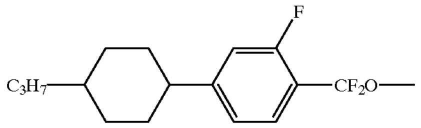 | 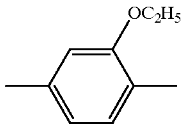 | 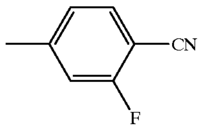 |
| 405 | 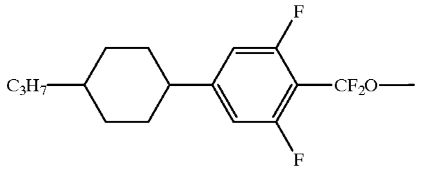 | 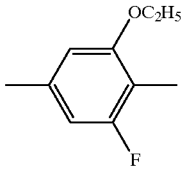 | 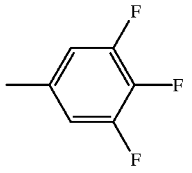 |
| 406 | 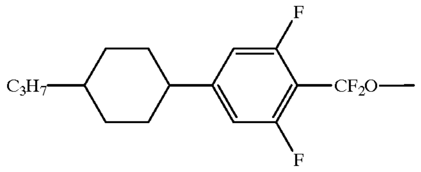 | 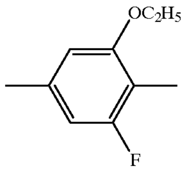 | 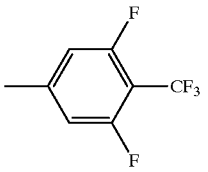 |
| 407 | 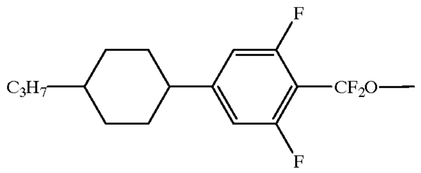 | 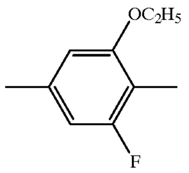 | 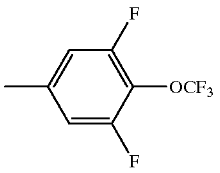 |

-continued
| No. | | | |
|---|---|---|---|
| | 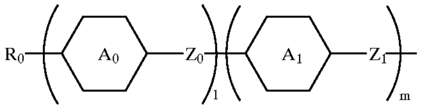 | 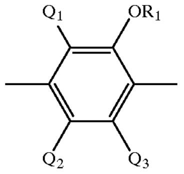 | 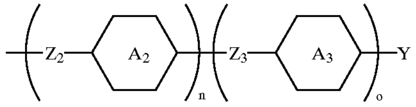 |
| 408 | 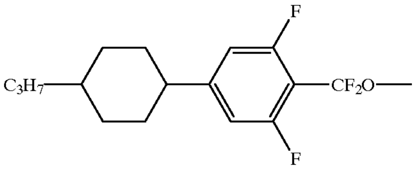 | 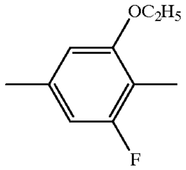 | 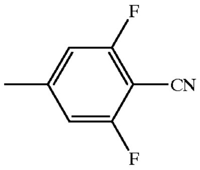 |
| 409 | 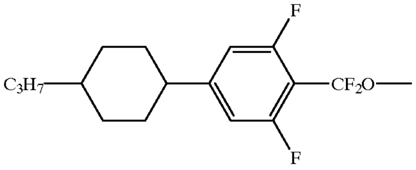 | 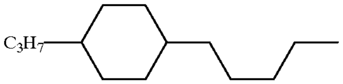 | 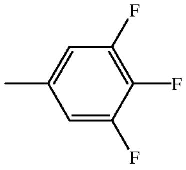 |
| 410 | 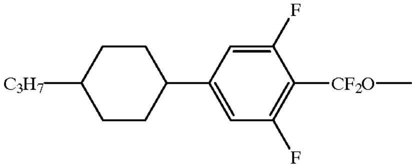 | 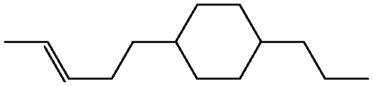 | 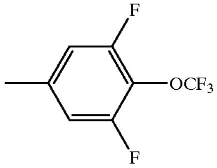 |
| 411 | 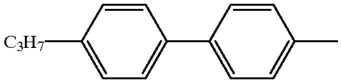 | 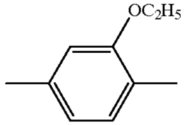 | 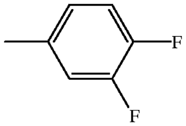 |
| 412 | 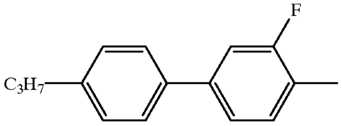 | 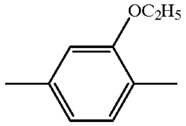 | 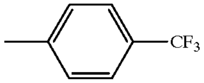 |

-continued
| No. | 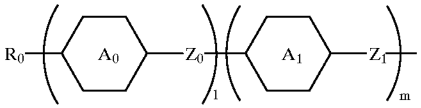 | 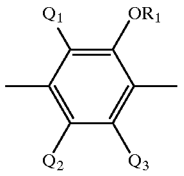 | 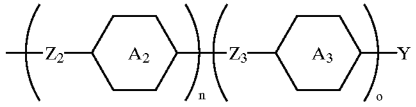 |
|---|---|---|---|
| 413 | 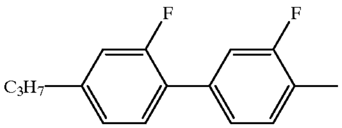 | 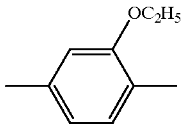 | 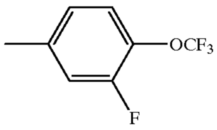 |
| 414 | 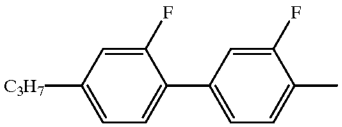 | 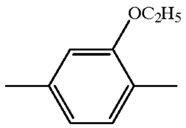 | 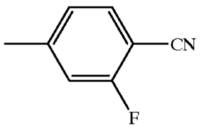 |
| 415 | 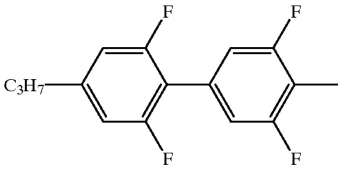 | 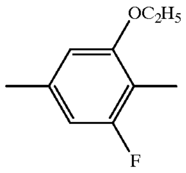 | 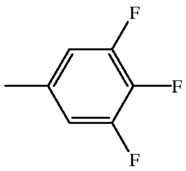 |
| 416 | 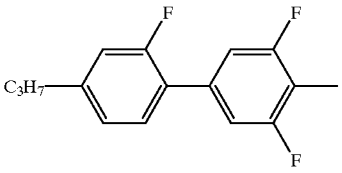 | 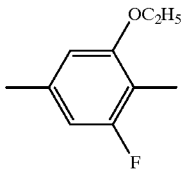 | 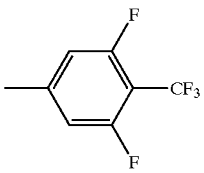 |
| 417 | 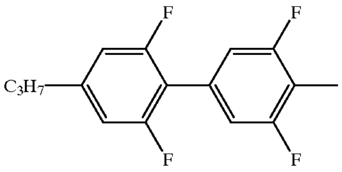 | 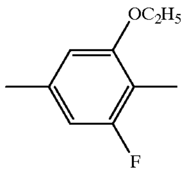 | 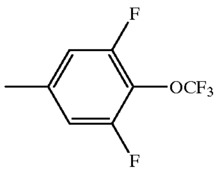 |

-continued
| No. | 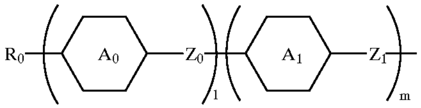 | 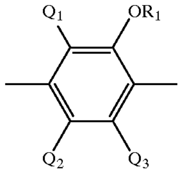 | 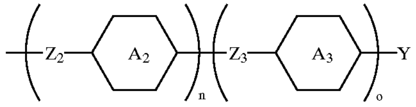 |
|---|---|---|---|
| 418 | 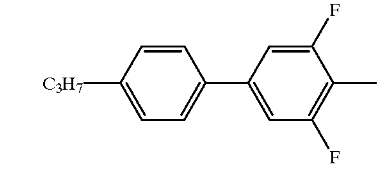 | 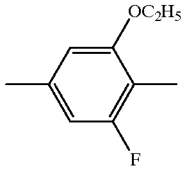 | 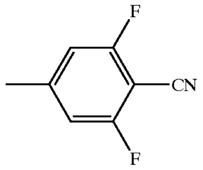 |
| 419 | 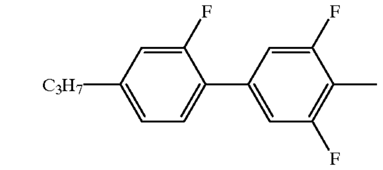 | 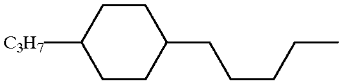 | 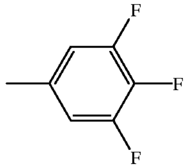 |
| 420 | 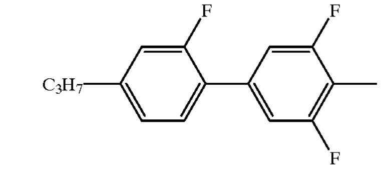 | 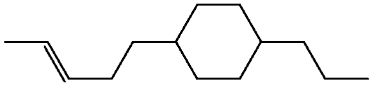 | 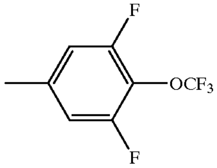 |
| 421 | 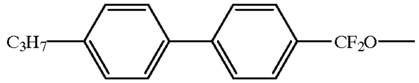 | 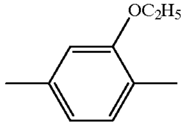 | 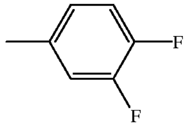 |
| 422 | 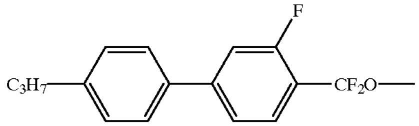 | 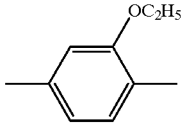 | 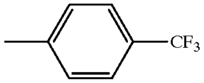 |

-continued
| No. | 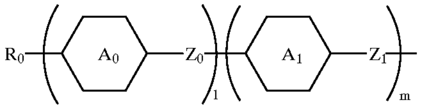 | 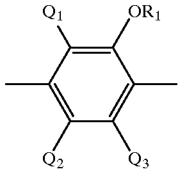 | 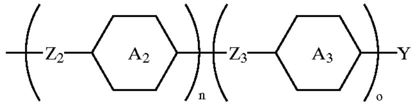 |
|---|---|---|---|
| 423 | 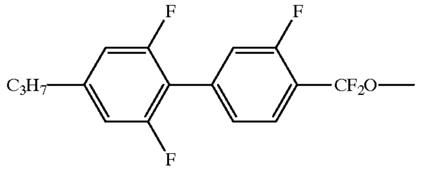 | 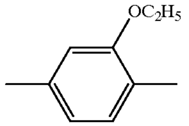 | 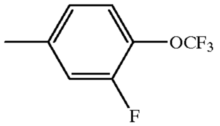 |
| 424 | 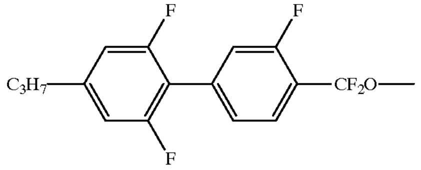 | 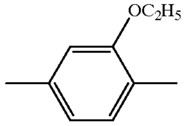 | 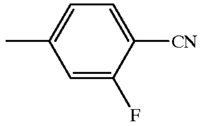 |
| 425 | 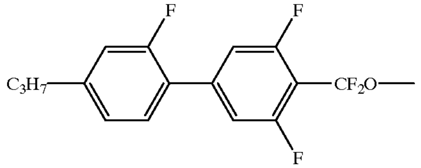 | 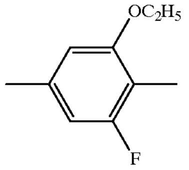 | 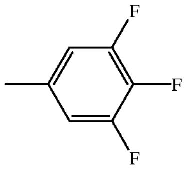 |
| 426 | 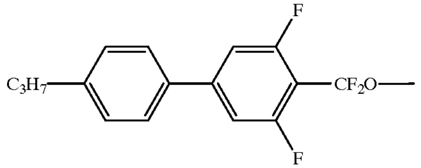 | 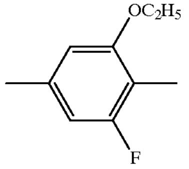 | 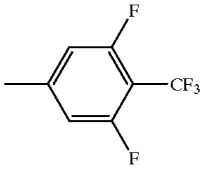 |

-continued
| No. | | | |
|---|---|---|---|
| | 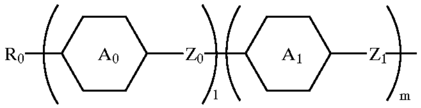 | 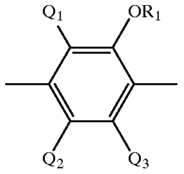 | 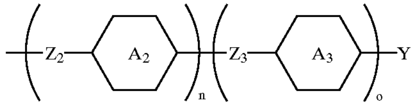 |
| 427 | 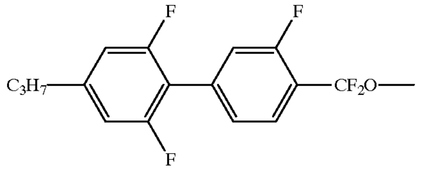 | 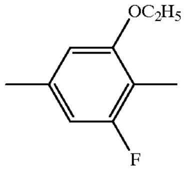 | 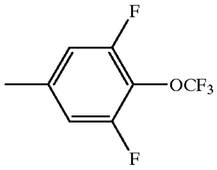 |
| 428 | 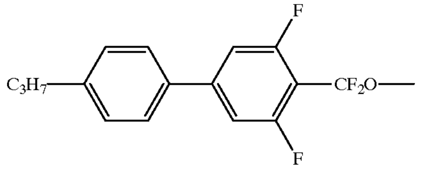 | 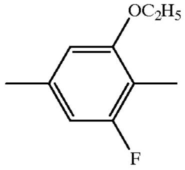 | 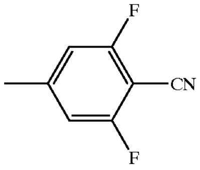 |
| 429 | 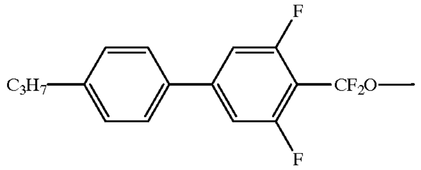 | 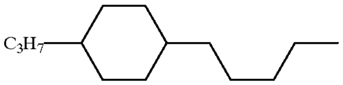 | 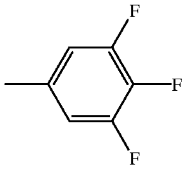 |
| 430 | 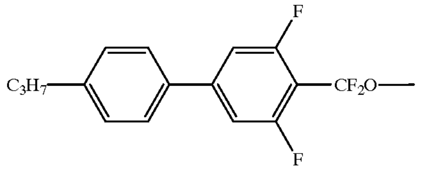 | 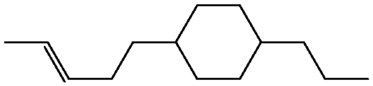 | 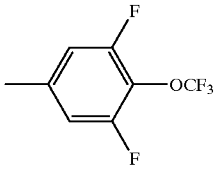 |

EXAMPLE 5

Use Example 1

Liquid crystal composition comprising

| | |
|---|---|
| 4-(trans-4-propylcyclohexyl)benzonitrile | 24% by weight |
| 4-(trans-4-pentylcyclohexyl)benzonitrile | 36% by weight |
| 4-(trans-4-heptylcyclohexyl)benzonitrile | 25% by weight |
| 4-(4-propylphenyl)benzonitrile | 15% by weight |

(hereinafter the liquid crystal composition is abbreviated as Mother liquid crystal A) was a nematic liquid crystal and had a clearing point (Cp) of 72.4° C. Threshold voltage determined by filling Mother liquid crystal A in a twisted nematic cell having a cell thickness of 9 μm was 1.78 V, and dielectric anisotropy (Δ∈) was +11.0, optical anisotropy (Δn) was 0.137, and viscosity at 20° C. ($\eta_{20}$) was 27.0 mPa·s.

Mother liquid crystal A in an amount of 85 parts by weight and 15 parts by weight of the 3,4-difluoro-5-ethoxy-(trans-4-(trans-4-propylcyclohexyl)cyclohexyl)benzene (Compound No. 195) prepared in Example 1 were mixed and its physical properties were determined. The results were Cp: 60.1° C., Vth: 1.42 V (9.3 μm), Δ∈: 11.7, Δn: 0.120, and $\eta_{20}$: 30.4 mPa·s. While this liquid crystal composition was left in a freezer at −20° C. for 40 days, separation of crystals or development of smectic phase was not noticed.

EXAMPLE 6

Use Example 2

Mother liquid crystal A in an amount of 85 parts by weight and 15 parts by weight of the 4-fluoro-3,5-dimethoxy-(trans-4-(trans-4-propylcyclohexyl)cyclohexyl)benzene (Compound No. 199) prepared in Example 2 were mixed and its physical properties were determined. The results were Cp: 55.3° C., Vth: 1.31 V (9.0 μm), Δ∈: 11.1, Δn: 0.115, and $\eta_{20}$: 39.7 mPa·s. While this liquid crystal composition was left in a freezer at −20° C. for 40 days, separation of crystals or development of smectic phase was not noticed.

EXAMPLE 7

Use Example 3

Mother liquid crystal A in an amount of 85 parts by weight and 15 parts by weight of the 4-propyl-α,α-difluorobenzyl-(3-fluoro-4-trifluoromethyl-5-ethoxyphenyl)ether (Compound No. 30) prepared in Example 3 were mixed and its physical properties were determined. The results were Cp: ° C., Vth: ,V (9.0 μm), Δ∈: , Δn: , and $\eta_{20}$: mPa·s. While this liquid crystal composition was left in a freezer at −20° C. for 40 days, separation of crystals or development of smectic phase was not noticed.

COMPARATIVE EXAMPLE 1

In order to compare with the compounds of the present invention, compounds (12-1-1) and (12-2-1) in both of which alkyl group (R) is n-propyl group in compound (12-1) and (12-2), respectively, shown in the section of BACKGROUND ART were prepared according to the method described in Laid-open Japanese Patent Publication No. Hei 2-233626.

(12-1-1)

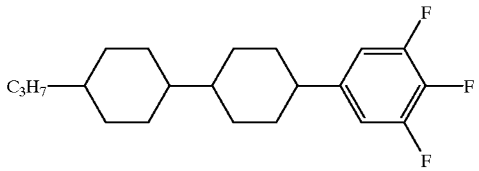

Cr 64.7 N 93.7 Iso (12-2-1)

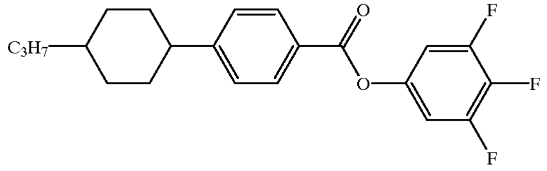

Cr 98.3(N 90.1) Iso

Liquid crystal composition comprising 1,2-difluoro-4-(trans-4-(trans-4-ethylcyclohexyl)cyclohexyl)benzene 33.3% by weight 1,2-difluoro-4-(trans-4-(trans-4-propylcyclohexyl)cyclohexyl)benzene 33.3% by weight 1,2-difluoro-4-(trans-4-(trans-4-pentylcyclohexyl)cyclohexyl)benzene 33.3% by weight (hereinafter the liquid crystal composition is abbreviated as Mother liquid crystal B) was prepared. Mother liquid crystal B in an amount of 80% by weight was mixed with 20% by weight of each of the comparative compounds (12-1-1) and (12-2-1), and a compound of the present invention (Compound No. 195) shown in Example 1 to prepare liquid crystal compositions B-1, B-2, and B-3, respectively, and their dielectric anisotropy and voltage holding ratio at 100° C. were determined. The results are shown in Table 2.

TABLE 2

| | Composition and compound | $\Delta\epsilon$*2 | V.H.R (%)*1 |
|---|---|---|---|
| Mother liquid crystal B | Compound | — | 97.1 |
| Composition B-1 | 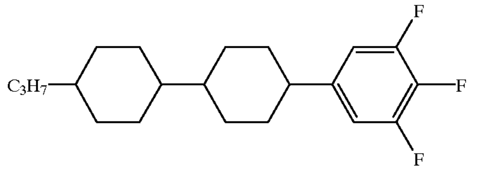 (12-1-1) | 8.3 | 96.9 |
| Composition B-2 | 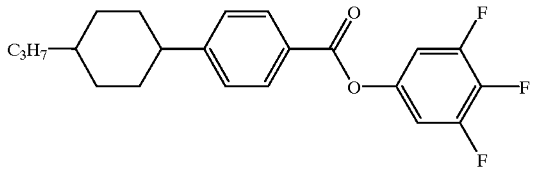 (12-2-1) | 11.4 | 95.0 |
| Composition B-3 | 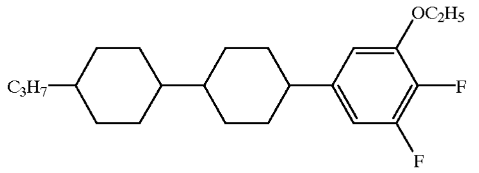 (No. 195) | 9.4 | 96.8 |

*1Determined value of liquid crystal composition at 100° C.
*2Determined value of compound (Value of dielectric anisotropy of each compound was obtained by extrapolation based on the value of Mother liquid crystal B.)

As will be seen from Table 2, compound of the present invention (Compound No. 195) and comparative compound (12-2-1) exhibit a high dielectric anisotropy compared with comparative compound (12-1-1) and thus are excellent as liquid crystal material for low voltage. However, when their voltage holding ratios are compared, it can be understood that composition B-2 comprising comparative compound (12-2-1) exhibits lower voltage holding ratio than composition B-3 comprising the compound of the present invention and composition B-1 comprising comparative compound (12-1-1) by about 2%, and thus can not be used for liquid crystal display devices intended for high reliability. On the other hand, like composition B-1, composition B-3 comprising the compound of the present invention exhibited as considerably high value as 96.8% even at 100° C. Accordingly, the compound of the present invention is remarkably excellent in the applications wherein possibility of being driven at a low voltage and a high reliability are required.

COMPARATIVE EXAMPLE 2

Liquid crystal compositions B-1 and B-3 prepared in Comparative Example 1 described above were filled in a parallel cell having a polyimide alignment film and having a cell thickness of 20 μm, respectively, and the pretilt angle was determined by crystal rotation method. As the result, it was found that whereas the pretilt angle of the composition B-1 comprising the comparative compound (12-1-1) was 5.4°, that of the composition B-3 comprising the compound (Compound No. 195) of the present invention was as large as 5.9°.

INDUSTRIAL APPLICABILITY

Compounds of the present invention are excellent in miscibility with other liquid crystal compositions, particularly in the miscibility at low temperatures. Also, as demonstrated in Examples and Comparative Examples, liquid crystal compositions comprising the compound of the present invention have characteristics such as 1) their threshold voltage is low, 2) they induce a large pretilt angle, and 3) their voltage holding ratio is high and its dependency on temperature is small.

Accordingly, the compositions of the present invention make driving of liquid crystal display devices at a low voltage possible and can impart a high reliability to liquid crystal display devices at the same time.

What is claimed is:

1. A liquid crystalline compound expressed by the general formula (1)

(1)

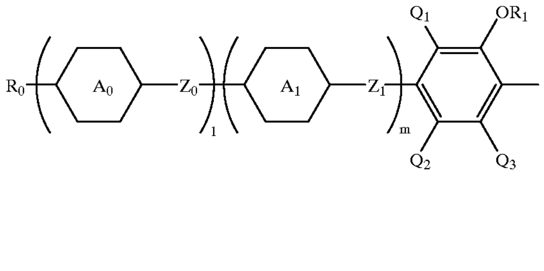

-continued

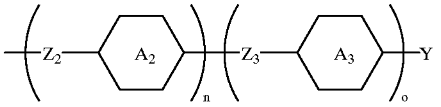

wherein $R_0$ represents an alkyl group having 1 to 10 carbon atoms in which alkyl group one or more not-adjacent methylene groups may be replaced by oxygen atom, sulfur atom, —$SiH_2$—, —CH═CH—, or —C≡C—, and any hydrogen atom in the alkyl group may be replaced by a halogen atom;

$R_1$ represents an alkyl group having 1 to 10 carbon atoms;

ring $A_0$, ring $A_1$, ring $A_2$, and ring $A_3$ independently represent 1,4-cyclohexylene group, 1,3-dioxane-2,5-diyl group, 1,4-phenylene group in which one or more hydrogen atoms on the ring may be replaced by a halogen atom, pyridine-2,5-diyl group, or pyrimidine-2,5-diyl group;

$Z_0$, $Z_1$, $Z_2$, and $Z_3$ independently represent —$CH_2CH_2$—, —CH═CH—, —C≡C—, —$CH_2O$—, —$OCH_2$—, —$CF_2O$—, —$OCF_2$—, —COO—, —OCO—, —$(CH_2)_4$—, or single bond;

$Q_1$ and $Q_2$ independently represent hydrogen atom or a halogen atom;

$Q_3$ represents hydrogen atom, a halogen atom, or $R_2O$ group;

$R_2$ represents an alkyl group having 1 to 10 carbon atoms;

Y represents a halogen atom, cyano group, or an alkyl group having 1 to 10 carbon atoms in which alkyl group one or more not-adjacent methylene groups may be replaced by oxygen atom, sulfur atom, —$SiH_2$—, —CH═CH—, or —C≡C—, and any hydrogen atom in the alkyl group may be replaced by a halogen atom;

l, m, n and o are independently 0, 1, or 2 with the proviso that $1 \leqq l+m+n+o \leqq 3$;

provided that when one of $Z_0$, $Z_1$, $Z_2$, and $Z_3$ is —COO—, then Y is not cyano group, and that when n=o=0, $Z_0$ and $Z_1$ are a group selected from —$CH_2CH_2$—, —$CH_2O$—, —$OCH_2$—, —$(CH_2)_4$—, —C≡C—, and single bond, $Q_3$ is fluorine atom, and Y is fluorine atom or chlorine atom, then $R_2$ is $C_2H_5$ group; and the atom which constitutes this compound may be replaced by its isotope.

2. The liquid crystalline compound according to claim 1 wherein l=1, and m=n=o=0 in the general formula (1).

3. The liquid crystalline compound according to claim 1 wherein l=m=1, and n=o=0 in the general formula (1).

4. The liquid crystalline compound according to claim 1 wherein l=n=1, and m=o=0 in the general formula (1).

5. The liquid crystalline compound according to claim 1 wherein l=2, m=1, and n=o=0 in the general formula (1).

6. The liquid crystalline compound according to claim 1 wherein l=1, m=2, and n=o=0 in the general formula (1).

7. The liquid crystalline compound according to claim 1 wherein l=m=n=1, and o=0 in the general formula (1).

8. The liquid crystalline compound according to claim 2 wherein $Q_3$ is $R_2O$ group in the general formula (1).

9. The liquid crystalline compound according to claim 3 wherein $Q_3$ is $R_2O$ group in the general formula (1).

10. The liquid crystalline compound according to claim 4 wherein $Q_3$ is $R_2O$ group in the general formula (1).

11. The liquid crystalline compound according to claim 5 wherein $Q_3$ is $R_2O$ group in the general formula (1).

12. The liquid crystalline compound according to claim 6 wherein $Q_3$ is $R_2O$ group in the general formula (1).

13. The liquid crystalline compound according to claim 7 wherein $Q_3$ is $R_2O$ group in the general formula (1).

14. The liquid crystalline compound according to claim 1 wherein any one of $Z_0$, $Z_1$, $Z_2$, and $Z_3$ is —$CF_2O$— group in the general formula (1).

15. The liquid crystalline compound according to claim 1 wherein at least one of ring $A_0$, ring $A_1$, ring $A_2$, and ring $A_3$ is 1,4-phenylene group which may be replaced by $R_2O$ group in the general formula (1).

16. A liquid crystal composition comprising at least two components; and comprising, as a first component, at least one compound expressed by the general formula (1)

(1)

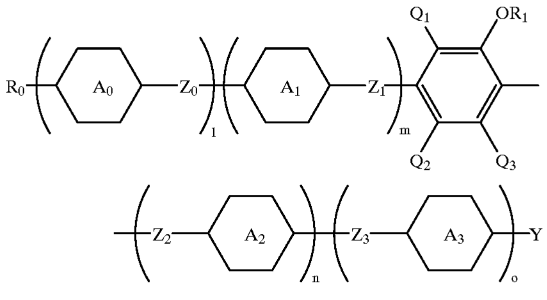

wherein $R_0$ represents an alkyl group having 1 to 10 carbon atoms in which alkyl group one or more not-adjacent methylene groups may be replaced by oxygen atom, sulfur atom, —$SiH_2$—, —CH═CH—, or —C≡C—, and any hydrogen atom in the alkyl group may be replaced by a halogen atom;

$R_1$ represents an alkyl group having 1 to 10 carbon atoms;

ring $A_0$, ring $A_1$, ring $A_2$, and ring $A_3$ independently represent 1,4-cyclohexylene group, 1,3-dioxane-2,5-diyl group, 1,4-phenylene group in which one or more hydrogen atoms on the ring may be replaced by a halogen atom, pyridine-2,5-diyl group, or pyrimidine-2,5-diyl group;

$Z_0$, $Z_1$, $Z_2$, and $Z_3$ independently represent —$CH_2CH_2$—, —CH═CH—, —C≡C—, —$CH_2O$—, —$OCH_2$—, —$CF_2O$—, —$OCF_2$—, —COO—, —OCO—, —$(CH_2)_4$—, or single bond;

$Q_1$ and $Q_2$ independently represent hydrogen atom or a halogen atom;

$Q_3$ represents hydrogen atom, a halogen atom, or $R_2O$ group;

$R_2$ represents an alkyl group having 1 to 10 carbon atoms;

Y represents a halogen atom, cyano group, or an alkyl group having 1 to 10 carbon atoms in which alkyl group one or more not-adjacent methylene groups may be replaced by oxygen atom, sulfur atom, —$SiH_2$—, —CH═CH—, or —C≡C—, and any hydrogen atom in the alkyl group may be replaced by a halogen atom;

l, m, n and o are independently 0, 1, or 2 with the proviso that $1 \leqq l+m+n+o \leqq 3$;

provided that when one of $Z_0$, $Z_1$, $Z_2$, and $Z_3$ is —COO—, then Y is not cyano group, and that when n=o=0, $Z_0$ and $Z_1$ are a group selected from —$CH_2CH_2$—, —$CH_2O$—, —$OCH_2$—, —$(CH_2)_4$—, —C≡C—, and single bond, $Q_3$ is fluorine atom, and Y is fluorine atom or chlorine atom, then $R_2$ is $C_2H_5$ group; and the atom which constitutes this compound may be replaced by its isotope, and optionally, as a second component, at least one optically active compound.

17. A liquid crystal composition comprising, as a first component, at least one compound defined in any one of claims 1 to 15, comprising, as a second component, at least one compound selected from the group consisting of the compounds expressed by any one of the general formulas (2), (3), and (4)

(2)

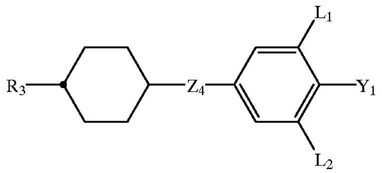

(3)

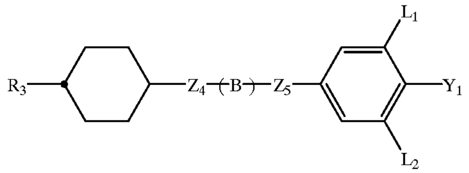

(4)

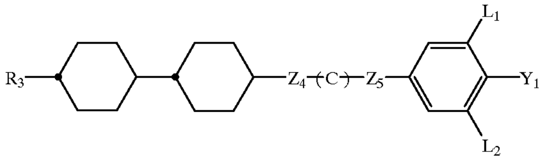

wherein $R_3$ represents an alkyl group having 1 to 10 carbon atoms in which alkyl group one or more not-adjacent methylene groups may be replaced by oxygen atom or —CH=CH—, and any hydrogen atom in the alkyl group may be replaced by fluorine atom;

$Y_1$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$;

$L_1$ and $L_2$ independently represent hydrogen atom or fluorine atom;

$Z_4$ and $Z_5$ independently represent 1,2-ethylene group, 1,4-butylene group, —COO—, $—CF_2O—$, $—OCF_2—$, —CH=CH—, or single bond;

ring B represents trans-1,4-cyclohexylene, 1,3-dioxane-2,5-diyl, or 1,4-phenylene in which hydrogen atom may be replaced by fluorine atom;

ring C represents 1,4-cyclohexylene, or 1,4-phenylene in which hydrogen atom may be replaced by fluorine atom; and the atom which constitutes this compound may be replaced by its isotope, and optionally comprising, as a third component, at least one optically active compound.

18. A liquid crystal composition comprising, as a first component, at least one compound defined in any one of claims 1 to 15, comprising, as a second component, at least one compound selected from the group consisting of the compounds expressed by the general formula (5) or (6)

(5)

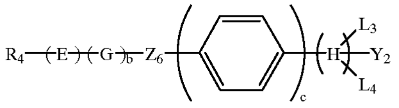

(6)

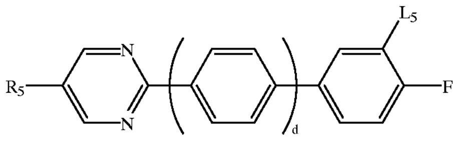

wherein $R_4$ and $R_5$ independently represent an alkyl group having 1 to 10 carbon atoms in which alkyl group one or more not-adjacent methylene groups may be replaced by oxygen atom or —CH=CH—, and any hydrogen atom in the alkyl group may be replaced by fluorine atom;

$Y_2$ represents cyano group or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene, 1,4-phenylene in which hydrogen atom may be replaced by fluorine atom, or pyrimidine-2,5-diyl;

ring H represents trans-1,4-cyclohexylene or 1,4-phenylene;

$Z_6$ represents $—CH_2CH_2—$, —COO—, or single bond;

$L_3$, $L_4$, and $L_5$ independently represent hydrogen atom or fluorine atom;

b, c, and d are independently 0 or 1; and the atom which constitutes this compound may be replaced by its isotope, and optionally comprising, as a third component, at least one optically active compound.

19. A liquid crystal composition comprising, as a first component, at least one compound defined in any one of claims 1 to 15, comprising, as a second component, at least one compound selected from the group consisting of the compounds expressed by any one of the general formulas (2), (3), and (4)

(2)

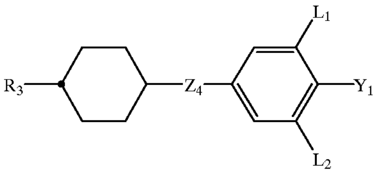

(3)

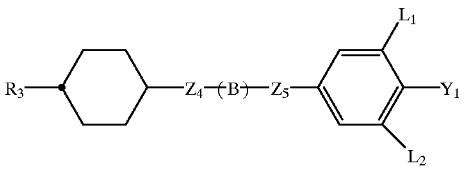

-continued (4)

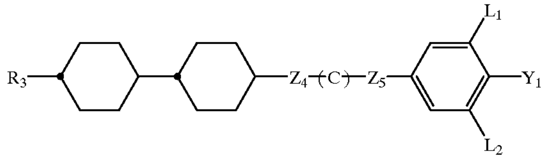

wherein $R_3$ represents an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

$Y_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$;

$L_1$ and $L_2$ independently represent hydrogen atom or fluorine atom;

$Z_4$ and $Z_5$ independently represent 1,2-ethylene group, 1,4-butylene group, —COO—, —$CF_2O$, —$OCF_2$—, —CH═CH—, or single bond;

ring B represents trans-1,4-cyclohexylene, 1,3-dioxane-2,5-diyl, or 1,4-phenylene in which hydrogen atom may be replaced by fluorine atom;

ring C represents 1,4-cyclohexylene, or 1,4-phenylene in which hydrogen atom may be replaced by fluorine atom; and the atom which constitutes this compound may be replaced by its isotope, comprising, as a third component, at least one compound selected from the group consisting of the compounds expressed by any one of the general formulas (7), (8), and (9)

(7)

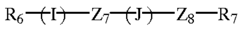

(8)

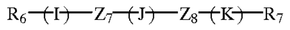

(9)

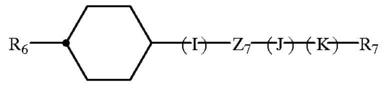

wherein $R_6$ and $R_7$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

ring I, ring J, and ring K independently represent trans-1,4-cyclohexylene, pyrimidine-2,5-diyl, or 1,4-phenylene in which hydrogen atom may be replaced by fluorine atom;

$Z_7$ and $Z_8$ independently represent —C≡C—, —COO—, —$CH_2CH_2$—, —CH═CH—, or single bond; and the atom which constitutes this compound may be replaced by its isotope, and optionally comprising, as a fourth component, at least one optically active compound.

20. A liquid crystal composition comprising, as a first component, at least one compound defined in any one of claims 1 to 15, comprising, as a second component, at least one compound selected from the group consisting of the compounds expressed by the general formula (5) or (6)

(5)

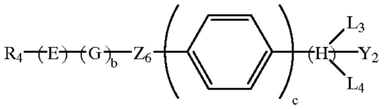

(6)

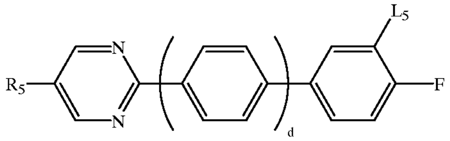

wherein $R_4$ and $R_5$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

$Y_2$ represents cyano group or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene, 1,4-phenylene in which hydrogen atom may be replaced by fluorine atom, or pyrimidine-2,5-diyl;

ring H represents trans-1,4-cyclohexylene or 1,4-phenylene;

$Z_6$ represents —$CH_2CH_2$—, —COO—, or single bond;

$L_3$, $L_4$, and $L_5$ independently represent hydrogen atom or fluorine atom;

b, c, and d are independently 0 or 1; and the atom which constitutes this compound may be replaced by its isotope, comprising, as a third component, at least one compound selected from the group consisting of the compounds expressed by any one of the general formulas (7), (8), and (9)

(7)

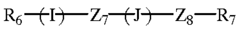

(8)

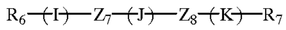

(9)

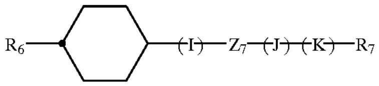

wherein $R_6$ and $R_7$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

ring I, ring J, and ring K independently represent trans-1,4-cyclohexylene, pyrimidine-2,5-diyl, or 1,4-phenylene in which hydrogen atom may be replaced by fluorine atom;

$Z_7$ and $Z_8$ independently represent —C≡C—, —COO—, —$CH_2CH_2$—, —CH═CH—, or single bond; and the atom which constitutes this compound may be replaced by its isotope, and optionally comprising, as a fourth component, at least one optically active compound.

21. A liquid crystal composition comprising, as a first component, at least one compound defined in any one of claims 1 to 15, comprising, as a second component, at least one compound selected from the group consisting of the compounds expressed by any one of the general formulas (2), (3), and (4)

(2)

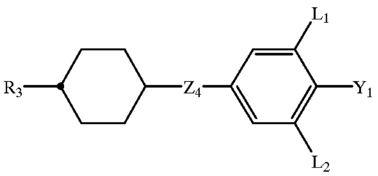

(3)

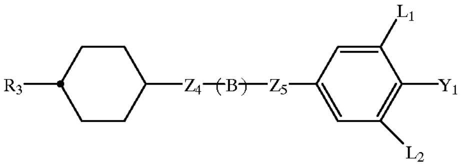

(4)

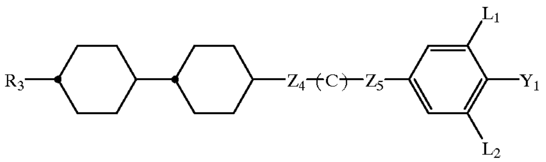

wherein $R_3$ represents an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

$Y_1$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$;

$L_1$ and $L_2$ independently represent hydrogen atom or fluorine atom;

$Z_4$ and $Z_5$ independently represent 1,2-ethylene group, 1,4-butylene group, —COO—, $—CF_2O—$, $—OCF_2—$, —CH═CH—, or single bond;

ring B represents trans-1,4-cyclohexylene, 1,3-dioxane-2,5-diyl, or 1,4-phenylene in which hydrogen atom may be replaced by fluorine atom;

ring C represents 1,4-cyclohexylene, or 1,4-phenylene in which hydrogen atom may be replaced by fluorine atom; and the atom which constitutes this compound may be replaced by its isotope, comprising, as a third component, at least one compound selected from the group consisting of the compounds expressed by the genera formula (5) or (6)

(5)

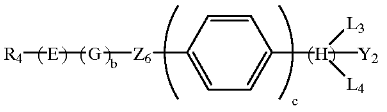

(6)

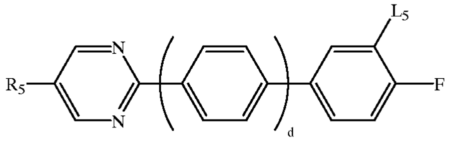

wherein $R_4$ and $R_5$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

$Y_2$ represents cyano group or —C═C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene, 1,4-phenylene in which hydrogen atom may be replaced by fluorine atom, or pyrimidine-2,5-diyl;

ring H represents trans-1,4-cyclohexylene or 1,4-phenylene;

$Z_6$ represents $—CH_2CH_2—$, —COO—, or single bond;

$L_3$, $L_4$, and $L_5$ independently represent hydrogen atom or fluorine atom;

b, c, and d are independently 0 or 1; and the atom which constitutes this compound may be replaced by its isotope, comprising, as a fourth component, at least one compound selected from the group consisting of the compounds expressed by any one of the general formulas (7), (8), and (9)

(7)

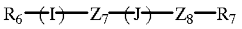

(8)

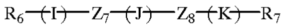

(9)

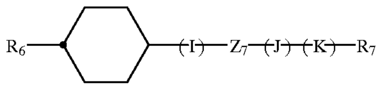

wherein $R_6$ and $R_7$ independently represent an alkyl group having 1 to 10 carbon atoms in which alkyl group one or more not-adjacent methylene groups may be replaced by oxygen atom or —CH═CH—, and any hydrogen atom in the alkyl group may be replaced by fluorine atom;

ring I, ring J, and ring K independently represent trans-1,4-cyclohexylene, pyrimidine-2,5-diyl, or 1,4-phenylene in which hydrogen atom may be replaced by fluorine atom;

$Z_7$ and $Z_8$ independently represent —C≡C—, —COO—, $—CH_2CH_2—$, —CH═CH—, or single bond; and the atom which constitutes this compound may be replaced by its isotope, and optionally comprising, as a fifth component, at least one optically active compound.

22. A liquid crystal display device comprising a liquid crystal composition defined in claim 16.

* * * * *